US012807692B2

(12) United States Patent
Clarkson et al.

(10) Patent No.: US 12,807,692 B2
(45) Date of Patent: Nov. 24, 2026

(54) ANTIGEN BINDING PROTEIN

(71) Applicant: GLAXOSMITHKLINE INTELLECTUAL PROPERTY DEVELOPMENT LIMITED, Brentford (GB)

(72) Inventors: Jane Elizabeth Clarkson, Stevenage (GB); Caroline J. Dimech, Stevenage (GB); Mark R. Harpel, Collegeville, PA (US); Carol A. Harris, Stevenage (GB); Jian Zhang, Stevenage (GB)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 740 days.

(21) Appl. No.: 18/006,924

(22) PCT Filed: Jul. 29, 2021

(86) PCT No.: PCT/IB2021/056925

§ 371 (c)(1),
(2) Date: Jan. 26, 2023

(87) PCT Pub. No.: WO2022/024034

PCT Pub. Date: Feb. 3, 2022

(65) Prior Publication Data

US 2023/0279089 A1 Sep. 7, 2023

Related U.S. Application Data

(60) Provisional application No. 63/059,387, filed on Jul. 31, 2020.

(51) Int. Cl.

| | |
|---|---|
| ***C07K 16/22*** | (2006.01) |
| ***A61K 39/00*** | (2006.01) |
| ***A61P 9/00*** | (2006.01) |
| ***A61P 21/06*** | (2006.01) |
| ***C07K 16/40*** | (2006.01) |

(52) U.S. Cl.

CPC ................ *C07K 16/22* (2013.01); *A61P 9/00* (2018.01); *A61P 21/06* (2018.01); *C07K 16/40* (2013.01); *A61K 2039/505* (2013.01)

(58) Field of Classification Search

None

See application file for complete search history.

(56) References Cited

U.S. PATENT DOCUMENTS

| | | | |
|---|---|---|---|
| 10,450,288 | B2 | 10/2019 | Dowdell et al. |
| 2005/0043232 | A1 | 2/2005 | Lee et al. |
| 2010/0124552 | A1 | 5/2010 | Klein et al. |
| 2011/0293526 | A1 | 12/2011 | Plikus et al. |
| 2014/0199310 | A1 | 7/2014 | Birnie et al. |
| 2017/0218091 | A1 | 8/2017 | Ambrosi |
| 2018/0177880 | A1* | 6/2018 | Shailibhai .......... C07K 16/2809 |
| 2018/0207267 | A1 | 7/2018 | Schurpf et al. |

FOREIGN PATENT DOCUMENTS

| | | | |
|---|---|---|---|
| EP | 0854191 | A2 | 7/1998 |
| EP | 2500352 | A1 | 9/2012 |
| JP | 2017507915 | A | 3/2017 |
| WO | 2004037861 | A2 | 5/2004 |
| WO | 2006098758 | A2 | 9/2006 |
| WO | 2008011193 | A2 | 1/2008 |
| WO | 2012088190 | A1 | 6/2012 |
| WO | 2013045934 | A2 | 4/2013 |
| WO | 2013163479 | A1 | 10/2013 |
| WO | 2014009245 | A2 | 1/2014 |
| WO | 2016164501 | A1 | 10/2016 |
| WO | 2017217525 | A1 | 12/2017 |
| WO | 2018067740 | A1 | 4/2018 |

OTHER PUBLICATIONS

Iwashashi et al., Molecular Immunology, 36:1079-1091, 1999.*

Scott I.C., et al., "Mammalian BMP-1/Tolloid-Related Metalloproteinases, Including Novel Family Member Mammalian Tolloid-Like 2, Have Differential Enzymatic Activities and Distributions of Expression Relevant to Patterning and Skeletogenesis," Developmental Biology, 1999, vol. 213, pp. 283300, Retrieved from [https://doi.org/10.1006/dbio.1999.9383].

Grgurevic L., et al., "Circulating Bone Morphogenetic Protein 1-3 Isoform Increases Renal Fibrosis," Journal of the American Society of Nephrology, Apr. 1, 2011, vol. 22(4), pp. 681-692, DOI: 10.1681/ASN.2010070722.

Grgurevic L., et al., "Systemic Inhibition of BMP1-3 Decreases Progression of CCL 4-Induced Liver Fibrosis in Rats," Growth Factors, Feb. 27, 2017, vol. 35(6), pp. 201-215.

International Search Report and Written Opinion for International Application No. PCT/IB2021/056925, mailed Oct. 14, 2021, 16 Pages.

Ames R. S, et al., "Conversion of murine Fabs isolated from a combinatorial phage display library to full length immunoglobulins," J. Immunol. Methods, 184(2): 177-186 (1995).

Brinkmann U, et al., "Phage display of disulfide-stabilized Fv fragments," J. Immunol. Methods, 182(1): 41-50 (1995).

Green, et al., "Antigen-Specific Human Monoclonal Antibodies From Mice Engineered With Human Ig Heavy and Light Chain YACs," Nature Genetics, 1994, vol. 7, pp. 13-21.

(Continued)

*Primary Examiner* — Marianne P Allen

(74) *Attorney, Agent, or Firm* — Carly A. Shanahan

(57) ABSTRACT

Provided herein are antigen binding proteins that specifically bind to BMP1, TLL1 and/or TLL2. Also provided are pharmaceutical compositions containing the antigen binding proteins. The antigen binding proteins and pharmaceutical compositions described herein can be used to treat diseases associated with fibrotic conditions or disorders as well as to promote muscle growth and improve muscle function.

23 Claims, 19 Drawing Sheets

Specification includes a Sequence Listing.

(56) References Cited

OTHER PUBLICATIONS

Hammerling. G. J. et al., Monoclonal Antibodies and T-Cell Hybridomas, Research Monographs in Immunology No. 3, Ed, pp. 587. (Elsevier, 1981).
Harlow E., et al., "Antibodies, A Laboratory Manual," Cold Spring Harbor Laboratory Press, 1988, pp. 567-569.
Kettleborough C. A, et al., "Isolation of tumor cell-specific single-chain Fv from immunized mice using phage-antibody libraries and the re-construction of whole antibodies from these antibody fragments." European journal of immunology, 24(4):952-958 (1994).
Trackman P. "Lysyl Oxidase Isoforms and Potential Therapeutic Opportunities for Fibrosis and Cancer," Expert Opinion on Therapeutic Targets, 20(8):935-945 (2016).

* cited by examiner

SEQUENCE LISTING

<160> NUMBER OF SEQ ID NOS: 240

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 1

```
Arg Ala Ser Gln Ser Val Ser Ser Tyr Leu Ala
1               5                   10
```

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 2

```
Asp Ala Ser Asn Arg Ala Thr
1               5
```

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 3

```
Gln Gln Ser Asp Ser Trp Pro Pro Thr
1               5
```

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 4

```
Gly Tyr Tyr Met Ser
1               5
```

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 5

```
Trp Ile Asn Pro Leu Ser Gly Glu Thr Asn Tyr Ala Gln Lys Phe Gln
1               5                   10                  15

Gly
```

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 6

Asp Thr Gly Glu Leu Asp Gly Met Asn Trp Tyr Phe Asp Leu
1 5 10

<210> SEQ ID NO 7
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Leu Gly Tyr
20 25 30

Tyr Met Ser Trp Val Arg Gln Ala Pro Gly Gln Gly Leu Glu Trp Met
35 40 45

Gly Trp Ile Asn Pro Leu Ser Gly Glu Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Thr Gly Glu Leu Asp Gly Met Asn Trp Tyr Phe Asp Leu
100 105 110

Trp Gly Arg Gly Thr Leu Val Thr Val Ser Ser
115 120

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Asp Ser Trp Pro Pro
85 90 95

Thr Phe Gly Gly Gly Thr Lys Val Glu Ile Lys
100 105

<210> SEQ ID NO 9
<211> LENGTH: 214
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 10
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Gly Tyr
            20                  25                  30

Tyr Met Ser Trp Val Arg Gln Ala Pro Gly Gln Gly Leu Glu Trp Met
        35                  40                  45

Gly Trp Ile Asn Pro Leu Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 11
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 11
gagatcgtgc tgacccagag ccctgcaacc ctgtccctga gccctggcga aagggccact 60
ctgagctgca gggccagcca gagcgtgagc agctacctcg cctggtacca gcagaagccc 120
ggccaggccc ctaggctgct gatctacgac gccagcaaca gggccaccgg cattcccgca 180
aggttcagcg gcagcggcag cggcaccgac ttcaccctga ccatcagcag cctggagccc 240
gaagacttcg cagtctacta ctgccagcag agcgacagct ggccccccac cttcgggggc 300
ggcaccaagg tggagatcaa g 321

<210> SEQ ID NO 12
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12
caggtgcagc tcgtgcagag cggcgccgag gtgaaaaagc ccggcgcctc tgtcaaggtg 60
agctgcaagg ccagcggcta caccttcctg ggctactaca tgagctgggt gaggcaggct 120
cccggacagg gcctggagtg gatgggctgg atcaaccccc tgagcggcga gaccaactac 180
gcccagaagt tccagggcag ggtgaccatg accagggaca ccagcatcag caccgcctac 240
atggaactga gcaggctgag gagcgacgac accgccgtgt attactgcgc cagggacacc 300
ggcgagctgg acggcatgaa ctggtacttc gacctgtggg gcaggggcac cctggtgaca 360
gtgagcagc 369

<210> SEQ ID NO 13
<211> LENGTH: 1416
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
atgggctggt cctgcatcat cctgtttctg gtggccaccg ccaccggtgt gcacagccag 60
gtgcagctcg tgcagagcgg cgccgaggtg aaaaagcccg gcgcctctgt caaggtgagc 120
tgcaaggcca gcggctacac cttcctgggc tactacatga gctgggtgag gcaggctccc 180
ggacagggcc tggagtggat gggctggatc aaccccctga gcggcgagac caactacgcc 240
cagaagttcc agggcagggt gaccatgacc agggacacca gcatcagcac cgcctacatg 300
gaactgagca ggctgaggag cgacgacacc gccgtgtatt actgcgccag ggacaccggc 360
gagctggacg gcatgaactg gtacttcgac ctgtggggca ggggcaccct ggtgacagtg 420
agcagcgcca gcaccaaggg ccccagcgtg ttcccccctgg cccccagcag caagagcacc 480
agcggcggca cagccgccct gggctgcctg gtgaaggact acttccccga gcccgtgacc 540
gtgtcctgga acagcggagc cctgaccagc ggcgtgcaca ccttccccgc cgtgctgcag 600
agcagcggcc tgtacagcct gagcagcgtg gtgaccgtgc ccagcagcag cctgggcacc 660
cagacctaca tctgtaacgt gaaccacaag cccagcaaca ccaaggtgga caagaaggtg 720
gagcccaaga gctgtgacaa gacccacacc tgcccccccct gccctgcccc cgagctggcc 780
ggagccccca gcgtgttcct gttcccccc aagcctaagg acaccctgat gatcagcaga 840

```
acccccgagg tgacctgtgt ggtggtggat gtgagccacg aggaccctga ggtgaagttc    900

aactggtacg tggacggcgt ggaggtgcac aatgccaaga ccaagcccag ggaggagcag    960

tacaacagca cctaccgggt ggtgtccgtg ctgaccgtgc tgcaccagga ttggctgaac   1020

ggcaaggagt acaagtgtaa ggtgtccaac aaggccctgc ctgcccctat cgagaaaacc   1080

atcagcaagg ccaagggcca gcccagagag ccccaggtgt acaccctgcc ccctagcaga   1140

gatgagctga ccaagaacca ggtgtccctg acctgcctgg tgaagggctt ctaccccagc   1200

gacatcgccg tggagtggga gagcaacggc cagcccgaga acaactacaa gaccaccccc   1260

cctgtgctgg acagcgatgg cagcttcttc ctgtacagca agctgaccgt ggacaagagc   1320

agatggcagc agggcaacgt gttcagctgc tccgtgatgc acgaggccct gcacaatcac   1380

tacacccaga agagcctgag cctgtcccct ggcaag                             1416
```

<210> SEQ ID NO 14
<211> LENGTH: 699
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
atgggctggt cctgcatcat cctgtttctg gtggccaccg ccaccggtgt gcacagcgag     60

atcgtgctga cccagagccc tgcaaccctg tccctgagcc ctggcgaaag ggccactctg    120

agctgcaggg ccagccagag cgtgagcagc tacctcgcct ggtaccagca gaagcccggc    180

caggccccta ggctgctgat ctacgacgcc agcaacaggg ccaccggcat tcccgcaagg    240

ttcagcggca gcggcagcgg caccgacttc accctgacca tcagcagcct ggagcccgaa    300

gacttcgcag tctactactg ccagcagagc gacagctggc cccccacctt cgggggcggc    360

accaaggtgg agatcaagcg tacggtggcc gcccccagcg tgttcatctt cccccccagc    420

gatgagcagc tgaagagcgg caccgccagc gtggtgtgtc tgctgaacaa cttctacccc    480

cgggaggcca aggtgcagtg gaaggtggac aatgccctgc agagcggcaa cagccaggag    540

agcgtgaccg agcaggacag caaggactcc acctacagcc tgagcagcac cctgaccctg    600

agcaaggccg actacgagaa gcacaaggtg tacgcctgtg aggtgaccca ccagggcctg    660

tccagccccg tgaccaagag cttcaaccgg ggcgagtgc                           699
```

<210> SEQ ID NO 15
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

```
Gln Ala Ser Gln Asp Ile Ala Asn Tyr Leu Asn
1               5                   10
```

<210> SEQ ID NO 16
<211> LENGTH: 7
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 16

Asp Ala Ser Asn Leu Glu Thr
1               5


<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Gln Ala Asp Thr Leu Pro Phe Thr
1               5


<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Asp Tyr Trp Ser
1               5


<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Glu Ile Asp Trp Ser Gly Ala Thr Asn Tyr Asn Pro Ser Leu Lys Ser
1               5                   10                  15


<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Gly Ser Lys Glu Leu Ser Phe Asp Ile
1               5                   10


<210> SEQ ID NO 21
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Thr Leu Pro Phe
                85                  90                  95

Thr Phe Gly Gly Gly Thr Lys Val Glu Ile Lys
            100                 105


<210> SEQ ID NO 22
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Phe Gly Asp
            20                  25                  30

Tyr Trp Ser Trp Ile Arg Gln Pro Pro Gly Lys Gly Leu Glu Trp Ile
        35                  40                  45

Gly Glu Ile Asp Trp Ser Gly Ala Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Lys Glu Leu Ser Phe Asp Ile Trp Gly Gln Gly Thr
            100                 105                 110

Met Val Thr Val Ser Ser
        115


<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Asn Tyr
            20                  25                  30

Leu Asn Trp Tyr Gln Gln Lys Pro Gly Lys Ala Pro Lys Leu Leu Ile
        35                  40                  45
```

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Ala Asp Thr Leu Pro Phe
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 24
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Phe Gly Asp
20 25 30

Tyr Trp Ser Trp Ile Arg Gln Pro Pro Gly Lys Gly Leu Glu Trp Ile
35 40 45

Gly Glu Ile Asp Trp Ser Gly Ala Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Gly Ser Lys Glu Leu Ser Phe Asp Ile Trp Gly Gln Gly Thr
100 105 110

Met Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser

```
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 25
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

```
gacatccaga tgacccagtc tccatcctcc ctgtctgcat ctgtaggaga cagagtcacc     60

atcacttgcc aggcgagtca ggacattgcc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatatta ctgtcagcag gccgataccc tccctttcac ttttggcgga    300

gggaccaagg ttgagatcaa a                                              321
```

<210> SEQ ID NO 26
<211> LENGTH: 354
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 26

caagtacaat tacaacagtg gggagctggt ttattaaagc cttcagaaac tttaagtttg     60

acctgtgctg tttacggtgg atcatttttt ggtgattact ggagttggat tcgtcaacca    120

ccaggcaaag gattggagtg gatcggtgag atagactggt caggcgcgac taactacaat    180

ccaagtttaa aatccagggt tactatctcc gtagacacgt ccaagaacca gttctccctg    240

aagctgagtt ctgtgaccgc cgcagacacg gcggtgtact actgcgccag aggcggttct    300

aaagaattgt cattcgacat atggggtcag ggtacaatgg tcaccgtctc ctca          354


<210> SEQ ID NO 27
<211> LENGTH: 1343
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

caagtacaat tacaacagtg gggagctggt ttattaaagc cttcagaaac tttaagtttg     60

acctgtgctg tttacggtgg atcatttttt ggtgattact ggagttggat tcgtcaacca    120

ccaggcaaag gattggagtg gatcggtgag atagactggt caggcgcgac taactacaat    180

ccaagtttaa aatccagggt tactatctcc gtagacacgt ccaagaacca gttctccctg    240

aagctgagtt ctgtgaccgc cgcagacacg gcggtgtact actgcgccag aggcggttct    300

aaagaattgt cattcgacat atggggtcag ggtacaatgg tcaccgtctc ctcagccagc    360

accaagggcc ccagcgtgtt ccccctggcc cccagcagca agagcaccag cggcggcaca    420

gccgccctgg gctgcctggt gaaggactac ttccccgagc ccgtgaccgt gtcctggaac    480

agcggagccc tgaccagcgg cgtgcacacc ttccccgccg tgctgcagag cagcggcctg    540

tacagcctga gcagctggtg accgtgccca gcagcagcct gggcacccag acctacatct    600

gtaacgtgaa ccacaagccc agcaacacca aggtggacaa gaaggtggag cccaagagct    660

gtgacaagac ccacacctgc ccccccctgcc ctgcccccga gctggccgga gcccccagcg    720

tgttcctgtt cccccccaag cctaaggaca ccctgatgat cagcagaacc cccgaggtga    780

cctgtgtggt ggtggatgtg agccacgagg accctgaggt gaagttcaac tggtacgtgg    840

acggcgtgga ggtgcacaat gccaagacca agcccaggga ggagcagtac aacagcacct    900

accgggtggt gtccgtgctg accgtgctgc accaggattg gctgaacggc aaggagtaca    960

agtgtaaggt gtccaacaag gccctgcctg cccctatcga gaaaaccatc agcaaggcca   1020

agggccagcc cagagagccc caggtgtaca ccctgccccc tagcagagat gagctgacca   1080

agaaccaggt gtccctgacc tgcctggtga agggcttcta ccccagcgac atcgccgtgg   1140

agtgggagag caacggccag cccgagaaca actacaagac caccccccct gtgctggaca   1200

gcgatggcag cttcttcctg tacagcaagc tgaccgtgga caagagcaga tggcagcagg   1260

gcaacgtgtt cagctgctcc gtgatgcacg aggccctgca caatcactac acccagaaga   1320

gcctgagcct gtcccctggc aag                                           1343


<210> SEQ ID NO 28
```

<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
gacatccaga tgacccagtc tccatcctcc ctgtctgcat ctgtaggaga cagagtcacc     60

atcacttgcc aggcgagtca ggacattgcc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatatta ctgtcagcag gccgataccc tccctttcac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

<210> SEQ ID NO 29
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Thr Leu Pro Phe
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190
```

```
Thr Cys Glu Ala Thr His Lys Thr Ser Thr Ser Pro Ile Val Lys Ser
        195                 200                 205

Phe Asn Arg Asn Glu Cys
    210


<210> SEQ ID NO 30
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

gacatccaga tgactcagtc cccctctagc ctgagcgcta gcgtgggcga cagggtgacc      60

atcacctgcc aggccagcca ggacatcgcc aactacctga actggtacca gcagaagccc     120

ggcaaggccc ccaaactgct gatctacgac gcctcaaacc tcgagaccgg cgtgcctagc     180

aggtttagcg gcagcggcag cggcaccgac ttcaccttca ccatcagcag cctgcagccc     240

gaggatatcg ccacctacta ctgccagcag gccgacaccc tgcccttcac cttcggcgga     300

ggcaccaagg tggagattaa gagggctgac gcggcgccca ccgtgagcat cttccccccc     360

agcagcgagc agctgactag cggcggagcc tctgtggtgt gcttcctgaa caacttctac     420

cccaaggaca tcaacgtgaa gtggaagatc gacggcagcg agaggcagaa cggagtcctc     480

aacagctgga ccgaccagga cagcaaggat agcacctaca gcatgagcag caccctgacc     540

ctgaccaagg acgagtacga gaggcacaac agctacacct gcgaagccac ccacaaaacc     600

tccaccagcc ccatcgtgaa gagcttcaat aggaacgagt gc                        642


<210> SEQ ID NO 31
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Phe Gly Asp
            20                  25                  30

Tyr Trp Ser Trp Ile Arg Gln Pro Pro Gly Lys Gly Leu Glu Trp Ile
        35                  40                  45

Gly Glu Ile Asp Trp Ser Gly Ala Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Lys Glu Leu Ser Phe Asp Ile Trp Gly Gln Gly Thr
            100                 105                 110

Met Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140
```

```
Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Ala Gly Ala Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

<210> SEQ ID NO 32
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 32

```
caggtgcagc tgcagcagtg gggcgccgga ctgctgaagc ccagcgagac cctgagcctg     60

acctgcgccg tgtacggcgg gtccttcttc ggcgactact ggagctggat caggcagccc    120

cccggcaaag gcctggagtg gatcggcgag atcgactgga gcggcgccac caactacaac    180

cccagcctca agagcagggt gaccatcagc gtggacacca gcaagaacca gttcagcctg    240

aagctgagca gcgtgaccgc cgccgacacc gccgtgtact attgcgccag gggcggcagc    300
```

```
aaggagctga gcttcgacat ctggggccag ggcactatgg tcaccgtgag cagcgctaaa    360

accaccgccc cctccgtgta ccccctggcg cccgtctgtg gcgacaccac cggcagcagc    420

gtgacactgg gctgcctggt gaagggctac ttccccgagc ccgtcaccct gacctggaat    480

agcggaagcc tgtcaagcgg cgtgcacact ttccccgccg tgctgcagtc tgacctgtac    540

accctgagca gcagcgtgac cgtgaccagc agcacctggc ccagccagtc tatcacttgc    600

aacgtggccc accctgccag ctccaccaag gtggacaaga agatcgagcc taggggaccc    660

accattaaac cctgcccccc ctgcaagtgc cccgcccccca atctggccgg agcccccagc    720

gtgtttatct tcccccccaa gatcaaggac gtgctgatga tcagcctgag ccccatcgtg    780

acctgcgtgg tggtggacgt gagcgaggac gacccagacg tgcagatcag ctggtttgtg    840

aacaacgtgg aggtgcacac cgcccagacc cagacccaca gggaggatta caacagcacc    900

ctgagggtgg tgagcgccct gcccatccag caccaggact ggatgtccgg caaggagttc    960

aagtgcaagg tgaacaacaa ggacctgccc gcccccatcg agaggaccat cagcaagcct   1020

aagggcagcg tgagggcacc ccaggtctac gtgctgcccc ccccagagga ggaaatgacc   1080

aagaagcagg tgaccctgac ctgcatggtg accgacttca tgcccgagga catctacgtg   1140

gagtggacca acaacggcaa gaccgagctg aactacaaga acaccgagcc cgtgctggac   1200

agcgacggca gctacttcat gtatagcaag ctgcgggtcg agaagaagaa ctgggtggag   1260

aggaacagct acagctgcag cgtcgtgcac gaaggcctcc acaaccacca caccaccaag   1320

agcttcagca ggacccccgg gaag                                          1344


<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Arg Ala Ser Gln Gly Ile Ser Ser Trp Leu Ala
1               5                   10


<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ala Ser Ser Leu Gln Ser
1               5


<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35
```

Gln Gln Ala Leu Ser Leu Pro Tyr Thr
1               5

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Glu Trp Ala Ile Ser
1               5

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ala Ile Ile Pro Lys Phe Gly Thr Ala Glu Tyr Ala Gln Lys Phe Gln
1               5                   10                  15

Gly

<210> SEQ ID NO 38
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Ala Lys Tyr Tyr Tyr Ala Glu Asp Tyr Met Asp Val
1               5                   10

<210> SEQ ID NO 39
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Ser Leu Pro Tyr
                85                  90                  95

```
Thr Phe Gly Gly Gly Thr Lys Val Glu Ile Lys
            100                 105


<210> SEQ ID NO 40
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Glu Trp
            20                  25                  30

Ala Ile Ser Trp Val Arg Gln Ala Pro Gly Gln Gly Leu Glu Trp Met
        35                  40                  45

Gly Ala Ile Ile Pro Lys Phe Gly Thr Ala Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Lys Tyr Tyr Tyr Ala Glu Asp Tyr Met Asp Val Trp
            100                 105                 110

Gly Lys Gly Thr Thr Val Thr Val Ser Ser
        115                 120


<210> SEQ ID NO 41
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Ser Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 42
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Glu Trp
            20                  25                  30

Ala Ile Ser Trp Val Arg Gln Ala Pro Gly Gln Gly Leu Glu Trp Met
        35                  40                  45

Gly Ala Ile Ile Pro Lys Phe Gly Thr Ala Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Lys Tyr Tyr Tyr Ala Glu Asp Tyr Met Asp Val Trp
            100                 105                 110

Gly Lys Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

```
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 43
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43

gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gcactcagtc tcccttacac ttttggcgga    300

gggaccaagg ttgagatcaa a                                              321


<210> SEQ ID NO 44
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

caggtgcagc tggtgcagtc tggggctgag gtgaagaagc ctgggtcctc ggtgaaggtc     60

tcctgcaagg cttctggagg caccttcagc gagtgggcta tcagctgggt gcgacaggcc    120

cctggacaag ggcttgagtg gatgggagct atcatcccta agtttggtac agcagagtac    180

gcacagaagt tccagggcag agtcacgatt accgcggacg aatccacgag cacagcctac    240
```

atggagctga gcagcctgag atctgaggac acggcggtgt actactgcgc cagaggtgct 300
aagtactact acgctgagga ctacatggac gtatggggca agggtacaac tgtcaccgtc 360
tcctca 366

<210> SEQ ID NO 45
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 45
caggtgcagc tggtgcagtc tggggctgag gtgaagaagc ctgggtcctc ggtgaaggtc 60
tcctgcaagg cttctggagg caccttcagc gagtgggcta tcagctgggt gcgacaggcc 120
cctggacaag ggcttgagtg gatgggagct atcatcccta agtttggtac agcagagtac 180
gcacagaagt tccagggcag agtcacgatt accgcggacg aatccacgag cacagcctac 240
atggagctga gcagcctgag atctgaggac acggcggtgt actactgcgc cagaggtgct 300
aagtactact acgctgagga ctacatggac gtatggggca agggtacaac tgtcaccgtc 360
tcctcagcca gcaccaaggg ccccagcgtg ttcccccctgg cccccagcag caagagcacc 420
agcggcggca cagccgccct gggctgcctg gtgaaggact acttccccga gcccgtgacc 480
gtgtcctgga acagcggagc cctgaccagc ggcgtgcaca ccttccccgc cgtgctgcag 540
agcagcggcc tgtacagcct gagcagcgtg gtgaccgtgc ccagcagcag cctgggcacc 600
cagacctaca tctgtaacgt gaaccacaag cccagcaaca ccaaggtgga caagaaggtg 660
gagcccaaga gctgtgacaa gacccacacc tgcccccccct gccctgcccc cgagctggcc 720
ggagccccca gcgtgttcct gttccccccc aagcctaagg acaccctgat gatcagcaga 780
acccccgagg tgacctgtgt ggtggtggat gtgagccacg aggaccctga ggtgaagttc 840
aactggtacg tggacggcgt ggaggtgcac aatgccaaga ccaagcccag ggaggagcag 900
tacaacagca cctaccgggt ggtgtccgtg ctgaccgtgc tgcaccagga ttggctgaac 960
ggcaaggagt acaagtgtaa ggtgtccaac aaggccctgc ctgcccctat cgagaaaacc 1020
atcagcaagg ccaagggcca gcccagagag ccccaggtgt acaccctgcc ccctagcaga 1080
gatgagctga ccaagaacca ggtgtccctg acctgcctgg tgaagggctt ctaccccagc 1140
gacatcgccg tggagtggga gagcaacggc cagcccgaga acaactacaa gaccaccccc 1200
cctgtgctgg acagcgatgg cagcttcttc ctgtacagca agctgaccgt ggacaagagc 1260
agatggcagc agggcaacgt gttcagctgc tccgtgatgc acgaggccct gcacaatcac 1320
tacacccaga agagcctgag cctgtcccct ggcaag 1356

<210> SEQ ID NO 46
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 46
gacatccaga tgacccagtc tccatcttcc gtgtctgcat ctgtaggaga cagagtcacc 60
atcacttgtc gggcgagtca gggtattagc agctggttag cctggtatca gcagaaacca 120

```
gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag gcactcagtc tcccttacac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

```
<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Arg Ala Ser Gln Ser Val Ser Ser Tyr Leu Ala
1               5                   10


<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asp Ala Ser Asn Arg Ala Thr
1               5


<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gln Gln Ser Asp Ser Trp Pro Pro Thr
1               5


<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Tyr Tyr Met Asn
1               5
```

```
<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Trp Ile Asn Pro Ser Ser Gly Glu Thr Asn Tyr Ala Gln Lys Phe Gln
1               5                   10                  15

Gly


<210> SEQ ID NO 52
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asp Thr Gly Glu Leu Asp Gly Met Asn Trp Tyr Phe Asp Leu
1               5                   10


<210> SEQ ID NO 53
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105


<210> SEQ ID NO 54
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Met Gly Tyr
            20                  25                  30

Tyr Met Asn Trp Val Arg Gln Ala Pro Gly Gln Gly Leu Glu Trp Met
        35                  40                  45

Gly Trp Ile Asn Pro Ser Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120
```

<210> SEQ ID NO 55
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 56
<211> LENGTH: 453

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 56

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Met Gly Tyr
            20                  25                  30

Tyr Met Asn Trp Val Arg Gln Ala Pro Gly Gln Gly Leu Glu Trp Met
        35                  40                  45

Gly Trp Ile Asn Pro Ser Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
```

```
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 57
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57

gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa a                                               321


<210> SEQ ID NO 58
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58

caggtgcagc tggtgcagtc tggggctgag gtgaagaagc ctggggcctc agtgaaggtc     60

tcctgcaagg cttctggata caccttcatg ggctactata tgaattgggt gcgacaggcc    120

cctggacaag ggcttgagtg gatgggatgg atcaaccctt ctagtggtga gacaaactat    180

gcacagaagt ttcagggcag ggtcaccatg accagggaca cgtccatcag cacagcctac    240

atggagctga gcaggctgag atctgacgac acggcggtgt actactgcgc cagagacacg    300

ggagaacttg acggaatgaa ctggtacttc gacctatggg ggagaggtac cttggtcacc    360

gtctcctca                                                             369


<210> SEQ ID NO 59
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
```

-continued

```
caggtgcagc tggtgcagtc tggggctgag gtgaagaagc ctggggcctc agtgaaggtc     60

tcctgcaagg cttctggata caccttcatg ggctactata tgaattgggt gcgacaggcc    120

cctggacaag ggcttgagtg gatgggatgg atcaaccctt ctagtggtga gacaaactat    180

gcacagaagt ttcagggcag ggtcaccatg accagggaca cgtccatcag cacagcctac    240

atggagctga gcaggctgag atctgacgac acggcggtgt actactgcgc cagagacacg    300

ggagaacttg acggaatgaa ctggtacttc gacctatggg ggagaggtac cttggtcacc    360

gtctcctcag ccagcaccaa gggccccagc gtgttccccc tggcccccag cagcaagagc    420

accagcggcg gcacagccgc cctgggctgc ctggtgaagg actacttccc cgagcccgtg    480

accgtgtcct ggaacagcgg agccctgacc agcggcgtgc acaccttccc cgccgtgctg    540

cagagcagcg gcctgtacag cctgagcagc gtggtgaccg tgcccagcag cagcctgggc    600

acccagacct acatctgtaa cgtgaaccac aagcccagca acaccaaggt ggacaagaag    660

gtggagccca agagctgtga caagacccac acctgccccc cctgccctgc ccccgagctg    720

gccggagccc ccagcgtgtt cctgttcccc cccaagccta aggacaccct gatgatcagc    780

agaacccccg aggtgacctg tgtggtggtg gatgtgagcc acgaggaccc tgaggtgaag    840

ttcaactggt acgtggacgg cgtggaggtg cacaatgcca agaccaagcc cagggaggag    900

cagtacaaca gcacctaccg ggtggtgtcc gtgctgaccg tgctgcacca ggattggctg    960

aacggcaagg agtacaagtg taaggtgtcc aacaaggccc tgcctgcccc tatcgagaaa   1020

accatcagca aggccaaggg ccagcccaga gagccccagg tgtacaccct gccccctagc   1080

agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

ccccctgtgc tggacagcga tggcagcttc ttcctgtaca gcaagctgac cgtggacaag   1260

agcagatggc agcagggcaa cgtgttcagc tgctccgtga tgcacgaggc cctgcacaat   1320

cactacaccc agaagagcct gagcctgtcc cctggcaag                          1359
```

<210> SEQ ID NO 60
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                        642
```

<210> SEQ ID NO 61
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

Arg Ala Ser Gln Ser Val Ser Ser Tyr Leu Ala
1 5 10

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

Asp Ala Ser Asn Arg Ala Thr
1 5

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Gln Gln Ser Asp Ser Trp Pro Pro Thr
1 5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Ser Tyr Tyr Met Asn
1 5

<210> SEQ ID NO 65
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Ile Ile Asn Pro Ser Ser Gly Glu Thr Ser Tyr Ala Gln Lys Phe Gln
1 5 10 15

Gly

```
<210> SEQ ID NO 66
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asp Thr Gly Glu Leu Asp Gly Met Asn Trp Tyr Phe Asp Leu
1               5                   10


<210> SEQ ID NO 67
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Tyr Met Asn Trp Val Arg Gln Ala Pro Gly Gln Gly Leu Glu Trp Met
        35                  40                  45

Gly Ile Ile Asn Pro Ser Ser Gly Glu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120


<210> SEQ ID NO 68
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95
```

Thr Phe Gly Gly Gly Thr Lys Val Glu Ile Lys
            100                 105

<210> SEQ ID NO 69
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Tyr Met Asn Trp Val Arg Gln Ala Pro Gly Gln Gly Leu Glu Trp Met
        35                  40                  45

-continued

```
Gly Ile Ile Asn Pro Ser Ser Gly Glu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 71
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 71
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag tccgactcct ggcctcctac ttttggcgga 300
gggaccaagg ttgagatcaa a 321

<210> SEQ ID NO 72
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 72
caggtgcagc tggtgcagtc tggggctgag gtgaagaagc ctggggcctc agtgaaggtt 60
tcctgcaagg catctggata caccttcagg agctactata tgaattgggt gcgacaggcc 120
cctggacaag ggcttgagtg gatgggaata atcaacccta gttcgggtga gacaagctac 180
gcacagaagt tccagggcag agtcaccatg accagggaca cgtccacgag cacagtctac 240
atggagctga gcagcctgag atctgaggac acggcggtgt actactgcgc cagagacacg 300
ggagaacttg acggaatgaa ctggtacttc gacctatggg ggagaggtac cttggtcacc 360
gtctcctca 369

<210> SEQ ID NO 73
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 73
caggtgcagc tggtgcagtc tggggctgag gtgaagaagc ctggggcctc agtgaaggtt 60
tcctgcaagg catctggata caccttcagg agctactata tgaattgggt gcgacaggcc 120
cctggacaag ggcttgagtg gatgggaata atcaacccta gttcgggtga gacaagctac 180
gcacagaagt tccagggcag agtcaccatg accagggaca cgtccacgag cacagtctac 240
atggagctga gcagcctgag atctgaggac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540

```
cagagcagcg gcctgtacag cctgagcagc gtggtgaccg tgcccagcag cagcctgggc    600

acccagacct acatctgtaa cgtgaaccac aagcccagca acaccaaggt ggacaagaag    660

gtggagccca agagctgtga caagacccac acctgccccc cctgccctgc ccccgagctg    720

gccggagccc ccagcgtgtt cctgttcccc cccaagccta aggacaccct gatgatcagc    780

agaacccccg aggtgacctg tgtggtggtg gatgtgagcc acgaggaccc tgaggtgaag    840

ttcaactggt acgtggacgg cgtggaggtg cacaatgcca agaccaagcc cagggaggag    900

cagtacaaca gcacctaccg ggtggtgtcc gtgctgaccg tgctgcacca ggattggctg    960

aacggcaagg agtacaagtg taaggtgtcc aacaaggccc tgcctgcccc tatcgagaaa   1020

accatcagca aggccaaggg ccagcccaga gagccccagg tgtacaccct gccccctagc   1080

agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

cccccctgtgc tggacagcga tggcagcttc ttcctgtaca gcaagctgac cgtggacaag   1260

agcagatggc agcagggcaa cgtgttcagc tgctccgtga tgcacgaggc cctgcacaat   1320

cactacaccc agaagagcct gagcctgtcc cctggcaag                          1359
```

<210> SEQ ID NO 74
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 74

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 75

```
Arg Ala Ser Gln Ser Val Ser Ser Tyr Leu Ala
1               5                   10
```

<210> SEQ ID NO 76

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 76

Asp Ala Ser Asn Arg Ala Thr
1 5

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 77

Gln Gln Ser Asp Ser Trp Pro Pro Thr
1 5

<210> SEQ ID NO 78
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

Gly Tyr Tyr Met Ser
1 5

<210> SEQ ID NO 79
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

Trp Ile Asn Pro Asn Ser Gly Glu Thr Ile Tyr Ala Gln Lys Phe Gln
1 5 10 15

Gly

<210> SEQ ID NO 80
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

Asp Thr Gly Glu Leu Asp Gly Met Asn Trp Tyr Phe Asp Leu
1 5 10

<210> SEQ ID NO 81
<211> LENGTH: 107
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105
```

<210> SEQ ID NO 82
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Tyr Met Ser Trp Val Arg Gln Ala Pro Gly Gln Gly Leu Glu Trp Met
        35                  40                  45

Gly Trp Ile Asn Pro Asn Ser Gly Glu Thr Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120
```

<210> SEQ ID NO 83
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 83

```
Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Tyr Met Ser Trp Val Arg Gln Ala Pro Gly Gln Gly Leu Glu Trp Met
        35                  40                  45

Gly Trp Ile Asn Pro Asn Ser Gly Glu Thr Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 85
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85

```
gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240
```

gaagattttg cagtttatta ctgtcagcag tccgactcct ggcctcctac ttttggcgga 300
gggaccaagg ttgagatcaa a 321

<210> SEQ ID NO 86
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 86
caggtgcagc tggtgcagtc tggggctgag gtgaagaagc ctggggcctc agtgaaggtc 60
tcctgcaagg cttctggata caccttccgg ggctactata tgagttgggt gcgacaggcc 120
cctggacaag ggcttgagtg gatgggatgg atcaacccta acagtggtga gacaatttat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctca 369

<210> SEQ ID NO 87
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87
caggtgcagc tggtgcagtc tggggctgag gtgaagaagc ctggggcctc agtgaaggtc 60
tcctgcaagg cttctggata caccttccgg ggctactata tgagttgggt gcgacaggcc 120
cctggacaag ggcttgagtg gatgggatgg atcaacccta acagtggtga gacaatttat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gccccctagc 1080

```
agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

ccccctgtgc tggacagcga tggcagcttc ttcctgtaca gcaagctgac cgtggacaag   1260

agcagatggc agcagggcaa cgtgttcagc tgctccgtga tgcacgaggc cctgcacaat   1320

cactacaccc agaagagcct gagcctgtcc cctggcaag                          1359
```

<210> SEQ ID NO 88
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

<210> SEQ ID NO 89
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 89

```
Arg Ala Ser Gln Ser Val Ser Ser Tyr Leu Ala
1               5                   10
```

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 90

```
Asp Ala Ser Asn Arg Ala Thr
1               5
```

<210> SEQ ID NO 91
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 91

Gln Gln Ser Asp Ser Trp Pro Pro Thr
1 5

<210> SEQ ID NO 92
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 92

Gly Tyr Tyr Met Ser
1 5

<210> SEQ ID NO 93
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 93

Trp Ile Asn Pro Asn Ser Gly Glu Thr Phe Tyr Ala Gln Lys Phe Gln
1 5 10 15

Gly

<210> SEQ ID NO 94
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 94

Asp Thr Gly Glu Leu Asp Gly Met Asn Trp Tyr Phe Asp Leu
1 5 10

<210> SEQ ID NO 95
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 95

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly

```
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105


<210> SEQ ID NO 96
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
            20                  25                  30

Tyr Met Ser Trp Val Arg Gln Ala Pro Gly Gln Gly Leu Glu Trp Met
        35                  40                  45

Gly Trp Ile Asn Pro Asn Ser Gly Glu Thr Phe Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120


<210> SEQ ID NO 97
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 98
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
            20                  25                  30

Tyr Met Ser Trp Val Arg Gln Ala Pro Gly Gln Gly Leu Glu Trp Met
        35                  40                  45

Gly Trp Ile Asn Pro Asn Ser Gly Glu Thr Phe Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 99
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa a                                              321
```

<210> SEQ ID NO 100
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 100

```
caggtgcagc tggtgcagtc tggggctgag gtgaagaagc ctggggcctc agtgaaggtc     60
```

tcctgcaagg cttctggata caccttctcg ggctactata tgagttgggt gcgacaggcc 120
cctggacaag ggcttgagtg gatgggatgg atcaacccta acagtggtga gacattttat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctca 369

<210> SEQ ID NO 101
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101
caggtgcagc tggtgcagtc tggggctgag gtgaagaagc ctggggcctc agtgaaggtc 60
tcctgcaagg cttctggata caccttctcg ggctactata tgagttgggt gcgacaggcc 120
cctggacaag ggcttgagtg gatgggatgg atcaacccta acagtggtga gacattttat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gcccccctagc 1080 agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 102
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 102

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag tccgactcct ggcctcctac ttttggcgga    300
gggaccaagg ttgagatcaa acgtacggtg gccgccccca gcgtgttcat cttccccccc    360
agcgatgagc agctgaagag cggcaccgcc agcgtggtgt gtctgctgaa caacttctac    420
ccccgggagg ccaaggtgca gtggaaggtg gacaatgccc tgcagagcgg caacagccag    480
gagagcgtga ccgagcagga cagcaaggac tccacctaca gcctgagcag caccctgacc    540
ctgagcaagg ccgactacga gaagcacaag gtgtacgcct gtgaggtgac ccaccagggc    600
ctgtccagcc ccgtgaccaa gagcttcaac cggggcgagt gc                       642
```

<210> SEQ ID NO 103
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 103

```
Arg Ala Ser Gln Ser Val Ser Ser Tyr Leu Ala
1               5                   10
```

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 104

```
Asp Ala Ser Asn Arg Ala Thr
1               5
```

<210> SEQ ID NO 105
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 105

```
Gln Gln Ser Asp Ser Trp Pro Pro Thr
1               5
```

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 106

Gly Tyr Tyr Met Ser
1 5

<210> SEQ ID NO 107
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 107

Trp Ile Asn Pro Asn Ser Gly Glu Thr Tyr Tyr Ala Gln Lys Phe Gln
1 5 10 15

Gly

<210> SEQ ID NO 108
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 108

Asp Thr Gly Glu Leu Asp Gly Met Asn Trp Tyr Phe Asp Leu
1 5 10

<210> SEQ ID NO 109
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 109

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Asp Ser Trp Pro Pro
85 90 95

Thr Phe Gly Gly Gly Thr Lys Val Glu Ile Lys
100 105

<210> SEQ ID NO 110
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 110

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Gly Gly Tyr
20 25 30

Tyr Met Ser Trp Val Arg Gln Ala Pro Gly Gln Gly Leu Glu Trp Met
35 40 45

Gly Trp Ile Asn Pro Asn Ser Gly Glu Thr Tyr Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Thr Gly Glu Leu Asp Gly Met Asn Trp Tyr Phe Asp Leu
100 105 110

Trp Gly Arg Gly Thr Leu Val Thr Val Ser Ser
115 120

<210> SEQ ID NO 111
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 111

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Asp Ser Trp Pro Pro
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

```
Phe Asn Arg Gly Glu Cys
    210


<210> SEQ ID NO 112
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Gly Tyr
            20                  25                  30

Tyr Met Ser Trp Val Arg Gln Ala Pro Gly Gln Gly Leu Glu Trp Met
        35                  40                  45

Gly Trp Ile Asn Pro Asn Ser Gly Glu Thr Tyr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 113
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag tccgactcct ggcctcctac ttttggcgga     300

gggaccaagg ttgagatcaa a                                                321


<210> SEQ ID NO 114
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114

caggtgcagc tggtgcagtc tggggctgag gtgaagaagc ctggggcctc agtgaaggtc      60

tcctgcaagg cttctggata caccttcggg ggctactata tgtcgtgggt gcgacaggcc     120

cctggacaag ggcttgagtg gatgggatgg atcaacccta acagtggtga gacatattat     180

gcacagaagt ttcagggcag ggtcaccatg accagggaca cgtccatcag cacagcctac     240

atggagctga gcaggctgag atctgacgac acggcggtgt actactgcgc cagagacacg     300

ggagaacttg acggaatgaa ctggtacttc gacctatggg ggagaggtac cttggtcacc     360

gtctcctca                                                              369


<210> SEQ ID NO 115
<211> LENGTH: 1359
<212> TYPE: DNA
<213> ORGANISM: Artificial Sequence
```

<220> FEATURE:
<221> NAME/KEY: source
<223> OTHER INFORMATION: /note="Description of Artificial Sequence:
Synthetic polynucleotide"

<400> SEQUENCE: 115
caggtgcagc tggtgcagtc tggggctgag gtgaagaagc ctggggcctc agtgaaggtc 60
tcctgcaagg cttctggata caccttcggg ggctactata tgtcgtgggt gcgacaggcc 120
cctggacaag ggcttgagtg gatgggatgg atcaacccta acagtggtga gacatattat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gccccctagc 1080
agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 116
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 116
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag tccgactcct ggcctcctac ttttggcgga 300
gggaccaagg ttgagatcaa acgtacggtg gccgccccca gcgtgttcat cttccccccc 360
agcgatgagc agctgaagag cggcaccgcc agcgtggtgt gtctgctgaa caacttctac 420

-continued

```
ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642


<210> SEQ ID NO 117
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Arg Ala Ser Gln Ser Val Ser Ser Tyr Leu Ala
1               5                   10


<210> SEQ ID NO 118
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Asp Ala Ser Asn Arg Ala Thr
1               5


<210> SEQ ID NO 119
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gln Gln Ser Asp Ser Trp Pro Pro Thr
1               5


<210> SEQ ID NO 120
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Tyr Tyr Met Asn
1               5


<210> SEQ ID NO 121
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121
```

Trp Ile Asn Pro Leu Ser Gly Glu Thr Asn Tyr Ala Gln Lys Phe Gln
1 5 10 15

Gly

<210> SEQ ID NO 122
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 122

Asp Thr Gly Glu Leu Asp Gly Met Asn Trp Tyr Phe Asp Leu
1 5 10

<210> SEQ ID NO 123
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Asp Ser Trp Pro Pro
85 90 95

Thr Phe Gly Gly Gly Thr Lys Val Glu Ile Lys
100 105

<210> SEQ ID NO 124
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe His Gly Tyr
20 25 30

Tyr Met Asn Trp Val Arg Gln Ala Pro Gly Gln Gly Leu Glu Trp Met
35 40 45

Gly Trp Ile Asn Pro Leu Ser Gly Glu Thr Asn Tyr Ala Gln Lys Phe
50 55 60

Gln Gly Arg Val Thr Met Thr Arg Asp Thr Ser Ile Ser Thr Ala Tyr

```
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120


<210> SEQ ID NO 125
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 126
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe His Gly Tyr
            20                  25                  30

Tyr Met Asn Trp Val Arg Gln Ala Pro Gly Gln Gly Leu Glu Trp Met
        35                  40                  45

Gly Trp Ile Asn Pro Leu Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Pro Gly Lys
    450


<210> SEQ ID NO 127
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127

gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag tccgactcct ggcctcctac ttttggcgga     300

gggaccaagg ttgagatcaa a                                               321


<210> SEQ ID NO 128
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128

caggtgcagc tggtgcagtc tggggctgag gtgaagaagc ctggggcctc agtgaaggtc      60

tcctgcaagg cttctggata caccttccat ggctactata tgaattgggt gcgacaggcc     120

cctggacaag ggcttgagtg gatgggatgg atcaaccctc tgagtggtga gacaaactat     180

gcacagaagt ttcagggcag ggtcaccatg accagggaca cgtccatcag cacagcctac     240

atggagctga gcaggctgag atctgacgac acggcggtgt actactgcgc cagagacacg     300

ggagaacttg acggaatgaa ctggtacttc gacctatggg ggagaggtac cttggtcacc     360

gtctcctca                                                             369


<210> SEQ ID NO 129
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

caggtgcagc tggtgcagtc tggggctgag gtgaagaagc ctggggcctc agtgaaggtc      60

tcctgcaagg cttctggata caccttccat ggctactata tgaattgggt gcgacaggcc     120

cctggacaag ggcttgagtg gatgggatgg atcaaccctc tgagtggtga gacaaactat     180

gcacagaagt ttcagggcag ggtcaccatg accagggaca cgtccatcag cacagcctac     240

atggagctga gcaggctgag atctgacgac acggcggtgt actactgcgc cagagacacg     300

ggagaacttg acggaatgaa ctggtacttc gacctatggg ggagaggtac cttggtcacc     360
```

gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gcccccctagc 1080 agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 130
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag tccgactcct ggcctcctac ttttggcgga 300
gggaccaagg ttgagatcaa acgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 131
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 131

Arg Ala Ser Gln Ser Val Ser Ser Tyr Leu Ala
1 5 10

<210> SEQ ID NO 132
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 132

Asp Ala Ser Asn Arg Ala Thr
1 5

<210> SEQ ID NO 133
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 133

Gln Gln Ser Asp Ser Trp Pro Pro Thr
1 5

<210> SEQ ID NO 134
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Gly Tyr Tyr Met Thr
1 5

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

Asn Ile Asn Pro Asn Ser Gly Trp Thr Asn Tyr Ala Gln Lys Phe Gln
1 5 10 15

Gly

<210> SEQ ID NO 136
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 136

```
Asp Thr Gly Glu Leu Asp Gly Met Asn Trp Tyr Phe Asp Leu
1               5                   10


<210> SEQ ID NO 137
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105


<210> SEQ ID NO 138
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Gly Tyr
            20                  25                  30

Tyr Met Thr Trp Val Arg Gln Ala Pro Gly Gln Gly Leu Glu Trp Met
        35                  40                  45

Gly Asn Ile Asn Pro Asn Ser Gly Trp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120


<210> SEQ ID NO 139
<211> LENGTH: 214
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 139

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 140
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 140

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Gly Tyr
            20                  25                  30

Tyr Met Thr Trp Val Arg Gln Ala Pro Gly Gln Gly Leu Glu Trp Met
        35                  40                  45

Gly Asn Ile Asn Pro Asn Ser Gly Trp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110
```

```
Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 141
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 141
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag tccgactcct ggcctcctac ttttggcgga 300
gggaccaagg ttgagatcaa a 321

<210> SEQ ID NO 142
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 142
caggtgcagc tggtgcagtc tggggctgag gtgaagaagc ctggggcctc agtgaaggtc 60
tcctgcaagg cttctggata caccttccct ggctactata tgacttgggt gcgacaggcc 120
cctggacaag ggcttgagtg gatgggaaat atcaacccta acagtggttg gacaaactat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctca 369

<210> SEQ ID NO 143
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143
caggtgcagc tggtgcagtc tggggctgag gtgaagaagc ctggggcctc agtgaaggtc 60
tcctgcaagg cttctggata caccttccct ggctactata tgacttgggt gcgacaggcc 120
cctggacaag ggcttgagtg gatgggaaat atcaacccta acagtggttg gacaaactat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900

```
cagtacaaca gcacctaccg ggtggtgtcc gtgctgaccg tgctgcacca ggattggctg     960

aacggcaagg agtacaagtg taaggtgtcc aacaaggccc tgcctgcccc tatcgagaaa   1020

accatcagca aggccaaggg ccagcccaga gagccccagg tgtacaccct gccccctagc   1080

agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

cccccctgtgc tggacagcga tggcagcttc ttcctgtaca gcaagctgac cgtggacaag  1260

agcagatggc agcagggcaa cgtgttcagc tgctccgtga tgcacgaggc cctgcacaat   1320

cactacaccc agaagagcct gagcctgtcc cctggcaag                          1359
```

<210> SEQ ID NO 144
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

<210> SEQ ID NO 145
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 145

```
Arg Ala Ser Gln Ser Val Ser Ser Tyr Leu Ala
1               5                   10
```

<210> SEQ ID NO 146
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

```
Asp Ala Ser Asn Arg Ala Thr
```

1 5

<210> SEQ ID NO 147
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 147

Gln Gln Ser Asp Ser Trp Pro Pro Thr
1 5

<210> SEQ ID NO 148
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 148

Gly Tyr Tyr Met Ser
1 5

<210> SEQ ID NO 149
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 149

Trp Ile Asn Pro Gln Ser Gly Glu Thr Asn Tyr Ala Gln Lys Phe Gln
1 5 10 15

Gly

<210> SEQ ID NO 150
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 150

Asp Thr Gly Glu Leu Asp Gly Met Asn Trp Tyr Phe Asp Leu
1 5 10

<210> SEQ ID NO 151
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 151

Glu Ile Val Leu Thr Gln Ser Pro Ala Thr Leu Ser Leu Ser Pro Gly
1 5 10 15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105


<210> SEQ ID NO 152
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Trp Gly Tyr
            20                  25                  30

Tyr Met Ser Trp Val Arg Gln Ala Pro Gly Gln Gly Leu Glu Trp Met
        35                  40                  45

Gly Trp Ile Asn Pro Gln Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120


<210> SEQ ID NO 153
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 154
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Trp Gly Tyr
            20                  25                  30

Tyr Met Ser Trp Val Arg Gln Ala Pro Gly Gln Gly Leu Glu Trp Met
        35                  40                  45

Gly Trp Ile Asn Pro Gln Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 155
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 155

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa a                                              321
```

<210> SEQ ID NO 156
<211> LENGTH: 369
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic polynucleotide"

<400> SEQUENCE: 156
caggtgcagc tggtgcagtc tggggctgag gtgaagaagc ctggggcctc agtgaaggtc 60
tcctgcaagg cttctggata caccttctgg ggctactata tgagttgggt gcgacaggcc 120
cctggacaag ggcttgagtg gatgggatgg atcaaccctc agagtggtga gacaaactat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctca 369

<210> SEQ ID NO 157
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 157
caggtgcagc tggtgcagtc tggggctgag gtgaagaagc ctggggcctc agtgaaggtc 60
tcctgcaagg cttctggata caccttctgg ggctactata tgagttgggt gcgacaggcc 120
cctggacaag ggcttgagtg gatgggatgg atcaaccctc agagtggtga gacaaactat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gccccctagc 1080
agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 158
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 158
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag tccgactcct ggcctcctac ttttggcgga 300
gggaccaagg ttgagatcaa acgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 159
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 159

Arg Ala Ser Gln Ser Val Ser Ser Tyr Leu Ala
1 5 10

<210> SEQ ID NO 160
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 160

Asp Ala Ser Asn Arg Ala Thr
1 5

<210> SEQ ID NO 161
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 161

Gln Gln Ser Asp Ser Trp Pro Pro Thr
1 5

<210> SEQ ID NO 162
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 162

```
Gly Tyr Tyr Met Ser
1               5
```

<210> SEQ ID NO 163
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 163

```
Trp Ile Asn Pro Met Ser Gly Glu Thr Asn Tyr Ala Gln Lys Phe Gln
1               5                   10                  15

Gly
```

<210> SEQ ID NO 164
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 164

```
Asp Thr Gly Glu Leu Asp Gly Met Asn Trp Tyr Phe Asp Leu
1               5                   10
```

<210> SEQ ID NO 165
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 165

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys
            100                 105
```

<210> SEQ ID NO 166
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 166

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Tyr Met Ser Trp Val Arg Gln Ala Pro Gly Gln Gly Leu Glu Trp Met
        35                  40                  45

Gly Trp Ile Asn Pro Met Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser
        115                 120
```

<210> SEQ ID NO 167
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 167

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 168
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Gly Tyr
            20                  25                  30

Tyr Met Ser Trp Val Arg Gln Ala Pro Gly Gln Gly Leu Glu Trp Met
        35                  40                  45

Gly Trp Ile Asn Pro Met Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 169
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag tccgactcct ggcctcctac ttttggcgga    300

gggaccaagg ttgagatcaa a                                              321
```

<210> SEQ ID NO 170
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170

```
caggtgcagc tggtgcagtc tggggctgag gtgaagaagc ctggggcctc agtgaaggtc     60

tcctgcaagg cttctggata caccttccgt ggctactata tgagttgggt gcgacaggcc    120

cctggacaag ggcttgagtg gatgggatgg atcaacccta tgagtggtga gacaaactat    180

gcacagaagt ttcagggcag ggtcaccatg accagggaca cgtccatcag cacagcctac    240

atggagctga gcaggctgag atctgacgac acggcggtgt actactgcgc cagagacacg    300

ggagaacttg acggaatgaa ctggtacttc gacctatggg ggagaggtac cttggtcacc    360
```

gtctcctca 369

<210> SEQ ID NO 171
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 171
caggtgcagc tggtgcagtc tggggctgag gtgaagaagc ctggggcctc agtgaaggtc 60
tcctgcaagg cttctggata caccttccgt ggctactata tgagttgggt gcgacaggcc 120
cctggacaag ggcttgagtg gatgggatgg atcaacccta tgagtggtga gacaaactat 180
gcacagaagt ttcagggcag ggtcaccatg accagggaca cgtccatcag cacagcctac 240
atggagctga gcaggctgag atctgacgac acggcggtgt actactgcgc cagagacacg 300
ggagaacttg acggaatgaa ctggtacttc gacctatggg ggagaggtac cttggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gccccctagc 1080
agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 172
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 172
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240

```
gaagattttg cagtttatta ctgtcagcag tccgactcct ggcctcctac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642


<210> SEQ ID NO 173
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gln Ala Ser Gln Asp Ile Ser Asn Tyr Leu Asn
1               5                   10


<210> SEQ ID NO 174
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Asp Ala Ser Asn Leu Glu Thr
1               5


<210> SEQ ID NO 175
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Gln Gln Ala Asp Ile Phe Pro Leu Thr
1               5


<210> SEQ ID NO 176
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Ser Tyr Ala Ile Ser
1               5


<210> SEQ ID NO 177
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Gly Ile Ile Pro Val Phe Gly Ser Ala Tyr Tyr Ala Gln Lys Phe Gln
1               5                   10                  15

Gly


<210> SEQ ID NO 178
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Glu Gly Arg Ala Tyr Tyr Gly Ser Glu Ser Tyr Asp Asp Ser Asp Tyr
1               5                   10                  15

Met Asp Val


<210> SEQ ID NO 179
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Ile Phe Pro Leu
                85                  90                  95

Thr Phe Gly Gly Gly Thr Lys Val Glu Ile Lys
            100                 105


<210> SEQ ID NO 180
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Ser Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Gly Arg Ala Tyr Tyr Gly Ser Glu Ser Tyr Asp Asp Ser
            100                 105                 110

Asp Tyr Met Asp Val Trp Gly Lys Gly Thr Thr Val Thr Val Ser Ser
        115                 120                 125


<210> SEQ ID NO 181
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Ile Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 182
<211> LENGTH: 458
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 182

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Ser Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Gly Arg Ala Tyr Tyr Gly Ser Glu Ser Tyr Asp Asp Ser
            100                 105                 110

Asp Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Ala Gly Ala Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380
```

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 183
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183

gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatatta ctgtcagcag gccgatatct tccctctcac ttttggcgga    300

gggaccaagg ttgagatcaa a                                              321


<210> SEQ ID NO 184
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184

caggtgcagc tggtgcagtc tggggctgag gtgaagaagc ctgggtcctc ggtgaaggtc     60

tcctgcaagg cttctggagg caccttcagc tcgtacgcga tctcgtgggt gcgacaggcc    120

cctggacaag ggcttgagtg gatgggaggg atcatccccg tctttggctc ggcgtactac    180

gcgcagaagt tccagggcag agtcacgatt accgcggacg aatccacgag cacagcctac    240

atggagctga gcagcctgag atctgaggac acggcggtgt actactgcgc cggagaaggc    300

cgggcgtatt atgggtcgga gtcgtacgat gactctgact atatggacgt ctggggcaag    360

ggtacaactg tcaccgtctc ctca                                           384


<210> SEQ ID NO 185
<211> LENGTH: 1374
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 185

caggtgcagc tggtgcagtc tggggctgag gtgaagaagc ctgggtcctc ggtgaaggtc     60
```

```
tcctgcaagg cttctggagg caccttcagc tcgtacgcga tctcgtgggt gcgacaggcc    120

cctggacaag ggcttgagtg gatgggaggg atcatccccg tctttggctc ggcgtactac    180

gcgcagaagt tccagggcag agtcacgatt accgcggacg aatccacgag cacagcctac    240

atggagctga gcagcctgag atctgaggac acggcggtgt actactgcgc cggagaaggc    300

cgggcgtatt atgggtcgga gtcgtacgat gactctgact atatggacgt ctggggcaag    360

ggtacaactg tcaccgtctc ctcagccagc accaagggcc ccagcgtgtt ccccctggcc    420

cccagcagca agagcaccag cggcggcaca gccgccctgg gctgcctggt gaaggactac    480

ttccccgagc ccgtgaccgt gtcctggaac agcggagccc tgaccagcgg cgtgcacacc    540

ttccccgccg tgctgcagag cagcggcctg tacagcctga gcagcgtggt gaccgtgccc    600

agcagcagcc tgggcaccca gacctacatc tgtaacgtga accacaagcc cagcaacacc    660

aaggtggaca agaaggtgga gcccaagagc tgtgacaaga cccacacctg ccccccctgc    720

cctgcccccg agctggccgg agcccccagc gtgttcctgt tcccccccaa gcctaaggac    780

accctgatga tcagcagaac ccccgaggtg acctgtgtgg tggtggatgt gagccacgag    840

gaccctgagg tgaagttcaa ctggtacgtg gacggcgtgg aggtgcacaa tgccaagacc    900

aagcccaggg aggagcagta caacagcacc taccgggtgg tgtccgtgct gaccgtgctg    960

caccaggatt ggctgaacgg caaggagtac aagtgtaagg tgtccaacaa ggccctgcct   1020

gcccctatcg agaaaaccat cagcaaggcc aagggccagc ccagagagcc ccaggtgtac   1080

accctgcccc ctagcagaga tgagctgacc aagaaccagg tgtccctgac ctgcctggtg   1140

aagggcttct accccagcga catcgccgtg gagtgggaga gcaacggcca gcccgagaac   1200

aactacaaga ccaccccccc tgtgctggac agcgatggca gcttcttcct gtacagcaag   1260

ctgaccgtgg acaagagcag atggcagcag ggcaacgtgt tcagctgctc cgtgatgcac   1320

gaggccctgc acaatcacta cacccagaag agcctgagcc tgtcccctgg caag         1374
```

<210> SEQ ID NO 186
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 186

```
gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggaaacagg ggtcccatca    180

aggttcagtg gaagtggatc tgggacagat tttactttca ccatcagcag cctgcagcct    240

gaagatattg caacatatta ctgtcagcag gccgatatct tccctctcac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

cccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                       642
```

<210> SEQ ID NO 187
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

Gln Ala Ser Gln Asp Ile Ser Asn Tyr Leu Asn
1 5 10

<210> SEQ ID NO 188
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

Asp Ala Ser Asn Leu Ala Thr
1 5

<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Gln Gln Asp Asp Tyr Leu Pro Ile Thr
1 5

<210> SEQ ID NO 190
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Asp Phe Ala Ile Ser
1 5

<210> SEQ ID NO 191
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Gly Ile Ile Pro Ile Tyr Gly Thr Ala Ser Tyr Ala Gln Lys Phe Leu
1 5 10 15

Gly

<210> SEQ ID NO 192
<211> LENGTH: 14

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Asp Val Gly Val Gln Leu Val Tyr His Gly Ala Phe Asp Ile
1               5                   10


<210> SEQ ID NO 193
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asp Tyr Leu Pro Ile
                85                  90                  95

Thr Phe Gly Gly Gly Thr Lys Val Glu Ile Lys
            100                 105


<210> SEQ ID NO 194
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Phe
            20                  25                  30

Ala Ile Ser Trp Val Arg Gln Ala Pro Gly Gln Gly Leu Glu Trp Met
        35                  40                  45

Gly Gly Ile Ile Pro Ile Tyr Gly Thr Ala Ser Tyr Ala Gln Lys Phe
    50                  55                  60

Leu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Val Gln Leu Val Tyr His Gly Ala Phe Asp Ile
            100                 105                 110

Trp Gly Gln Gly Thr Met Val Thr Val Ser Ser
```

115 120

<210> SEQ ID NO 195
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 195

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Ala Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Asp Asp Tyr Leu Pro Ile
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 196
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 196

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asp Phe
20 25 30

Ala Ile Ser Trp Val Arg Gln Ala Pro Gly Gln Gly Leu Glu Trp Met
35 40 45

Gly Gly Ile Ile Pro Ile Tyr Gly Thr Ala Ser Tyr Ala Gln Lys Phe
50 55 60

```
Leu Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Val Gln Leu Val Tyr His Gly Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 197
<211> LENGTH: 321

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 197
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggcaacagg ggtcccatca 180
aggttcagtg gaagtggatc tgggacagat tttactttca ccatcagcag cctgcagcct 240
gaagatattg caacatatta ctgtcagcag gacgattacc tccctatcac ttttggcgga 300
gggaccaagg ttgagatcaa a 321

<210> SEQ ID NO 198
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 198
caggtgcagc tggtgcagtc tggggctgag gtgaagaagc ctgggtcctc ggtgaaggtc 60
tcctgcaagg cttctggagg caccttcagc gactttgcca tctcgtgggt gcgacaggcc 120
cctggacaag ggcttgagtg gatgggaggg atcattccca tctatggcac ggcgagctac 180
gcgcagaagt tcctaggcag agtcacgatt accgcggacg aatccacgag cacagcctac 240
atggagctga gcagcctgag atctgaggac acggcggtgt actactgcgc cagagatgtg 300
ggcgtccaac tcgtctatca cggggcgttc gacatctggg gtcagggtac aatggtcacc 360
gtctcctca 369

<210> SEQ ID NO 199
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 199
caggtgcagc tggtgcagtc tggggctgag gtgaagaagc ctgggtcctc ggtgaaggtc 60
tcctgcaagg cttctggagg caccttcagc gactttgcca tctcgtgggt gcgacaggcc 120
cctggacaag ggcttgagtg gatgggaggg atcattccca tctatggcac ggcgagctac 180
gcgcagaagt tcctaggcag agtcacgatt accgcggacg aatccacgag cacagcctac 240
atggagctga gcagcctgag atctgaggac acggcggtgt actactgcgc cagagatgtg 300
ggcgtccaac tcgtctatca cggggcgttc gacatctggg gtcagggtac aatggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600

```
acccagacct acatctgtaa cgtgaaccac aagcccagca acaccaaggt ggacaagaag    660

gtggagccca agagctgtga caagacccac acctgccccc cctgccctgc ccccgagctg    720

gccggagccc ccagcgtgtt cctgttcccc cccaagccta aggacaccct gatgatcagc    780

agaacccccg aggtgacctg tgtggtggtg gatgtgagcc acgaggaccc tgaggtgaag    840

ttcaactggt acgtggacgg cgtggaggtg cacaatgcca agaccaagcc cagggaggag    900

cagtacaaca gcacctaccg ggtggtgtcc gtgctgaccg tgctgcacca ggattggctg    960

aacggcaagg agtacaagtg taaggtgtcc aacaaggccc tgcctgcccc tatcgagaaa   1020

accatcagca aggccaaggg ccagcccaga gagccccagg tgtacaccct gcccccctagc   1080

agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

ccccctgtgc tggacagcga tggcagcttc ttcctgtaca gcaagctgac cgtggacaag   1260

agcagatggc agcagggcaa cgtgttcagc tgctccgtga tgcacgaggc cctgcacaat   1320

cactacaccc agaagagcct gagcctgtcc cctggcaag                          1359
```

```
<210> SEQ ID NO 200
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200

gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggcaacagg ggtcccatca    180

aggttcagtg gaagtggatc tgggacagat tttactttca ccatcagcag cctgcagcct    240

gaagatattg caacatatta ctgtcagcag gacgattacc tccctatcac ttttggcgga    300

gggaccaagg ttgagatcaa acgtacggtg gccgccccca gcgtgttcat cttccccccc    360

agcgatgagc agctgaagag cggcaccgcc agcgtggtgt gtctgctgaa caacttctac    420

ccccgggagg ccaaggtgca gtggaaggtg gacaatgccc tgcagagcgg caacagccag    480

gagagcgtga ccgagcagga cagcaaggac tccacctaca gcctgagcag caccctgacc    540

ctgagcaagg ccgactacga gaagcacaag gtgtacgcct gtgaggtgac ccaccagggc    600

ctgtccagcc ccgtgaccaa gagcttcaac cggggcgagt gc                        642
```

```
<210> SEQ ID NO 201
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Gln Ala Ser Gln Asp Ile Ser Asn Tyr Leu Asn
1               5                   10
```

```
<210> SEQ ID NO 202
<211> LENGTH: 7
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 202

Asp Ala Ser Asn Leu Ala Thr
1 5

<210> SEQ ID NO 203
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 203

Gln Gln Asp Asp Tyr Leu Pro Ile Thr
1 5

<210> SEQ ID NO 204
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 204

Ser Asp Ala Ile Ser
1 5

<210> SEQ ID NO 205
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 205

Gly Ile Ile Thr Asn Phe Gly Thr Ala Thr Tyr Ala Gln Lys Phe Gln
1 5 10 15

Gly

<210> SEQ ID NO 206
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 206

Asp Val Gly Val Gln Leu Val Tyr His Gly Ala Phe Asp Ile
1 5 10

<210> SEQ ID NO 207
<211> LENGTH: 123
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic polypeptide"

<400> SEQUENCE: 207

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asp
            20                  25                  30

Ala Ile Ser Trp Val Arg Gln Ala Pro Gly Gln Gly Leu Glu Trp Met
        35                  40                  45

Gly Gly Ile Ile Thr Asn Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Val Gln Leu Val Tyr His Gly Ala Phe Asp Ile
            100                 105                 110

Trp Gly Gln Gly Thr Met Val Thr Val Ser Ser
        115                 120
```

<210> SEQ ID NO 208
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 208

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asp Tyr Leu Pro Ile
                85                  90                  95

Thr Phe Gly Gly Gly Thr Lys Val Glu Ile Lys
            100                 105
```

<210> SEQ ID NO 209
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 209

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
```

20 25 30

Leu Asn Trp Tyr Gln Gln Lys Pro Gly Lys Ala Pro Lys Leu Leu Ile
35 40 45

Tyr Asp Ala Ser Asn Leu Ala Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Asp Asp Tyr Leu Pro Ile
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 210
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 210

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Asp
20 25 30

Ala Ile Ser Trp Val Arg Gln Ala Pro Gly Gln Gly Leu Glu Trp Met
35 40 45

Gly Gly Ile Ile Thr Asn Phe Gly Thr Ala Thr Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Val Gly Val Gln Leu Val Tyr His Gly Ala Phe Asp Ile
100 105 110

Trp Gly Gln Gly Thr Met Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 211
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 211

```
gacatccaga tgacccagtc tccatcctcc ctgtctgcat ctgtaggaga cagagtcacc     60

atcacttgcc aggcgagtca ggacattagc aactatttaa attggtatca gcagaaacca    120

gggaaagccc ctaagctcct gatctacgat gcatccaatt tggcaacagg ggtcccatca    180

aggttcagtg gaagtggatc tgggacagat tttactttca ccatcagcag cctgcagcct    240

gaagatattg caacatatta ctgtcagcag gacgattacc tccctatcac ttttggcgga    300
```

gggaccaagg ttgagatcaa a 321

<210> SEQ ID NO 212
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 212
caggtgcagc tggtgcagtc tggggctgag gtgaagaagc ctgggtcctc ggtgaaggtc 60
tcctgcaagg cttctggagg caccttcagc tccgacgcga tctcgtgggt gcgacaggcc 120
cctggacaag ggcttgagtg gatgggaggg atcatcacca actttgggac cgccacctac 180
gcgcagaagt tccaggggag agtcacgatt accgcggacg aatccacgag cacagcctac 240
atggagctga gcagcctgag atctgaggac acggcggtgt actactgcgc cagagatgtc 300
ggggtgcaac tggtctatca cggggcgttc gacatctggg gtcagggtac aatggtcacc 360
gtctcctca 369

<210> SEQ ID NO 213
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 213
caggtgcagc tggtgcagtc tggggctgag gtgaagaagc ctgggtcctc ggtgaaggtc 60
tcctgcaagg cttctggagg caccttcagc tccgacgcga tctcgtgggt gcgacaggcc 120
cctggacaag ggcttgagtg gatgggaggg atcatcacca actttgggac cgccacctac 180
gcgcagaagt tccaggggag agtcacgatt accgcggacg aatccacgag cacagcctac 240
atggagctga gcagcctgag atctgaggac acggcggtgt actactgcgc cagagatgtc 300
ggggtgcaac tggtctatca cggggcgttc gacatctggg gtcagggtac aatggtcacc 360
gtctcctcag ccagcaccaa gggccccagc gtgttccccc tggcccccag cagcaagagc 420
accagcggcg gcacagccgc cctgggctgc ctggtgaagg actacttccc cgagcccgtg 480
accgtgtcct ggaacagcgg agccctgacc agcggcgtgc acaccttccc cgccgtgctg 540
cagagcagcg gcctgtacag cctgagcagc gtggtgaccg tgcccagcag cagcctgggc 600
acccagacct acatctgtaa cgtgaaccac aagcccagca acaccaaggt ggacaagaag 660
gtggagccca agagctgtga caagacccac acctgccccc cctgccctgc ccccgagctg 720
gccggagccc ccagcgtgtt cctgttcccc cccaagccta aggacaccct gatgatcagc 780
agaacccccg aggtgacctg tgtggtggtg gatgtgagcc acgaggaccc tgaggtgaag 840
ttcaactggt acgtggacgg cgtggaggtg cacaatgcca agaccaagcc cagggaggag 900
cagtacaaca gcacctaccg ggtggtgtcc gtgctgaccg tgctgcacca ggattggctg 960
aacggcaagg agtacaagtg taaggtgtcc aacaaggccc tgcctgcccc tatcgagaaa 1020
accatcagca aggccaaggg ccagcccaga gagccccagg tgtacaccct gccccctagc 1080
agagatgagc tgaccaagaa ccaggtgtcc ctgacctgcc tggtgaaggg cttctacccc 1140
agcgacatcg ccgtggagtg ggagagcaac ggccagcccg agaacaacta caagaccacc 1200
ccccctgtgc tggacagcga tggcagcttc ttcctgtaca gcaagctgac cgtggacaag 1260
agcagatggc agcagggcaa cgtgttcagc tgctccgtga tgcacgaggc cctgcacaat 1320
cactacaccc agaagagcct gagcctgtcc cctggcaag 1359

<210> SEQ ID NO 214
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 214
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggcaacagg ggtcccatca 180
aggttcagtg gaagtggatc tgggacagat tttactttca ccatcagcag cctgcagcct 240
gaagatattg caacatatta ctgtcagcag gacgattacc tccctatcac ttttggcgga 300
gggaccaagg ttgagatcaa acgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 215
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Gln Ala Ser Gln Asp Ile Ser Asn Tyr Leu Asn
1               5                   10

<210> SEQ ID NO 216
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 216

Asp Ala Ser Asn Leu Ala Thr
1               5

<210> SEQ ID NO 217
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 217

Gln Gln Asp Asp Tyr Leu Pro Ile Thr
1 5

<210> SEQ ID NO 218
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 218

Glu Ser Ala Ile Ser
1 5

<210> SEQ ID NO 219
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 219

Gly Ile Ile Pro Thr Phe Asp Thr Thr Asn Tyr Ala Gln Lys Phe Gln
1 5 10 15

Gly

<210> SEQ ID NO 220
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 220

Asp Val Gly Val Gln Leu Val Tyr His Gly Ala Phe Asp Ile
1 5 10

<210> SEQ ID NO 221
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 221

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Ala Thr Gly Val Pro Ser Arg Phe Ser Gly
50 55 60

```
Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asp Tyr Leu Pro Ile
                85                  90                  95

Thr Phe Gly Gly Gly Thr Lys Val Glu Ile Lys
            100                 105
```

<210> SEQ ID NO 222
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 222

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Glu Ser
            20                  25                  30

Ala Ile Ser Trp Val Arg Gln Ala Pro Gly Gln Gly Leu Glu Trp Met
        35                  40                  45

Gly Gly Ile Ile Pro Thr Phe Asp Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Val Gln Leu Val Tyr His Gly Ala Phe Asp Ile
            100                 105                 110

Trp Gly Gln Gly Thr Met Val Thr Val Ser Ser
        115                 120
```

<210> SEQ ID NO 223
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 223

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asp Tyr Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 224
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Glu Ser
            20                  25                  30

Ala Ile Ser Trp Val Arg Gln Ala Pro Gly Gln Gly Leu Glu Trp Met
        35                  40                  45

Gly Gly Ile Ile Pro Thr Phe Asp Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Gly Val Gln Leu Val Tyr His Gly Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255
```

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 225
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225

gacatccaga tgacccagtc tccatcctcc ctgtctgcat ctgtaggaga cagagtcacc      60

atcacttgcc aggcgagtca ggacattagc aactatttaa attggtatca gcagaaacca     120

gggaaagccc ctaagctcct gatctacgat gcatccaatt tggcaacagg ggtcccatca     180

aggttcagtg gaagtggatc tgggacagat tttactttca ccatcagcag cctgcagcct     240

gaagatattg caacatatta ctgtcagcag gacgattacc tccctatcac ttttggcgga     300

gggaccaagg ttgagatcaa a                                               321


<210> SEQ ID NO 226
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226

caggtgcagc tggtgcagtc tggggctgag gtgaagaagc ctgggtcctc ggtgaaggtc      60

tcctgcaagg cttctggagg caccttcagc gagtccgcga tttcgtgggt gcgacaggcc     120
```

```
cctggacaag ggcttgagtg gatgggaggg atcatcccga cctttgacac caccaactac    180

gcgcagaagt tccaggggag agtcacgatt accgcggacg aatccacgag cacagcctac    240

atggagctga gcagcctgag atctgaggac acggcggtgt actactgcgc cagagatgtc    300

ggggtgcaac tggtctacca cggcgcgttc gacatctggg gtcagggtac aatggtcacc    360

gtctcctca                                                            369


<210> SEQ ID NO 227
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227

caggtgcagc tggtgcagtc tggggctgag gtgaagaagc ctgggtcctc ggtgaaggtc     60

tcctgcaagg cttctggagg caccttcagc gagtccgcga tttcgtgggt gcgacaggcc    120

cctggacaag ggcttgagtg gatgggaggg atcatcccga cctttgacac caccaactac    180

gcgcagaagt tccaggggag agtcacgatt accgcggacg aatccacgag cacagcctac    240

atggagctga gcagcctgag atctgaggac acggcggtgt actactgcgc cagagatgtc    300

ggggtgcaac tggtctacca cggcgcgttc gacatctggg gtcagggtac aatggtcacc    360

gtctcctcag ccagcaccaa gggccccagc gtgttccccc tggcccccag cagcaagagc    420

accagcggcg gcacagccgc cctgggctgc ctggtgaagg actacttccc cgagcccgtg    480

accgtgtcct ggaacagcgg agccctgacc agcggcgtgc acaccttccc cgccgtgctg    540

cagagcagcg gcctgtacag cctgagcagc gtggtgaccg tgcccagcag cagcctgggc    600

acccagacct acatctgtaa cgtgaaccac aagcccagca acaccaaggt ggacaagaag    660

gtggagccca agagctgtga caagacccac acctgccccc cctgccctgc ccccgagctg    720

gccggagccc ccagcgtgtt cctgttcccc cccaagccta aggacaccct gatgatcagc    780

agaacccccg aggtgacctg tgtggtggtg gatgtgagcc acgaggaccc tgaggtgaag    840

ttcaactggt acgtggacgg cgtggaggtg cacaatgcca agaccaagcc cagggaggag    900

cagtacaaca gcacctaccg ggtggtgtcc gtgctgaccg tgctgcacca ggattggctg    960

aacggcaagg agtacaagtg taaggtgtcc aacaaggccc tgcctgcccc tatcgagaaa   1020

accatcagca aggccaaggg ccagcccaga gagccccagg tgtacaccct gccccctagc   1080

agagatgagc tgaccaagaa ccaggtgtcc ctgacctgcc tggtgaaggg cttctacccc   1140

agcgacatcg ccgtggagtg ggagagcaac ggccagcccg agaacaacta caagaccacc   1200

ccccctgtgc tggacagcga tggcagcttc ttcctgtaca gcaagctgac cgtggacaag   1260

agcagatggc agcagggcaa cgtgttcagc tgctccgtga tgcacgaggc cctgcacaat   1320

cactacaccc agaagagcct gagcctgtcc cctggcaag                          1359


<210> SEQ ID NO 228
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 228
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggcaacagg ggtcccatca 180
aggttcagtg gaagtggatc tgggacagat tttactttca ccatcagcag cctgcagcct 240
gaagatattg caacatatta ctgtcagcag gacgattacc tccctatcac ttttggcgga 300
gggaccaagg ttgagatcaa acgtacggtg gccgccccca gcgtgttcat cttccccccc 360
agcgatgagc agctgaagag cggcaccgcc agcgtggtgt gtctgctgaa caacttctac 420
ccccgggagg ccaaggtgca gtggaaggtg gacaatgccc tgcagagcgg caacagccag 480
gagagcgtga ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac cggggcgagt gc 642

<210> SEQ ID NO 229
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 229
gagatcgtgc tgacccagag ccctgcaacc ctgtccctga gccctggcga aagggccact 60
ctgagctgca gggccagcca gagcgtgagc agctacctcg cctggtacca gcagaagccc 120
ggccaggccc ctaggctgct gatctacgac gccagcaaca gggccaccgg cattcccgca 180
aggttcagcg gcagcggcag cggcaccgac ttcaccctga ccatcagcag cctggagccc 240
gaagacttcg cagtctacta ctgccagcag agcgacagct ggccccccac cttcgggggc 300
ggcaccaagg tggagatcaa gagggctgac gcggcgccca ccgtgagcat cttccccccc 360
agcagcgagc agctgactag cggcggagcc tctgtggtgt gcttcctgaa caacttctac 420
cccaaggaca tcaacgtgaa gtggaagatc gacggcagcg agaggcagaa cggagtcctc 480
aacagctgga ccgaccagga cagcaaggat agcacctaca gcatgagcag caccctgacc 540
ctgaccaagg acgagtacga gaggcacaac agctacacct gcgaagccac ccacaaaacc 600
tccaccagcc ccatcgtgaa gagcttcaat aggaacgagt gc 642

<210> SEQ ID NO 230
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 230

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 231
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 231

```
caggtgcagc tcgtgcagag cggcgccgag gtgaaaaagc ccggcgcctc tgtcaaggtg     60

agctgcaagg ccagcggcta caccttcctg ggctactaca tgagctgggt gaggcaggct    120

cccggacagg gcctggagtg gatgggctgg atcaaccccc tgagcggcga gaccaactac    180

gcccagaagt tccagggcag ggtgaccatg accagggaca ccagcatcag caccgcctac    240

atggaactga gcaggctgag gagcgacgac accgccgtgt attactgcgc cagggacacc    300

ggcgagctgg acggcatgaa ctggtacttc gacctgtggg gcaggggcac cctggtgaca    360

gtgagcagcg ctaaaaccac cgccccctcc gtgtaccccc tggcgcccgt ctgtggcgac    420

accaccggca gcagcgtgac actgggctgc ctggtgaagg gctacttccc cgagcccgtc    480

accctgacct ggaatagcgg aagcctgtca agcggcgtgc acactttccc cgccgtgctg    540

cagtctgacc tgtacaccct gagcagcagc gtgaccgtga ccagcagcac ctggcccagc    600

cagtctatca cttgcaacgt ggcccaccct gccagctcca ccaaggtgga caagaagatc    660

gagcctaggg gacccaccat taaaccctgc ccccctgca agtgccccgc ccccaatctg    720

gccggagccc ccagcgtgtt tatcttcccc cccaagatca aggacgtgct gatgatcagc    780

ctgagcccca tcgtgacctg cgtggtggtg gacgtgagcg aggacgaccc agacgtgcag    840

atcagctggt ttgtgaacaa cgtggaggtg cacaccgccc agacccagac ccacagggag    900

gattacaaca gcaccctgag ggtggtgagc gccctgccca tccagcacca ggactggatg    960

tccggcaagg agttcaagtg caaggtgaac aacaaggacc tgcccgcccc catcgagagg   1020
```

```
accatcagca agcctaaggg cagcgtgagg gcaccccagg tctacgtgct gcccccccca   1080

gaggaggaaa tgaccaagaa gcaggtgacc ctgacctgca tggtgaccga cttcatgccc   1140

gaggacatct acgtggagtg gaccaacaac ggcaagaccg agctgaacta caagaacacc   1200

gagcccgtgc tggacagcga cggcagctac ttcatgtata gcaagctgcg ggtcgagaag   1260

aagaactggg tggagaggaa cagctacagc tgcagcgtcg tgcacgaagg cctccacaac   1320

caccacacca ccaagagctt cagcaggacc cccgggaag                          1359
```

<210> SEQ ID NO 232
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 232

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Leu Gly Tyr
            20                  25                  30

Tyr Met Ser Trp Val Arg Gln Ala Pro Gly Gln Gly Leu Glu Trp Met
        35                  40                  45

Gly Trp Ile Asn Pro Leu Ser Gly Glu Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Leu Asp Gly Met Asn Trp Tyr Phe Asp Leu
            100                 105                 110

Trp Gly Arg Gly Thr Leu Val Thr Val Ser Ser Ala Lys Thr Thr Ala
        115                 120                 125

Pro Ser Val Tyr Pro Leu Ala Pro Val Cys Gly Asp Thr Thr Gly Ser
    130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Thr Ser Ser Thr Trp Pro Ser Gln Ser Ile Thr Cys Asn Val Ala
        195                 200                 205

His Pro Ala Ser Ser Thr Lys Val Asp Lys Lys Ile Glu Pro Arg Gly
    210                 215                 220

Pro Thr Ile Lys Pro Cys Pro Pro Cys Lys Cys Pro Ala Pro Asn Leu
225                 230                 235                 240

Ala Gly Ala Pro Ser Val Phe Ile Phe Pro Pro Lys Ile Lys Asp Val
                245                 250                 255

Leu Met Ile Ser Leu Ser Pro Ile Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
```

290 295 300

Thr Leu Arg Val Val Ser Ala Leu Pro Ile Gln His Gln Asp Trp Met
305 310 315 320

Ser Gly Lys Glu Phe Lys Cys Lys Val Asn Asn Lys Asp Leu Pro Ala
325 330 335

Pro Ile Glu Arg Thr Ile Ser Lys Pro Lys Gly Ser Val Arg Ala Pro
340 345 350

Gln Val Tyr Val Leu Pro Pro Pro Glu Glu Glu Met Thr Lys Lys Gln
355 360 365

Val Thr Leu Thr Cys Met Val Thr Asp Phe Met Pro Glu Asp Ile Tyr
370 375 380

Val Glu Trp Thr Asn Asn Gly Lys Thr Glu Leu Asn Tyr Lys Asn Thr
385 390 395 400

Glu Pro Val Leu Asp Ser Asp Gly Ser Tyr Phe Met Tyr Ser Lys Leu
405 410 415

Arg Val Glu Lys Lys Asn Trp Val Glu Arg Asn Ser Tyr Ser Cys Ser
420 425 430

Val Val His Glu Gly Leu His Asn His His Thr Thr Lys Ser Phe Ser
435 440 445

Arg Thr Pro Gly Lys
450

<210> SEQ ID NO 233
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 233

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Leu Gly Tyr
20 25 30

Tyr Met Ser Trp Val Arg Gln Ala Pro Gly Gln Gly Leu Glu Trp Met
35 40 45

Gly Trp Ile Asn Pro Leu Ser Gly Glu Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Thr Gly Glu Leu Asp Gly Met Asn Trp Tyr Phe Asp Leu
100 105 110

Trp Gly Arg Gly Thr Leu Val Thr Val Ser Ser Ala Gln Thr Thr Ala
115 120 125

Pro Ser Val Tyr Pro Leu Ala Pro Gly Cys Gly Asp Thr Thr Ser Ser
130 135 140

Thr Val Thr Leu Gly Cys Leu Val Lys Gly Tyr Phe Pro Glu Pro Val
145 150 155 160

Thr Val Thr Trp Asn Ser Gly Ala Leu Ser Ser Asp Val His Thr Phe
165 170 175

Pro Ala Val Leu Gln Ser Gly Leu Tyr Thr Leu Thr Ser Ser Val Thr
180 185 190

Ser Ser Thr Trp Pro Ser Gln Thr Val Thr Cys Asn Val Ala His Pro
195 200 205

Ala Ser Ser Thr Lys Val Asp Lys Lys Val Glu Arg Arg Asn Gly Gly
210 215 220

Ile Gly His Lys Cys Pro Thr Cys Pro Thr Cys His Lys Cys Pro Val
225 230 235 240

Pro Glu Leu Ala Gly Ala Pro Ser Val Phe Ile Phe Pro Pro Lys Pro
245 250 255

Lys Asp Ile Leu Leu Ile Ser Gln Asn Ala Lys Val Thr Cys Val Val
260 265 270

Val Asp Val Ser Glu Glu Glu Pro Asp Val Gln Phe Ser Trp Phe Val
275 280 285

Asn Asn Val Glu Val His Thr Ala Gln Thr Gln Pro Arg Glu Glu Gln
290 295 300

Tyr Asn Ser Thr Phe Arg Val Val Ser Ala Leu Pro Ile Gln His Gln
305 310 315 320

Asp Trp Met Ser Gly Lys Glu Phe Lys Cys Lys Val Asn Asn Lys Ala
325 330 335

Leu Pro Ser Pro Ile Glu Lys Thr Ile Ser Lys Pro Lys Gly Leu Val
340 345 350

Arg Lys Pro Gln Val Tyr Val Met Gly Pro Pro Thr Glu Gln Leu Thr
355 360 365

Glu Gln Thr Val Ser Leu Thr Cys Leu Thr Ser Gly Phe Leu Pro Asn
370 375 380

Asp Ile Gly Val Glu Trp Thr Ser Asn Gly His Ile Glu Lys Asn Tyr
385 390 395 400

Lys Asn Thr Glu Pro Val Met Asp Ser Asp Gly Ser Phe Phe Met Tyr
405 410 415

Ser Lys Leu Asn Val Glu Arg Ser Arg Trp Asp Ser Arg Ala Pro Phe
420 425 430

Val Cys Ser Val Val His Glu Gly Leu His Asn His His Val Glu Lys
435 440 445

Ser Ile Ser Arg Pro Pro Gly Lys
450 455

<210> SEQ ID NO 234
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 234

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

```
Glu Asp Phe Ala Val Tyr Tyr Cys Gln Gln Ser Asp Ser Trp Pro Pro
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210
```

<210> SEQ ID NO 235
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 235

```
gagatcgtgc tgacccagag ccctgcaacc ctgtccctga gccctggcga aagggccact     60

ctgagctgca gggccagcca gagcgtgagc agctacctcg cctggtacca gcagaagccc    120

ggccaggccc ctaggctgct gatctacgac gccagcaaca gggccaccgg cattcccgca    180

aggttcagcg gcagcggcag cggcaccgac ttcaccctga ccatcagcag cctggagccc    240

gaagacttcg cagtctacta ctgccagcag agcgacagct ggcccccac cttcgggggc     300

ggcaccaagg tggagatcaa gagggccgac gcggcgccca ccgtgtccat cttccccccc    360

agcaccgaac agctggccac tggcggagct agcgtggtgt gcctgatgaa caacttctac    420

cccagggaca tcagcgtgaa gtggaagatc gacggcaccg agaggaggga cggcgtcctg    480

gattctgtga ccgaccagga cagcaaagac agcacctaca gcatgagcag caccctgagc    540

ctgaccaagg ccgactacga gagccacaac ctctacacct gcgaggtggt gcacaagacc    600

agcagcagcc ccgtggtgaa gagcttcaac aggaacgagt gc                        642
```

<210> SEQ ID NO 236
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 236

```
caggtgcagc tcgtgcagag cggcgccgag gtgaaaaagc ccggcgcctc tgtcaaggtg     60

agctgcaagg ccagcggcta caccttcctg ggctactaca tgagctgggt gaggcaggct    120

cccggacagg gcctggagtg gatgggctgg atcaaccccc tgagcggcga gaccaactac    180
```

```
gcccagaagt tccagggcag ggtgaccatg accagggaca ccagcatcag caccgcctac    240

atggaactga gcaggctgag gagcgacgac accgccgtgt attactgcgc cagggacacc    300

ggcgagctgg acggcatgaa ctggtacttc gacctgtggg gcaggggcac cctggtgaca    360

gtgagcagcg cccagaccac agctcccagc gtgtatcccc tggcgcccgg ctgtggcgat    420

actaccagca gcaccgtcac cctgggctgc ctggtgaaag gctacttccc cgaaccagtg    480

accgtgacct ggaatagcgg agctctgtca agcgacgtgc acacctttcc cgccgtgctc    540

cagagcggcc tgtacaccct caccagcagc gtgactagca gcacctggcc ctctcagacc    600

gtgacctgca acgtggccca ccccgcctct tccaccaagg tggacaagaa agtggagagg    660

aggaacggcg gaatcggcca caagtgccca acctgcccca cctgccataa atgccccgtg    720

cccgaactgg ccggagcccc cagcgtgttc atcttccccc ccaagcccaa ggacatcctg    780

ctgatcagcc agaacgccaa ggtgacctgc gtggtggtgg acgtcagcga ggaggagccc    840

gacgtgcagt tcagctggtt tgtgaacaac gtggaggtgc acaccgccca gacccagccc    900

agggaggagc agtacaacag caccttccgg gtggtgagcg ccctgcctat ccagcaccag    960

gactggatga gcggcaagga gttcaagtgc aaggtgaaca acaaggccct gcccagcccc   1020

atcgagaaga ccattagcaa gcccaagggc ctcgtgagga agccccaggt ctacgtgatg   1080

ggaccaccta ccgagcagct gaccgaacag accgtgtccc tgacctgcct gaccagcggc   1140

ttcctgccca acgacatcgg cgtggagtgg accagcaacg gccacatcga gaagaactac   1200

aagaacaccg agcccgtgat ggacagcgac ggcagcttct tcatgtacag caagctgaac   1260

gtggagagga gcaggtggga cagcagagcc cccttcgtgt gcagcgtcgt ccacgagggg   1320

ctgcacaacc accacgtcga gaagagcatc tctaggcccc ccggcaag                1368
```

```
<210> SEQ ID NO 237
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ala Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Thr Leu Pro Phe
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140
```

Ser Val Lys Trp Lys Ile Asp Gly Thr Glu Arg Arg Asp Gly Val Leu
145 150 155 160

Asp Ser Val Thr Asp Gln Asp Ser Lys Asp Ser Thr Tyr Ser Met Ser
165 170 175

Ser Thr Leu Ser Leu Thr Lys Ala Asp Tyr Glu Ser His Asn Leu Tyr
180 185 190

Thr Cys Glu Val Val His Lys Thr Ser Ser Ser Pro Val Val Lys Ser
195 200 205

Phe Asn Arg Asn Glu Cys
210

<210> SEQ ID NO 238
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 238

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Phe Gly Asp
20 25 30

Tyr Trp Ser Trp Ile Arg Gln Pro Pro Gly Lys Gly Leu Glu Trp Ile
35 40 45

Gly Glu Ile Asp Trp Ser Gly Ala Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Gly Ser Lys Glu Leu Ser Phe Asp Ile Trp Gly Gln Gly Thr
100 105 110

Met Val Thr Val Ser Ser Ala Gln Thr Thr Ala Pro Ser Val Tyr Pro
115 120 125

Leu Ala Pro Gly Cys Gly Asp Thr Thr Ser Ser Thr Val Thr Leu Gly
130 135 140

Cys Leu Val Lys Gly Tyr Phe Pro Glu Pro Val Thr Val Thr Trp Asn
145 150 155 160

Ser Gly Ala Leu Ser Ser Asp Val His Thr Phe Pro Ala Val Leu Gln
165 170 175

Ser Gly Leu Tyr Thr Leu Thr Ser Ser Val Thr Ser Ser Thr Trp Pro
180 185 190

Ser Gln Thr Val Thr Cys Asn Val Ala His Pro Ala Ser Ser Thr Lys
195 200 205

Val Asp Lys Lys Val Glu Arg Arg Asn Gly Gly Ile Gly His Lys Cys
210 215 220

Pro Thr Cys Pro Thr Cys His Lys Cys Pro Val Pro Glu Leu Ala Gly
225 230 235 240

Ala Pro Ser Val Phe Ile Phe Pro Pro Lys Pro Lys Asp Ile Leu Leu
245 250 255

Ile Ser Gln Asn Ala Lys Val Thr Cys Val Val Val Asp Val Ser Glu
260 265 270

Glu Glu Pro Asp Val Gln Phe Ser Trp Phe Val Asn Asn Val Glu Val

```
        275                 280                 285

His Thr Ala Gln Thr Gln Pro Arg Glu Glu Gln Tyr Asn Ser Thr Phe
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Ala Leu Pro Ser Pro Ile
                325                 330                 335

Glu Lys Thr Ile Ser Lys Pro Lys Gly Leu Val Arg Lys Pro Gln Val
            340                 345                 350

Tyr Val Met Gly Pro Pro Thr Glu Gln Leu Thr Glu Gln Thr Val Ser
        355                 360                 365

Leu Thr Cys Leu Thr Ser Gly Phe Leu Pro Asn Asp Ile Gly Val Glu
    370                 375                 380

Trp Thr Ser Asn Gly His Ile Glu Lys Asn Tyr Lys Asn Thr Glu Pro
385                 390                 395                 400

Val Met Asp Ser Asp Gly Ser Phe Phe Met Tyr Ser Lys Leu Asn Val
                405                 410                 415

Glu Arg Ser Arg Trp Asp Ser Arg Ala Pro Phe Val Cys Ser Val Val
            420                 425                 430

His Glu Gly Leu His Asn His His Val Glu Lys Ser Ile Ser Arg Pro
        435                 440                 445

Pro Gly Lys
    450
```

<210> SEQ ID NO 239
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 239

```
caggtgcagc tgcagcagtg gggcgccgga ctgctgaagc ccagcgagac cctgagcctg      60

acctgcgccg tgtacggcgg gtccttcttc ggcgactact ggagctggat caggcagccc     120

cccggcaaag gcctggagtg gatcggcgag atcgactgga gcggcgccac caactacaac     180

cccagcctca agagcagggt gaccatcagc gtggacacca gcaagaacca gttcagcctg     240

aagctgagca gcgtgaccgc cgccgacacc gccgtgtact attgcgccag gggcggcagc     300

aaggagctga gcttcgacat ctggggccag ggcactatgg tcaccgtgag cagcgcccag     360

accacagctc ccagcgtgta tcccctggcg cccggctgtg gcgatactac cagcagcacc     420

gtcaccctgg gctgcctggt gaaaggctac ttccccgaac cagtgaccgt gacctggaat     480

agcggagctc tgtcaagcga cgtgcacacc tttcccgccg tgctccagag cggcctgtac     540

accctcacca gcagcgtgac tagcagcacc tggccctctc agaccgtgac ctgcaacgtg     600

gcccaccccg cctcttccac caaggtggac aagaaagtgg agaggaggaa cggcggaatc     660

ggccacaagt gcccaacctg ccccacctgc cataaatgcc ccgtgcccga actggccgga     720

gcccccagcg tgttcatctt cccccccaag cccaaggaca tcctgctgat cagccagaac     780

gccaaggtga cctgcgtggt ggtggacgtc agcgaggagg agcccgacgt gcagttcagc     840

tggtttgtga acaacgtgga ggtgcacacc gcccagaccc agcccaggga ggagcagtac     900

aacagcacct tccgggtggt gagcgccctg cctatccagc accaggactg gatgagcggc     960
```

-continued

```
aaggagttca agtgcaaggt gaacaacaag gccctgccca gccccatcga gaagaccatt   1020

agcaagccca agggcctcgt gaggaagccc caggtctacg tgatgggacc acctaccgag   1080

cagctgaccg aacagaccgt gtccctgacc tgcctgacca gcggcttcct gcccaacgac   1140

atcggcgtgg agtggaccag caacggccac atcgagaaga actacaagaa caccgagccc   1200

gtgatggaca gcgacggcag cttcttcatg tacagcaagc tgaacgtgga gaggagcagg   1260

tgggacagca gagccccctt cgtgtgcagc gtcgtccacg aggggctgca caaccaccac   1320

gtcgagaaga gcatctctag gcccccggc aag                                1353


<210> SEQ ID NO 240
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 240

gacatccaga tgactcagtc cccctctagc ctgagcgcta gcgtgggcga cagggtgacc     60

atcacctgcc aggccagcca ggacatcgcc aactacctga actggtacca gcagaagccc    120

ggcaaggccc ccaaactgct gatctacgac gcctcaaacc tcgagaccgg cgtgcctagc    180

aggtttagcg gcagcggcag cggcaccgac ttcaccttca ccatcagcag cctgcagccc    240

gaggatatcg ccacctacta ctgccagcag gccgacaccc tgcccttcac cttcggcgga    300

ggcaccaagg tggagattaa gagggccgac gcggcgccca ccgtgtccat cttcccccc     360

agcaccgaac agctggccac tggcggagct agcgtggtgt gcctgatgaa caacttctac    420

cccagggaca tcagcgtgaa gtggaagatc gacggcaccg agaggaggga cggcgtcctg    480

gattctgtga ccgaccagga cagcaaagac agcacctaca gcatgagcag caccctgagc    540

ctgaccaagg ccgactacga gagccacaac ctctacacct gcgaggtggt gcacaagacc    600

agcagcagcc ccgtggtgaa gagcttcaac aggaacgagt gc                       642
```

ANTIGEN BINDING PROTEIN

CROSS REFERENCE TO RELATED APPLICATION

This application is a 371 of International Application No. PCT/IB2021/056925 filed Jul. 29, 2021, which claims the benefit of U.S. Provisional Application No. 63/059,387 filed Jul. 31, 2020, the disclosures of which are incorporated herein in their entireties.

SEQUENCE LISTING

The instant application contains a Sequence Listing which has been submitted electronically in ASCII format and is hereby incorporated by reference in its entirety. Said ASCII copy, created on Jul. 6, 2021, is named PU66960_SL.txt and is 265,335 bytes in size.

FIELD OF THE INVENTION

The invention relates to antigen binding proteins that specifically bind to BMP1, TLL1 and/or TLL2, and pharmaceutical compositions and uses thereof. The invention also relates to pharmaceutical compositions containing the antigen binding proteins and uses thereof.

BACKGROUND OF THE INVENTION

Fibrous collagens are integral parts of the extracellular matrix that support tissue integrity and maintain the cellular microenvironment for normal physiological functions. Collagens 1-Ill, the major isoforms of the fibrous collagen protein family, are synthesized as procollagen precursors containing N-terminal and C-terminal propeptides. The procollagens are post-translationally modified by proline hydroxylation, and secreted into the peri-vascular space for further processing. N-terminal propeptides of the collagens are subsequently cleaved by proteinases of the ADAMTS (A Distintegrin And Metalloproteinase with ThromboSpondin repeats) family, while the C-terminal propeptides are processed by the Tolloid family of metalloproteases, which include BMP1 (bone morphogenetic protein 1), TLL1 (tolloid-like 1) and TLL2 (tolloid-like 2) (Hopkins, D. R. et al., Matrix Biology, 2007, 26, 508-523). The cleavage of both N-terminal and C-terminal propeptides allows further maturation of the collagen, leading to cross-linking at lysine residues and formation of insoluble fibrillar structures (Shoulders, M. D. et al., Annual Review of Biochemistry, 2009, 78, 929-958).

Whereas the BMP1, TLL1 and TLL2 proteins are encoded by separate genes, this family also includes isoforms of BMP1, including multiple isofoms of BMP1 that result from alternative splicing of the same gene product (see e.g., Takahara, K., et al., The Journal of Biological Chemistry, 1994, 269. 32572-32578; and Cvetjeticanin, B. et al., Medical Hypotheses, 2014, 83, 656-658). The originally discovered form of BMP1 is designated BMP-1-1 or BMP1-1. Other BMP1 isoforms encoded by splice variant RNA transcripts have been described at the transcriptional level and designated with sequential suffixes, e.g., as BMP-1-2, BMP-1-3, BMP-1-4, BMP-1-5, BMP-1-6, and BMP-1-7 (see, e.g., Wozney et al., Science (1988), 242: 1528-1534; Kessler et al., Science, (1996) 271: 360-362; Li et al., Proc. Natl. Acad. Sci. USA (1996), 93: 5127-5130; Janitz et al., J. Mol. Med. (1998), 76: 141-146; Takahara et al., J. Biol. Chem. (1994), 269: 32572-32578; and Ge and Greenspan, Birth Defect Res. (2006), 78: 47-68).

A number of BMP1 isoforms have also been confirmed at the protein level as circulating in the blood of patients with various diseases and in healthy humans (see, e.g., International Patent publication Nos. WO 2008/011193 and WO 2013/163479, and Grgurevic et al., J. Am. Soc. Nephrol. (2011), 21:681-692). In addition, the role of BMP1 in processing procollagen leading to fibrosis and scar tissue in a variety of diseases as well as the discovery of blood profiles comprising individual BMP1 isoforms in patients with various diseases has made BMP1 an attractive target for developing new therapies (see, e.g. WO 2008/011193; WO 2013/163479; Grgurevic et al., J. Am. Soc. Nephrol. (2011), 21:681-692, Cvetjeticanin, B. et al., Medical Hypotheses, 2014, 83, 656-658; and Turtle et al., Expert Opin. Ther. Patents (2004), 14(8): 1185-1197).

Excessive production of extracellular matrix (ECM) proteins, including collagen, can lead to fibrotic pathologies in various organs or tissues that may be associated with increased tissue rigidity, parenchymal replacement, aberrant electrical conductance, sclerotic wound healing (e.g. infarction and burns), and/or abnormal cell-cell interactions. For example, increased fibrosis and collagen production are consistently observed in patients with acute and chronic cardiac diseases, e.g., heart failure, arrhythmias, hypertrophic cardiomyopathy, and myocardial infarction (Lopez, B. et al., Circulation, 2010, 121, 1645-1654; Ho, C. Y., et al., New England Journal of Medicine, 2010, 363, 552-563; Kostin, S. et al., Cardiovascular Research, 2002, 54, 361-379; See, F. et al., Current Pharmaceutical Design, 2005, 11, 477-487; Cvetjeticanin, B. et al. Medical Hypotheses, 2014, 83, 656-658), chronic obstructive pulmonary disease ("COPD") (Salazar, L. M., et al., Lung, 2011, 189, 101-109), liver cirrhosis and nonalcoholic steatohepatitis ("NASH") (Bataller, R., et al., Journal of Clinical Investigation, 2005, 115, 209-218), idiopathic pulmonary fibrosis (Chakraborty, S, et al., Expert Opin Investig Drugs, 2014, 23, 893-910), collagen vascular diseases, e.g. systemic lupus erythematosus, rheumatoid arthritis and scleroderma (Eckes, B., et al., J Mol Med, 2014, 92, 913-924), muscular dystrophies (e.g., Serrano, A. C., et al., Experimental Cell Research, 2010, 316, 3050-3058; Klingler, W., et al., Acta Myoligica, XXXI, 2012, 184-195), chronic kidney disease (Liu, Y., Nature Reviews Nephrology, 2011, 7, 684-696), acute kidney injury (Molitoris, B., The Journal of clinical Investigation, 2014, 124, 2355-2363; Venkatachalam, M. A. et al., Am J Physiol Renal Physiol 298: F1078-F1094, 2010), diabetic nephropathy (Sun, Y. M., et al., Biochemical and Biophysical Research Communications, 2013, 433, 359-361), keloids, wound healing, adhesions, hypertrophic and other scarring associated with, e.g. burns, surgery and other trauma (Meier K., et al., Expert Opinion on Emerging Drugs, 2006, 11, 39-47; Malecaze, F., et al., Investigative Opthalmology and Visual Science, 2014, 55, 6712-6721; van der Weer, W. et al., Burns, 2009, 35, 15-29), and stroke, multiple sclerosis and spinal cord injury (Fernandez-Klett, F. and Piller, J. Brain Pathology, 2014, 24, 404-13; Rimar, D. et al., Arthritis & Rheumatology, Vol. 66, No. 3, March 2014, 726-730). Therefore, reducing excessive collagen production and maturation by targeting the BMP1, TLL1 and/or TLL2 pathway(s) can be an effective therapeutic strategy for treating fibrotic pathologies such as these diseases. This is supported by recent published studies using pharmacological agents that inhibit BMP1, TLL1 and/or TLL2 activity in cardiac and kidney disease models in small animals (Grgurevic, L, et al., Journal of the American Society of Nephrology, 2011, 21, 681-692; He, W., et al., Proceedings of the National Academy of Sciences, 2010, 107, 21110-21115; Cvetjeticanin, B. et al., Medical Hypotheses, 2014, 83, 656-658; International Patent publication nos. WO 2008/011193 and WO 2013/163479).

The Tolloid family of metalloproteases (BMP1, TLL1 and TLL2) has additional substrates beyond collagens that may also contribute to its role in promoting ECM protein production. For example, the pro-form of lysyl oxidase 1 (LOX1) has been shown to be a substrate of BMP1, and cleavage by BMP1 enhances the LOX enzyme activity and thereby induces collagen cross-linking (Uzel, M. I., et al., Journal of Biological Chemistry, 2001, 276, 22537-22543). Thus, BMP1 also has a role in the development of pathological tissue stiffness via this mechanism, for example in glaucoma (Tovar-Vidales, T., et al., Investigative Ophthalmology & Visual Science, 2013, 54, 4741-4748) and in diastolic dysfunction in the heart (Lopez, B., et al., American Journal of Physiology—Heart and Circulatory Physiology, 2010, 299, H1-H9). TGF-beta binding protein (LTBP) has also been shown to be cleaved by BMP1, allowing enhanced TGF-beta action to induce further collagen production (Ge, G., et al., Journal of Cell Biology, 2006, 175, 1 11-120). Regulation of TGF-beta by BMP1 may also play roles in other pathologies, such as control of cancer cell metastasis and invasion (Wu, X., et al. Oncogene, 2014, 33, 1506-1514). Similarly, BMP1, TLL1 and/or TLL2 also activate a broader range of other TGF-beta like molecules, such as BMPs 2 and 4, by proteolytically processing interacting proteins (Hopkins, D. R. et al., Matrix Biology, 2007, 26, 508-523). The combined actions of BMP1 and its various substrates suggest that BMP1, TLL1 and TLL2 are key regulators of tissue ECM production/maturation and that the members of the tolloid family of metalloproteases are particularly effective targets for anti-fibrosis therapeutic intervention. BMP1, TLL1 and TLL2 may also affect other biological pathways via additional substrate processing. In particular, they may affect muscle biology via promoting activation of myostatin. Myostatin is a hormone that negatively regulates muscle growth (Lee, S. J., 2004, Annual Review of Cell & Developmental Biology, 20, 61-86). BMP1 has been demonstrated to cleave an inhibitory propeptide of myostatin and thus enhance myostatin activity (Wolfman N. M., et al., Proceedings of the National Academy of Sciences, 2003, 100, 15842-15846). Knockout of TLL2 in mice demonstrated enhanced muscle mass, thereby providing support for the connection between tolloid metalloprotease and myostatin (Lee, S. J., PLoS one, 2008, 3, e1628). An inhibitor of BMP1, TLL1 and/or TLL2 could therefore be beneficial in diseases where muscle function or muscle mass is diminished, including muscular dystrophy, sarcopenia, and cachexia associated with, e.g., heart failure, CKD, COPD, cancer or old age.

Taken together, the biology of BMP1, TLL1 and TLL2 lends support for their key roles in collagen processing, assembly and cross-linking, leading to the formation of a fibrillar collagen network that maintains tissue integrity and proper cellular microenvironment. This family of proteins may also play important roles in the etiology of fibrotic conditions, for example in the heart, lung, skeletal muscle, kidney, liver, skin, vasculature, nervous system, and eye, and inhibitors of these metalloproteases may provide broad benefits as anti-fibrotic agents for the treatment of diseases associated with fibrosis, such as myocardial infarction, heart failure, cardiac arrhythmias, hypertrophic cardiomyopathy, chronic kidney disease (CKD), post-acute kidney injury, diabetic nephropathy, delayed graft function post-transplantation, chronic obstructive pulmonary disease (COPD), idiopathic pulmonary fibrosis (IPF), liver cirrhosis, nonalcoholic steatohepatitis (NASH), muscular dystrophies (e.g., Duchenne, Becker, limb-girdle, congenital, facioscapulohumeral, myotonic, oculopharyngeal, distal, and Emery-Dreifuss), glaucoma, corneal scarring, keloids, wound healing, adhesions, hypertrophic scarring, other scarring, e.g. associated with burns, surgery or other trauma, stroke, collagen vascular diseases such as systemic lupus erythematosus, rheumatoid arthritis and scleroderma, spinal cord injury and multiple sclerosis. Furthermore, BMP1, TLL1 and TLL2 inhibitors may have additional therapeutic applications in muscular disease based on their impact on myostatin biology, in particular muscular dystrophies (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer or old age.

SUMMARY OF THE INVENTION

According to a first aspect of the invention, there is provided a BMP1, TLL1 and/or TLL2 binding protein, which comprises:

(a)(i) any one or a combination of CDRs selected from CDRH1, CDRH2, CDRH3 from SEQ ID NOs: 7, 22, 40, 54, 67, 82, 96, 110, 124, 138, 152, 166, 180, 194, 207, and 222 and/or CDRL1, CDRL2, CDRL3 from SEQ ID NOs: 8, 21, 39, 53, 68, 81, 95, 109, 123, 137, 151, 165, 179, 193, 208, and 221; or (ii) a CDR variant of (i) wherein the variant has 1, 2, or 3 amino acid modifications; or (b) a VH region comprising a sequence at least 80% identical to the sequence of SEQ ID NO: 7, 22, 40, 54, 67, 82, 96, 110, 124, 138, 152, 166, 180, 194, 207, or 222 and/or a VL region comprising a sequence at least 80% identical to the sequence of SEQ ID NO: 8, 21, 39, 53, 68, 81, 95, 109, 123, 137, 151, 165, 179, 193, 208, or 221.

In an embodiment, provided is a BMP1, TLL1 and/or TLL2 binding protein comprising the following 6 CDRs:

LCDR1 of (SEQ ID NO: 1)
RASQSVSSYLA;

LCDR2 of (SEQ ID NO: 2)
DASNRAT;

LCDR3 of (SEQ ID NO: 3)
QQSDSWPPT;

HCDR1 of (SEQ ID NO: 4)
GYYMS;

HCDR2 of (SEQ ID NO: 5)
WINPLSGETNYAQKFQG;
and

HCDR3 of (SEQ ID NO: 6)
DTGELDGMNWYFDL.

In an embodiment, provided is a BMP1, TLL1 and/or TLL2 binding protein, which comprises a VH region that is 100% identical to SEQ ID NO: 7 and a VL region that is 100% identical to SEQ ID NO: 8.

In an embodiment, provided is a BMP1, TLL1 and/or TLL2 binding protein, which comprises a light chain that is 100% identical to SEQ ID NO: 9 and a heavy chain that is 100% identical to SEQ ID NO: 10.

According to a further aspect of the invention, there is provided a polynucleotide sequence encoding a BMP1, TLL1 and/or TLL2 binding protein as defined herein.

According to a further aspect of the invention, there is provided an expression vector comprising a polynucleotide sequence as defined herein.

According to a further aspect of the invention, there is provided a recombinant host cell comprising a polynucleotide sequence as defined herein or an expression vector as defined herein.

According to a further aspect of the invention, there is provided a pharmaceutical composition comprising a BMP1, TLL1 and/or TLL2 binding protein as defined herein and a pharmaceutically acceptable diluent or carrier.

According to a further aspect of the invention, there is provided a method for the treatment of a fibrotic related disease or disorder in a subject in need thereof, comprising administering to the subject a therapeutically effective amount of a BMP1, TLL1 and/or TLL2 binding protein as defined herein or a pharmaceutical composition as defined herein.

According to a further aspect of the invention, there is provided a BMP1, TLL1 and/or TLL2 binding protein as defined herein or a pharmaceutical composition as defined herein, for use in therapy.

According to a further aspect of the invention, there is provided a BMP1, TLL1 and/or TLL2 binding protein as defined herein or a pharmaceutical composition as defined herein, for use in the treatment of a fibrosis related disease or disorder.

According to a further aspect of the invention, there is provided use of a BMP1, TLL1 and/or TLL2 binding protein as defined herein or a pharmaceutical composition as defined herein in the manufacture of a medicament for use in the treatment of a fibrosis related disease or disorder.

According to a further aspect of the invention, there is provided a method for promoting muscle growth and/or improving muscle function in a subject in need thereof, comprising administering to the subject a therapeutically effective amount of a BMP1, TLL1 and/or TLL2 binding protein as defined herein or a pharmaceutical composition as defined herein.

According to a further aspect of the invention, there is provided a BMP1, TLL1 and/or TLL2 binding protein as defined herein or a pharmaceutical composition as defined herein, for use in promoting muscle growth and/or improving muscle function.

According to a further aspect of the invention, there is provided use of a BMP1, TLL1 and/or TLL2 binding protein as defined herein or a pharmaceutical composition as defined herein in the manufacture of a medicament for use in promoting muscle growth and/or improving muscle function.

BRIEF DESCRIPTION OF THE FIGURES

FIG. 17A: Left ventricular fibrosis, measured by quantitative assessment of Masson's Trichrome histopathological staining, in the rat Dahl S study. (PBS+0.3% NaCl vs. PBS+8% NaCl compared by unpaired t-test, p<0.01; PBS+8% NaCl vs. Compound C+8% NaCl compared by one-way ANOVA, #p<0.05). FIG. 17B: The Compound C-treated group exhibits a 9% increase in skeletal muscle mass compared to PBS+8% NaCl and a 10% increase compared to the anti-RSV treated group. (PBS+8% NaCl vs. mAb groups compared by one-way ANOVA, p<0.01).

DETAILED DESCRIPTION OF THE INVENTION

Definitions

Figure 1:
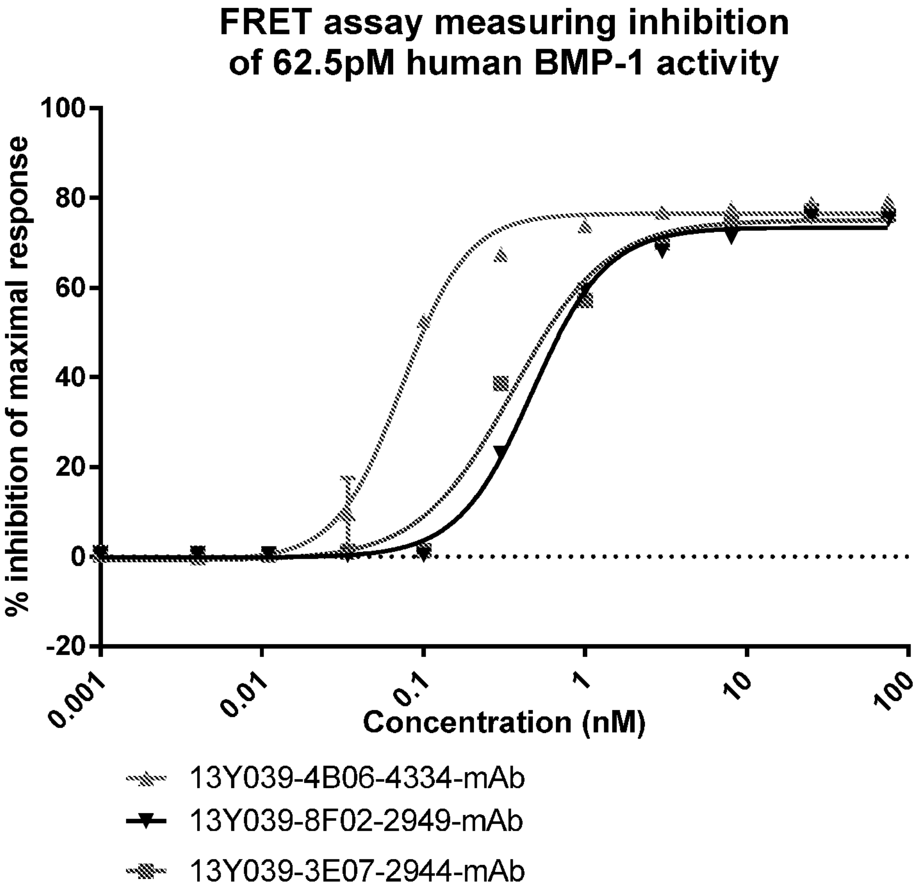
FIG. 1: FRET assay measuring inhibition of 62.5 pM human BMP-1 activity by anti-BMP1/TLL antibody molecules. Dose-response curves were plotted for 13Y039-4B06-4334, 13Y039-3E07-2944, and 13Y039-8F02-2949. Antibodies were tested from a top concentration of 75 nM with a 3-fold dilution series across 11-points. Figure shows the mean of duplicate data points, with standard deviation as error bars.

Unless defined otherwise, all technical and scientific terms used herein have the meaning commonly understood by a person skilled in the art to which this invention belongs. As used herein, the following terms have the meanings ascribed to them below.

The term "BMP1, TLL1 and/or TLL2 binding protein" as used herein refers to antibodies and other protein constructs, such as domains, that are capable of binding to BMP1 (bone morphogenetic protein 1), TLL1 (tolloid-like 1) and/or TLL2 (tolloid-like 2). The terms "BMP1, TLL1 and/or TLL2 binding protein" and "antigen binding protein" are used interchangeably herein. This does not include the natural cognate ligand or receptor.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (e.g., a domain antibody (DAB)), antigen binding antibody fragments, Fab, $F(ab')_2$, Fv, disulphide linked Fv, single chain Fv, disulphide-linked scFv, diabodies, TANDABS, etc. and modified versions of any of the foregoing (for a summary of alternative "antibody" formats see Holliger and Hudson, Nature Biotechnology, 2005, Vol 23, No. 9, 1126-1136).

The terms "full", "whole" or "intact" used in reference to an antibody, which are used interchangeably herein, refer to a heterotetrameric glycoprotein with an approximate molecular weight of 150,000 daltons. An intact antibody is composed of two identical heavy chains (HCs) and two identical light chains (LCs) linked by covalent disulphide bonds. This H2L2 structure folds to form three functional domains comprising two antigen-binding fragments, known as 'Fab' fragments, and a 'Fc' crystallisable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called μ, α, γ, ε and δ respectively, each heavy chain can pair with either a K or λ light chain. The majority of antibodies in the serum belong to the IgG class, there are four isotypes of human IgG (IgG1, IgG2, IgG3 and IgG4), the sequences of which differ mainly in their hinge region.

Fully human antibodies can be obtained using a variety of methods, for example using yeast-based libraries or transgenic animals (e.g. mice) that are capable of producing repertoires of human antibodies. Yeast presenting human antibodies on their surface that bind to an antigen of interest can be selected using FACS (Fluorescence-Activated Cell Sorting) based methods or by capture on beads using labelled antigens. Transgenic animals that have been modified to express human immunoglobulin genes can be immunised with an antigen of interest and antigen-specific human antibodies isolated using B-cell sorting techniques. Human antibodies produced using these techniques can then be characterised for desired properties such as affinity, developability and selectivity.

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain.

The term "neutralises" as used throughout the present specification means that the biological activity of BMP1, TLL1 and/or TLL2 is reduced in the presence of an antigen binding protein as described herein in comparison to the activity of BMP1, TLL1 and/or TLL2 in the absence of the antigen binding protein, in vitro or in vivo. Neutralisation may be due to one or more of blocking BMP1, TLL1, and/or TLL2 binding to its target substrates, and preventing BMP1, TLL1, and/or TLL2 from cleaving its target substrates. For example, the fluorescence resonance energy transfer (FRET) based assays described in the Examples may be used to assess the neutralising capability of a BMP1, TLL1, and/or TLL2 binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3", "LCDR1", "LCDR2", "LCDR3", "HCDR1, "HCDR2", "HCDR3" used in the Examples and set forth in the Sequence Listing follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. There are also alternative numbering conventions for CDR sequences, for example those set out in Chothia et al. (1989) Nature 342: 877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods.

Table 1-1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1-1

| | Kabat CDR | Chothia CDR | AbM CDR | Contact CDR |
|---|---|---|---|---|
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

CDRs may be modified by at least one amino acid substitution, deletion or addition, wherein the variant antigen binding protein substantially retains the biological characteristics of the unmodified protein.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acid. Typically, the modification is a substitution, particularly a conservative substitution, for example as shown in Table 1-2 below.

TABLE 1-2

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the flanking residues that comprise the CDR as part of alternative definition(s) e.g. Kabat or Chothia, may be substituted with a conservative amino acid residue.

Such antigen binding proteins comprising variant CDRs as described above may be referred to herein as "functional CDR variants".

"Antigen binding site" refers to a site on an antigen binding protein that is capable of specifically binding to an antigen, this may be a single variable domain, or it may be paired VH/VL domains as can be found on a standard antibody. Single-chain Fv (ScFv) domains can also provide antigen binding sites.

In some embodiments, a BMP1, TLL1 and/or TLL2 binding protein is an anti-BMP1, TLL1 and/or TLL2 antibody or fragment thereof.

A fragment of the antibody (which may also be referred to as "antibody fragment", "immunoglobulin fragment", "antigen-binding fragment" or "antigen-binding polypeptide") as used herein refers to a portion of an antibody (or constructs that contain said portion) that specifically binds to the target, namely BMP1, TLL1 and/or TLL2. Examples of binding fragments encompassed within the term antibody fragment include:

(i) a Fab fragment (a monovalent fragment consisting of the VL, VH, CL and CH1 domains);
(ii) a F(ab')2 fragment (a bivalent fragment consisting of two Fab fragments linked by a disulphide bridge at the hinge region);
(iii) a Fd fragment (consisting of the VH and CH1 domains);
(iv) a Fv fragment (consisting of the VL and VH domains of a single arm of an antibody);
(v) a single chain variable fragment, scFv (consisting of VL and VH domains joined, using recombinant methods, by a synthetic linker that enables them to be made as a single protein chain in which the VL and VH regions pair to form monovalent molecules);
(vi) a VH (an immunoglobulin chain variable domain consisting of a VH domain);
(vii) a VL (an immunoglobulin chain variable domain consisting of a VL domain);
(viii) a domain antibody (dAb, consisting of either the VH or VL domain);
(ix) a minibody (consisting of a pair of scFv fragments which are linked via CH3 domains); and
(x) a diabody (consisting of a noncovalent dimer of scFv fragments that consist of a VH domain from one antibody connected by a small peptide linker a VL domain from another antibody).

"Human antibody" refers to antibodies having variable and constant regions derived from human germline immunoglobulin sequences. Said human antibodies may include amino acid residues not encoded by human germline immunoglobulin sequences (e.g. mutations introduced by random or site-specific mutagenesis or by somatic mutation), for example in the CDRs and in particular CDR3. However, the term is not intended to include antibodies in which CDR sequences derived from the germline of another mammalian species, such as a mouse, have been grafted onto human framework sequences. Human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g. a mouse) that is transgenic for human immunoglobulin genes or antibodies prepared, expressed, created or isolated by any other means that involves splicing of human immunoglobulin gene sequences to other DNA sequences, may also be referred to as "recombinant human antibodies".

Substituting at least one amino acid residue in the framework region of a non-human immunoglobulin variable domain with the corresponding residue from a human variable domain is referred to as "humanisation". Humanisation of a variable domain may reduce immunogenicity in humans.

In one embodiment, antigen binding proteins of the present disclosure show cross-reactivity between human BMP1, TLL1 and/or TLL2 and BMP1, TLL1 and/or TLL2 from another species, such as murine, rat, and/or cynomolgus BMP1, TLL1 and/or TLL2. In an embodiment, the antigen binding proteins of the invention specifically bind human and murine BMP1, TLL1 and/or TLL2. This is particularly useful, since drug development typically requires testing of lead drug candidates in mouse systems before the drug is tested in humans. The provision of a drug that can bind human and mouse species allows one to test results in these systems and make side-by-side comparisons of data using the same drug. This avoids the complication of needing to find a drug that works against a mouse BMP1, TLL1 and/or TLL2 and a separate drug that works against human BMP1, TLL1 and/or TLL2 and also avoids the need to compare results in humans and mice using non-identical drugs. Cross reactivity between other species used in disease models such as dog or monkey, such as cynomolgus monkey, is also envisaged.

"Specificity" refers to the number of different types of antigens or antigenic determinants to which a particular antibody or fragment thereof can bind. The specificity of an antibody is the ability of the antibody to recognise a particular antigen as a unique molecular entity and distinguish it from another. An antibody that "specifically binds" to an antigen or an epitope is a term well understood in the art. A molecule is said to exhibit "specific binding" if it reacts more frequently, more rapidly, with greater duration and/or with greater affinity with a particular target antigen or epitope, than it does with alternative targets. An antibody "specifically binds" to a target antigen or epitope if it binds with greater affinity, avidity, more readily, and/or with greater duration than it binds to other substances.

"Affinity", represented by the equilibrium constant for the dissociation of an antigen with an antigen-binding polypeptide (KD), is a measure of the binding strength between an antigenic determinant and an antigen-binding site on the antibody (or fragment thereof): the lesser the value of the KD, the stronger the binding strength between an antigenic determinant and the antigen-binding polypeptide. Alternatively, the affinity can also be expressed as the affinity constant (KA), which is 1/KD. Affinity can be determined by known methods, depending on the specific antigen of interest, such as equilibrium methods (e.g. enzyme-linked immunoabsorbent assay (ELISA) or radioimmunoassay (RIA)), or kinetics (e.g. BIACORE analysis). For example, the BIACORE methods described in the Examples may be used to measure binding affinity.

Avidity, also referred to as functional affinity, is the cumulative strength of binding at multiple interaction sites, e.g. the sum total of the strength of binding of two molecules (or more, e.g. in the case of a bispecific or multispecific molecule) to one another at multiple sites, e.g. taking into account the valency of the interaction.

The term "epitope" as used herein refers to that portion of the antigen that makes contact with a particular binding domain of the antigen binding protein, also known as the paratope. An epitope may be linear or conformational/discontinuous. A conformational or discontinuous epitope comprises amino acid residues that are separated by other sequences, i.e. not in a continuous sequence in the antigen's primary sequence assembled by tertiary folding of the polypeptide chain. Although the residues may be from different regions of the polypeptide chain, they are in close proximity in the three-dimensional structure of the antigen. In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. Epitope mapping can be carried out using various techniques known to persons skilled in the art as described in publications such as *Methods in Molecular Biology 'Epitope Mapping Protocols'*, Mike Schutkowski and Ulrich Reineke (volume 524, 2009) and Johan Rockberg and Johan Nilvebrant (volume 1785, 2018). Exemplary methods include peptide-based approaches such as pepscan whereby a series of overlapping peptides are screened for binding using techniques such as ELISA or by in vitro display of large libraries of peptides or protein mutants, e.g. on phage. Detailed epitope information can be determined by structural techniques including X-ray crystallography, solution nuclear magnetic resonance (NMR) spectroscopy and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

Competition between the BMP1/TLL1/TLL2 binding protein of the invention and a reference BMP1/TLL1/TLL2 binding protein, e.g. a reference antibody, may be determined by one or more techniques known to the skilled person such as ELISA, FMAT, Surface Plasmon Resonance (SPR) or FORTEBIO OCTET Bio-Layer Interferometry (BLI). Such techniques may also be referred to as epitope binning. There are several possible reasons for this competition: the two proteins may bind to the same or overlapping epitopes, there may be steric inhibition of binding, or binding of the first protein may induce a conformational change in the antigen that prevents or reduces binding of the second protein.

The reduction or inhibition in biological activity may be partial or total. A neutralising antigen binding protein may neutralise the activity of BMP1, TLL1 and/or TLL2 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to BMP1, TLL1 and/or TLL2 activity in the absence of the antigen binding protein.

In some embodiments, the antigen binding protein (i.e. polypeptide) of the invention is isolated. An "isolated" antigen binding protein is one that is removed from its original environment. The term "isolated" may be used to refer to an antigen binding protein that is substantially free of other antigen binding proteins having different antigenic specificities (e.g. an isolated antigen binding protein that specifically binds BMP1, TLL1 and/or TLL2, or a fragment thereof, is substantially free of antigen binding proteins that specifically bind antigens other than BMP1, TLL1 and/or TLL2). The term "isolated" may also be used to refer to preparations where the isolated antigen binding protein is sufficiently pure to be administered therapeutically when formulated as an active ingredient of a pharmaceutical composition, or at least 70-80% (w/w) pure, more preferably, at least 80-90% (w/w) pure, even more preferably, 90-95% (w/w) pure; and, most preferably, at least 95%, 96%, 97%, 98%, 99%, or 100% (w/w) pure.

In some embodiments, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

For the purposes of comparing two closely related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or "identical" to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If first and second polypeptide sequences are 9 amino acid residues long and share 6 identical residues, the first and second polypeptide sequences share greater than 66% identity (the first and second polypeptide sequences share 66.7% identity).

Alternatively, for the purposes of comparing a first, reference polypeptide sequence to a second, comparison polypeptide sequence, the number of additions, substitutions and/or deletions made to the first sequence to produce the second sequence may be ascertained. An "addition" is the addition of one amino acid residue into the sequence of the first polypeptide (including addition at either terminus of the first polypeptide). A "substitution" is the substitution of one amino acid residue in the sequence of the first polypeptide with one different amino acid residue. Said substitution may be conservative or non-conservative. A "deletion" is the deletion of one amino acid residue from the sequence of the first polypeptide (including deletion at either terminus of the first polypeptide).

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions, and also bacteriophage and phagemid systems. The term "recombinant host cell" (or simply "host cell"), as used herein, is intended to refer to a cell into which a recombinant expression vector has been introduced. Such terms are intended to refer not only to the particular subject cell but to the progeny of such a cell.

References to "subject", "patient" or "individual" refer to a subject, in particular a mammalian subject, to be treated. Mammalian subjects include humans, non-human primates, farm animals (such as cows), sports animals, or pet animals, such as dogs, cats, guinea pigs, rabbits, rats or mice. In some embodiments, the subject is a human. In alternative embodiments, the subject is a non-human mammal, such as a mouse.

The term "sufficient amount" means an amount sufficient to produce a desired effect. The term "therapeutically effective amount" is an amount that is effective to ameliorate a symptom of a disease or disorder. A therapeutically effective amount can be a "prophylactically effective amount" as prophylaxis can be considered therapy.

As used herein, the term "about" when used herein includes up to and including 10% greater and up to and including 10% lower than the value specified, particularly up to and including 5% greater and up to and including 5% lower than the value specified. The term "between", includes the values of the specified boundaries.

The skilled person will appreciate that, upon production of an antigen binding protein, such as an antibody in a host cell, post-translational modifications may occur. For example, this may include the cleavage of certain leader sequences, the addition of various sugar moieties in various glycosylation patterns, non-enzymatic glycation, deamidation, oxidation, disulfide bond scrambling and other cysteine variants such as free sulfhydryls, racemized disulfides, thioethers and trisulfide bonds, isomerisation, C-terminal lysine clipping, and N-terminal glutamine cyclisation. The invention encompasses the use of antigen binding proteins that have been subjected to, or have undergone, one or more post-translational modifications. Thus an "antigen binding protein" or "antibody" of the invention includes an "antigen binding protein" or "antibody", respectively, as defined earlier that has undergone a post-translational modification such as described herein.

Glycation is a post-translational non-enzymatic chemical reaction between a reducing sugar, such as glucose, and a free amine group in the protein, and is typically observed at the epsilon amine of lysine side chains or at the N-Terminus of the protein. Glycation can occur during production and storage only in the presence of reducing sugars.

Deamidation, which can occur during production and storage, is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e. in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR) region, or in the Fc region. Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling. The formation of a thioether and racemization of a disulphide bond can occur under basic conditions, in production or storage, through a beta elimination of disulphide bridges back to cysteine residues via a dehydroalanine and persulfide intermediate. Subsequent crosslinking of dehydroalanine and cysteine results in the formation of a thioether bond or the free cysteine residues can reform a disulphide bond with a mixture of D- and L-cysteine.

Trisulfides result from insertion of a sulfur atom into a disulphide bond (Cys-S—S—S-Cys) and are formed due to the presence of hydrogen sulphide in production cell culture.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Upon administration to the human subject/patient is likely to result in the removal of any remaining C-terminal lysines.

Fc engineering methods can be applied to modify the functional or pharmacokinetics properties of an antibody. Effector function may be altered by making mutations in the Fc region that increase or decrease binding to C1q or Fcγ receptors and modify CDC or ADCC activity respectively. Modifications to the glycosylation pattern of an antibody can also be made to change the effector function. The in vivo half-life of an antibody can be altered by making mutations that affect binding of the Fc to the FcRn (Neonatal Fc Receptor).

The term "effector function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

The interaction between the Fc region of an antigen binding protein or antibody and various Fc receptors (FcR), including FcγRI (CD64), FcγRII (CD32), FcγRIII (CD16), FcRn, C1q, and type II Fc receptors is believed to mediate the effector functions of the antigen binding protein or antibody. Significant biological effects can be a consequence of effector functionality. Usually, the ability to mediate effector function requires binding of the antigen binding protein or antibody to an antigen and not all antigen binding proteins or antibodies will mediate every effector function.

Effector function can be assessed in a number of ways including, for example, evaluating ADCC effector function of antibody coated to target cells mediated by Natural Killer (NK) cells via FcγRIII, or monocytes/macrophages via FcγRI, or evaluating CDC effector function of antibody coated to target cells mediated by complement cascade via C1q. For example, an antigen binding protein of the present invention can be assessed for ADCC effector function in a Natural Killer cell assay. Examples of such assays can be found in Shields et al, 2001, The Journal of Biological Chemistry, Vol. 276, p. 6591-6604; Chappel et al, 1993, The Journal of Biological Chemistry, Vol 268, p. 25124-25131; Lazar et al, 2006, PNAS, 103; 4005-4010. Examples of assays to determine CDC function include those described in J Imm Meth, 1995, 184: 29-38.

The effects of mutations on effector functions (e.g., FcRn binding, FcγRs and C1q binding, CDC, ADCML, ADCC, ADCP) can be assessed, e.g., as described in Grevys et al., *J Immunol.* 2015 Jun. 1; 194(11): 5497-5508, or Tam et al., Antibodies 2017, 6(3); Monnet et al., 2014 mAbs, 6:2, 422-436.

Throughout this specification, amino acid residues in Fc regions, in antibody sequences or full-length antigen binding protein sequences, are numbered according to the EU index numbering convention.

Some isotypes of human constant regions, in particular IgG4 and IgG2 isotypes, essentially lack the functions of a) activation of complement by the classical pathway; and b) ADCC. Various modifications to the heavy chain constant region of antigen binding proteins may be carried out to alter effector function depending on the desired effector property. IgG1 constant regions containing specific mutations that reduce binding to Fc receptors and reduce an effector function, such as ADCC and CDC, have been described (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

In one embodiment, there is provided a BMP1, TLL1 and/or TLL2 binding protein comprising a constant region such that the antigen binding protein has reduced effector function, such as reduced ADCC and/or CDC. In one such embodiment, the heavy chain constant region may comprise a naturally disabled constant region of an IgG2 or IgG4 isotype or a mutated IgG1 constant region. Examples of suitable modifications are described in EP0307434. One example comprises substitution with alanine at positions 235 and 237 (EU index numbering), i.e. L235A and G237A (commonly referred to as “LAGA” mutations). Another example comprises substitution with alanine at positions 234 and 235 (EU index numbering), i.e. L234A and L235A (commonly referred to as “LALA” mutations). Further examples, described in EP2691417 and U.S. Pat. No. 8,969,526, comprise P329G or P329R, in combination with the LALA mutations (EU index numbering) for IgG1 Fcs and P329G or P329R in combination with S228P and L235E for IgG4 Fcs (EU index numbering).

Additional alterations and mutations to decrease effector function include: (with reference to IgG1 unless otherwise noted): aglycosylated N297A or N297Q or N297G; L235E; IgG4: F234A/L235A; and chimeric IgG2/IgG4. IgG2: H268Q/V309L/A330S/P331S, and IgG2: V234A/G237A/P238S/H268A/V309L/A330S/P331S can reduce FcγR and C1q binding (Wang et al. 2018 and U.S. Pat. No. 8,961,967).

Other mutations that decrease effector function include L234F/L235E/P331S; a chimeric antibody created using the CH1 and hinge region from human IgG2 and the CH2 and CH3 regions from human IgG4; IgG2m4, based on the IgG2 isotype with four key amino acid residue changes derived from IgG4 (H268Q, V309L, A330S and P331 S); IgG2a that contains V234A/G237A/P238S/H268A/V309L/A330S/P331S substitutions to eliminate affinity for Fcγ receptors and C1q complement protein; IgG2m4 (H268Q/V309L/A330S/P331S, changes to IgG4); IgG4 (S228P/L234A/L235A); hulgG1 L234A/L235A (AA); hulgG4 S228P/L234A/L235A; IgG1a (L234A/L235A/G237A/P238S/H268A/A330S/P331S); IgG4 σ1 (S228P/F234A/L235A/G237A/P238S); and IgG4 σ2 (S228P/F234A/L235A/ΔG236/G237A/P238S, wherein Δ denotes a deletion) (Tam et al., Antibodies 2017, 6(3)).

Antigen Binding Proteins

Provided herein are antigen binding proteins capable of specifically binding to BMP1, TLL1 and/or TLL2. In some embodiments, such an antigen binding protein is an anti-BMP1, TLL1 and/or TLL2 antibody or fragment thereof.

The antigen binding proteins described herein neutralize the activity of BMP1, TLL1 and/or TLL2 through binding to the catalytic domain of BMP1, TLL1 and/or TLL2. Without being bound by any theory, it is believed that the antigen binding proteins of the invention limit fibrosis and slow organ dysfunction through BMP1, TLL1 and/or TLL2 neutralisation. For example, BMP1/TLL convert soluble procollagen I into insoluble collagen fibrils leading to fibrosis and the antigen binding proteins described herein can neutralize cleavage of procollagen I. It is believed that fibrosis occurs in response to tissue injury across many, if not all, organ systems. While initial fibrosis is beneficial to maintenance of tissue integrity, excessive fibrosis leads to scarring and inhibition of normal organ function. Reducing this pathological fibrosis thus has the potential to delay disease progression. Additionally, BMP1 inhibition can also promote muscle growth and has been shown to increase muscle function, and thus may also reduce frailty.

In one embodiment, the antigen binding protein is an antibody or fragment thereof, wherein the antibody or fragment thereof is an scFv, Fab, Fab', F(ab')2, Fv, variable domain (e.g. VH or VL), diabody, minibody or monoclonal antibody. In a further embodiment, the antibody or fragment thereof is a monoclonal antibody.

Antibodies of the invention can be of any class, e.g. IgG, IgA, IgM, IgE, IgD, or isotypes thereof, and can comprise a kappa or lambda light chain. In one embodiment, the antibody is an IgG antibody, for example, at least one of isotypes, IgG1, IgG2, IgG3 or IgG4. In a further embodiment, the antibody is in a format, such as an IgG format, that has been modified to confer desired properties, such as having the Fc mutated to reduce effector function, extend half-life, alter ADCC, or improve hinge stability. Such modifications are described above.

In one embodiment, the antibody or fragment thereof is human. Thus, the antibody or fragment thereof may be derived from a human immunoglobulin (Ig) sequence. The CDR, framework and/or constant region of the antibody (or fragment thereof) can be derived from a human Ig sequence, in particular a human IgG sequence. The CDR, framework and/or constant region can be substantially identical to a human Ig sequence, in particular a human IgG sequence. An advantage of using human antibodies is that they are low or non-immunogenic in humans.

An antibody or fragment thereof can also be chimeric, for example a mouse-human antibody chimera.

Alternatively, the antibody or fragment thereof is derived from a non-human species, such as a mouse. Such non-human antibodies can be modified to increase their similarity to antibody variants produced naturally in humans, thus the antibody or fragment thereof can be partially or fully humanised. Therefore, in one embodiment, the antibody or fragment thereof is humanised.

In one embodiment, a BMP1, TLL1 and/or TLL2 binding protein is an IgG antibody.

In some embodiments, a BMP1, TLL1 and/or TLL2 binding protein is an IgG antibody comprising at least one mutation to reduce Fc-mediated effector function, such as reduced ADCC.

In some embodiments, a BMP1, TLL1 and/or TLL2 binding protein is an IgG antibody comprising mutations L235A and G237A (also referred to herein as "LAGA" mutations) to reduce Fc-mediated effector function, such as reduced ADCC.

In some embodiments, a BMP1, TLL1 and/or TLL2 binding protein is a fully human monoclonal antibody. In some embodiments, a BMP1, TLL1 and/or TLL2 binding protein is a fully human monoclonal IgG1 antibody comprising mutations L235A and G237A to reduce Fc-mediated effector function, such as reduced ADCC.

Antigen Binding Protein Sequences

BMP1, TLL1 and/or TLL2 antigen binding proteins, such anti-BMP1, TLL1 and/or TLL2 antibodies or fragments, of the invention can be described with reference to their CDR sequences.

According to a first aspect of the invention, there is provided a BMP1, TLL1 and/or TLL2 antigen binding protein, such as an anti-BMP1, TLL1 and/or TLL2 antibody or fragment thereof, which comprises:

(a)(i) any one or a combination of CDRs selected from CDRH1, CDRH2, CDRH3 from SEQ ID NOs: 7, 22, 40, 54, 67, 82, 96, 110, 124, 138, 152, 166, 180, 194, 207, and 222 and/or CDRL1, CDRL2, CDRL3 from SEQ ID NOs: 8, 21, 39, 53, 68, 81, 95, 109, 123, 137, 151, 165, 179, 193, 208, and 221; or (ii) a CDR variant of (i) wherein the variant has 1, 2, or 3 amino acid modifications; or (b) a VH region comprising a sequence at least 80% identical to the sequence of SEQ ID NO: 7, 22, 40, 54, 67, 82, 96, 110, 124, 138, 152, 166, 180, 194, 207, or 222 and/or a VL region comprising a sequence at least 80% identical to the sequence of SEQ ID NO: 8, 21, 39, 53, 68, 81, 95, 109, 123, 137, 151, 165, 179, 193, 208, or 221.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 7, and/or CDRL1, CDRL2, CDRL3 from SEQ ID NO: 8; or (ii) a CDR variant of (i) wherein the variant has 1, 2, or 3 amino acid modifications; or (b) a VH region comprising a sequence at least 80% identical to the sequence of SEQ ID NO: 7 and/or a VL region comprising a sequence at least 80% identical to the sequence of SEQ ID NO: 8.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 22, and/or CDRL1, CDRL2, CDRL3 from SEQ ID NO: 21; or (ii) a CDR variant of (i) wherein the variant has 1, 2, or 3 amino acid modifications; or (b) a VH region comprising a sequence at least 80% identical to the sequence of SEQ ID NO: 22 and/or a VL region comprising a sequence at least 80% identical to the sequence of SEQ ID NO: 21.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 40, and/or CDRL1, CDRL2, CDRL3 from SEQ ID NO: 39; or (ii) a CDR variant of (i) wherein the variant has 1, 2, or 3 amino acid modifications; or (b) a VH region comprising a sequence at least 80% identical to the sequence of SEQ ID NO: 40 and/or a VL region comprising a sequence at least 80% identical to the sequence of SEQ ID NO: 39.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 54, and/or CDRL1, CDRL2, CDRL3 from SEQ ID NO: 53; or (ii) a CDR variant of (i) wherein the variant has 1, 2, or 3 amino acid modifications; or (b) a VH region comprising a sequence at least 80% identical to the sequence of SEQ ID NO: 54 and/or a VL region comprising a sequence at least 80% identical to the sequence of SEQ ID NO: 53.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 67, and/or CDRL1, CDRL2, CDRL3 from SEQ ID NO: 68; or (ii) a CDR variant of (i) wherein the variant has 1, 2, or 3 amino acid modifications; or (b) a VH region comprising a sequence at least 80% identical to the sequence of SEQ ID NO: 67 and/or a VL region comprising a sequence at least 80% identical to the sequence of SEQ ID NO: 68.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 82, and/or CDRL1, CDRL2, CDRL3 from SEQ ID NO: 81; or (ii) a CDR variant of (i) wherein the variant has 1, 2, or 3 amino acid modifications; or (b) a VH region comprising a sequence at least 80% identical to the sequence of SEQ ID NO: 82 and/or a VL region comprising a sequence at least 80% identical to the sequence of SEQ ID NO: 81.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 96, and/or CDRL1, CDRL2, CDRL3 from SEQ ID NO:

95; or (ii) a CDR variant of (i) wherein the variant has 1, 2, or 3 amino acid modifications; or (b) a VH region comprising a sequence at least 80% identical to the sequence of SEQ ID NO: 96 and/or a VL region comprising a sequence at least 80% identical to the sequence of SEQ ID NO: 95.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 110, and/or CDRL1, CDRL2, CDRL3 from SEQ ID NO: 109; or (ii) a CDR variant of (i) wherein the variant has 1, 2, or 3 amino acid modifications; or (b) a VH region comprising a sequence at least 80% identical to the sequence of SEQ ID NO: 110 and/or a VL region comprising a sequence at least 80% identical to the sequence of SEQ ID NO: 109.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 124, and/or CDRL1, CDRL2, CDRL3 from SEQ ID NO: 123; or (ii) a CDR variant of (i) wherein the variant has 1, 2, or 3 amino acid modifications; or (b) a VH region comprising a sequence at least 80% identical to the sequence of SEQ ID NO: 124 and/or a VL region comprising a sequence at least 80% identical to the sequence of SEQ ID NO: 123.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 138, and/or CDRL1, CDRL2, CDRL3 from SEQ ID NO: 137; or (ii) a CDR variant of (i) wherein the variant has 1, 2, or 3 amino acid modifications; or (b) a VH region comprising a sequence at least 80% identical to the sequence of SEQ ID NO: 138 and/or a VL region comprising a sequence at least 80% identical to the sequence of SEQ ID NO: 137.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 152, and/or CDRL1, CDRL2, CDRL3 from SEQ ID NO: 151; or (ii) a CDR variant of (i) wherein the variant has 1, 2, or 3 amino acid modifications; or (b) a VH region comprising a sequence at least 80% identical to the sequence of SEQ ID NO: 152 and/or a VL region comprising a sequence at least 80% identical to the sequence of SEQ ID NO: 151.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 166, and/or CDRL1, CDRL2, CDRL3 from SEQ ID NO: 165; or (ii) a CDR variant of (i) wherein the variant has 1, 2, or 3 amino acid modifications; or (b) a VH region comprising a sequence at least 80% identical to the sequence of SEQ ID NO: 166 and/or a VL region comprising a sequence at least 80% identical to the sequence of SEQ ID NO: 165.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 180, and/or CDRL1, CDRL2, CDRL3 from SEQ ID NO: 179; or (ii) a CDR variant of (i) wherein the variant has 1, 2, or 3 amino acid modifications; or (b) a VH region comprising a sequence at least 80% identical to the sequence of SEQ ID NO: 180 and/or a VL region comprising a sequence at least 80% identical to the sequence of SEQ ID NO: 179.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 194, and/or CDRL1, CDRL2, CDRL3 from SEQ ID NO: 193; or (ii) a CDR variant of (i) wherein the variant has 1, 2, or 3 amino acid modifications; or (b) a VH region comprising a sequence at least 80% identical to the sequence of SEQ ID NO: 194 and/or a VL region comprising a sequence at least 80% identical to the sequence of SEQ ID NO: 193.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 207, and/or CDRL1, CDRL2, CDRL3 from SEQ ID NO: 208; or (ii) a CDR variant of (i) wherein the variant has 1, 2, or 3 amino acid modifications; or (b) a VH region comprising a sequence at least 80% identical to the sequence of SEQ ID NO: 207 and/or a VL region comprising a sequence at least 80% identical to the sequence of SEQ ID NO: 208.

In one embodiment, the BMP1, TLL1 and/or TLL2 antigen binding protein, such as anti-BMP1, TLL1 and/or TLL2 antibody or fragment thereof, comprises one or more of:

(a)(i) any one or a combination of CDRs selected from CDRH1, CDRH2, CDRH3 from SEQ ID NO: 222, and/or CDRL1, CDRL2, CDRL3 from SEQ ID NO: 221; or (ii) a CDR variant of (i) wherein the variant has 1, 2, or 3 amino acid modifications; or (b) a VH region comprising a sequence at least 80% identical to the sequence of SEQ ID NO: 222 and/or a VL region comprising a sequence at least 80% identical to the sequence of SEQ ID NO: 221.

In one embodiment, the BMP1, TLL1 and/or TLL2 antigen binding protein, such as anti-BMP1, TLL1 and/or TLL2 antibody or fragment thereof, comprises one or more of:

a LCDR1 comprising a sequence having at least 80% sequence identity with RASQSVSSYLA (SEQ ID NO: 1); and/or a LCDR2 comprising a sequence having at least 80% sequence identity with DASNRAT (SEQ ID NO: 2); and/or a LCDR3 comprising a sequence having at least 80% sequence identity with QQSDSWPPT (SEQ ID NO: 3); and/or a HCDR1 comprising a sequence having at least 80% sequence identity with GYYMS (SEQ ID NO: 4); and/or a HCDR2 comprising a sequence having at least 80% sequence identity with WINPLSGETNYAQKFQG (SEQ ID NO: 5); and/or a HCDR3 comprising a sequence having at least 80% sequence identity with DTGELDGMNWYFDL (SEQ ID NO: 6).

In one embodiment, the BMP1, TLL1 and/or TLL2 antigen binding protein, such as anti-BMP1, TLL1 and/or TLL2 antibody or fragment thereof, comprises a VH region comprising a CDR1 comprising a sequence having at least 80% sequence identity with GYYMS (SEQ ID NO: 4).

In one embodiment, the BMP1, TLL1 and/or TLL2 antigen binding protein, such as anti-BMP1, TLL1 and/or TLL2 antibody or fragment thereof, comprises a VH region comprising a CDR2 comprising a sequence having at least 80% sequence identity with WINPLSGETNYAQKFQG (SEQ ID NO: 5).

In one embodiment, the BMP1, TLL1 and/or TLL2 antigen binding protein, such as anti-BMP1, TLL1 and/or TLL2 antibody or fragment thereof, comprises a VH region comprising a CDR3 comprising a sequence having at least 80% sequence identity with DTGELDGMNWYFDL (SEQ ID NO: 6).

In one embodiment, the BMP1, TLL1 and/or TLL2 antigen binding protein, such as anti-BMP1, TLL1 and/or TLL2 antibody or fragment thereof, comprises a VH region comprising a CDR1 comprising a sequence of GYYMS (SEQ ID NO: 4), a CDR2 comprising a sequence of WINPLSGETNYAQKFQG (SEQ ID NO: 5) and a CDR3 comprising a sequence of DTGELDGMNWYFDL (SEQ ID NO: 6).

In one embodiment, the BMP1, TLL1 and/or TLL2 antigen binding protein, such as anti-BMP1, TLL1 and/or TLL2 antibody or fragment thereof, comprises a VL region comprising a CDR1 comprising a sequence having at least 80% sequence identity with RASQSVSSYLA (SEQ ID NO: 1).

In one embodiment, the BMP1, TLL1 and/or TLL2 antigen binding protein, such as anti-BMP1, TLL1 and/or TLL2 antibody or fragment thereof, comprises a VL region comprising a CDR2 comprising a sequence having at least 80% sequence identity with DASNRAT (SEQ ID NO: 2).

In one embodiment, the BMP1, TLL1 and/or TLL2 antigen binding protein, such as anti-BMP1, TLL1 and/or TLL2 antibody or fragment thereof, comprises a VL region comprising a CDR3 comprising a sequence having at least 80% sequence identity with QQSDSWPPT (SEQ ID NO: 3).

In one embodiment, the BMP1, TLL1 and/or TLL2 antigen binding protein, such as anti-BMP1, TLL1 and/or TLL2 antibody or fragment thereof, comprises a VL region comprising a CDR1 comprising a sequence of RASQSVSSYLA (SEQ ID NO: 1), a CDR2 comprising a sequence of DASNRAT (SEQ ID NO: 2) and a CDR3 comprising a sequence of QQSDSWPPT (SEQ ID NO: 3).

In one embodiment, the BMP1, TLL1 and/or TLL2 antigen binding protein, such as anti-BMP1, TLL1 and/or TLL2 antibody or fragment thereof, comprises the following 6 CDRs: LCDR1 of RASQSVSSYLA (SEQ ID NO: 1); LCDR2 of DASNRAT (SEQ ID NO: 2); LCDR3 of QQSDSWPPT (SEQ ID NO: 3); HCDR1 of GYYMS (SEQ ID NO: 4); HCDR2 of WINPLSGETNYAQKFQG (SEQ ID NO: 5); and HCDR3 of DTGELDGMNWYFDL (SEQ ID NO: 6).

According to a further aspect of the invention, there is provided a BMP1, TLL1 and/or TLL2 antigen binding protein, such as anti-BMP1, TLL1 and/or TLL2 antibody or fragment thereof, which comprises a VH region comprising CDR1, CDR2 and CDR3 sequences as defined herein and a VL region comprising CDR1, CDR2 and CDR3 sequences as defined herein.

In one embodiment, the BMP1, TLL1 and/or TLL2 antigen binding protein, such as anti-BMP1, TLL1 and/or TLL2 antibody or fragment thereof, comprises a VL region which comprises LCDR1 of RASQSVSSYLA (SEQ ID NO: 1); LCDR2 of DASNRAT (SEQ ID NO: 2); and LCDR3 of QQSDSWPPT (SEQ ID NO: 3); and a VH region which comprises HCDR1 of GYYMS (SEQ ID NO: 4); HCDR2 of WINPLSGETNYAQKFQG (SEQ ID NO: 5); and HCDR3 of DTGELDGMNWYFDL (SEQ ID NO: 6).

In one embodiment, the BMP1, TLL1 and/or TLL2 antigen binding protein, such as anti-BMP1, TLL1 and/or TLL2 antibody or fragment thereof, comprises a VH region which comprises an amino acid sequence having at least 80% sequence identity with SEQ ID NO: 7.

In one embodiment, the BMP1, TLL1 and/or TLL2 antigen binding protein, such as anti-BMP1, TLL1 and/or TLL2 antibody or fragment thereof, comprises a VL region which comprises an amino acid sequence having at least 80% sequence identity with SEQ ID NO: 8.

In one embodiment, the BMP1, TLL1 and/or TLL2 antigen binding protein, such as anti-BMP1, TLL1 and/or TLL2 antibody or fragment thereof, comprises a VH region which comprises an amino acid sequence having 100% sequence identity with SEQ ID NO: 7.

In one embodiment, the BMP1, TLL1 and/or TLL2 antigen binding protein, such as anti-BMP1, TLL1 and/or TLL2 antibody or fragment thereof, comprises a VL region which comprises an amino acid sequence having 100% sequence identity with SEQ ID NO: 8.

In one embodiment, the BMP1, TLL1 and/or TLL2 antigen binding protein, such as anti-BMP1, TLL1 and/or TLL2 antibody or fragment thereof, comprises a VH region which comprises an amino acid sequence of SEQ ID NO: 7 and a VL region comprising an amino acid sequence of SEQ ID NO: 8.

In one embodiment, the BMP1, TLL1 and/or TLL2 antigen binding protein, such as anti-BMP1, TLL1 and/or TLL2 antibody or fragment thereof, comprises a light chain which comprises an amino acid sequence having at least 80% sequence identity with SEQ ID NO: 9.

In one embodiment, the BMP1, TLL1 and/or TLL2 antigen binding protein, such as anti-BMP1, TLL1 and/or TLL2 antibody or fragment thereof, comprises a heavy chain which comprises an amino acid sequence having at least 80% sequence identity with SEQ ID NO: 10.

In one embodiment, the BMP1, TLL1 and/or TLL2 antigen binding protein, such as anti-BMP1, TLL1 and/or TLL2 antibody or fragment thereof, comprises a light chain which comprises an amino acid sequence having 100% sequence identity with SEQ ID NO: 9.

In one embodiment, the BMP1, TLL1 and/or TLL2 antigen binding protein, such as anti-BMP1, TLL1 and/or TLL2 antibody or fragment thereof, comprises a heavy chain which comprises an amino acid sequence having 100% sequence identity with SEQ ID NO: 10.

In one embodiment, the BMP1, TLL1 and/or TLL2 antigen binding protein, such as anti-BMP1, TLL1 and/or TLL2 antibody or fragment thereof, comprises a light chain comprising an amino acid sequence of SEQ ID NO: 9 and a heavy chain comprising an amino acid sequence of SEQ ID NO: 10.

In one aspect of the invention, a BMP1, TLL1 and/or TLL2 binding protein is a fully human Fc-disabled monoclonal antibody that binds BMP-1, TLL1 and/or TLL2 selected from the following and defined according to CDR, VH/VL, and/or HC/LC sequences:

13Y039-4B06-4334, as shown in SEQ ID NOS: 1 to 10;
13Y039-3E07-2944, as shown in SEQ ID NOS: 15-24;
13Y039-8F02-2949, as shown in SEQ ID NOS: 33-42;
13Y039-4B06-4376, as shown in SEQ ID NOS: 47-56;
13Y039-4B06-4373, as shown in SEQ ID NOS: 61-70;
13Y039-4B06-4364, as shown in SEQ ID NOS: 75-84;
13Y039-4B06-4351, as shown in SEQ ID NOS: 89-98;
13Y039-4B06-4348, as shown in SEQ ID NOS: 103-112;
13Y039-4B06-4328, as shown in SEQ ID NOS: 117-126;
13Y039-4B06-4327, as shown in SEQ ID NOS: 131-140;
13Y039-4B06-4325, as shown in SEQ ID NOS: 145-154;
13Y039-4B06-4324, as shown in SEQ ID NOS: 159-168;
13Y039-127G03-2890, as shown in SEQ ID NOS: 173-182;
13Y039-152B02-2948, as shown in SEQ ID NOS: 187-196;
13Y039-152B02-2940, as shown in SEQ ID NOS: 201-210; and
13Y039-152B02-2935, as shown in SEQ ID NOS: 215-224.

In a further embodiment, the anti-BMP-1, TLL1 and/or TLL2 antibody is selected from the following and defined according to CDR, VH/VL, and/or HC/LC sequences:

13Y039-4B06-4334, as shown in SEQ ID NOS: 1 to 10;
13Y039-3E07-2944, as shown in SEQ ID NOS: 15-24; and
13Y039-8F02-2949, as shown in SEQ ID NOS: 33-42.

In a further embodiment, the anti-BMP-1, TLL1 and/or TLL2 antibody is selected from the following and defined according to CDR, VH/VL, and/or HC/LC sequences:

13Y039-4B06-4334, as shown in SEQ ID NOS: 1 to 10; and
13Y039-3E07-2944, as shown in SEQ ID NOS: 15-24.

In a yet further embodiment, the anti-BMP-1, TLL1 and/or TLL2 antibody:

13Y039-4B06-4334, as shown in SEQ ID NOS: 1 to 10.

Embodiments which refer herein to "at least 80%" or "80% or greater", will be understood to include all values equal to or greater than 80%, such as 85%, 90%, 95%, 97%, 98%, 99% or 100% sequence identity. In one embodiment, the antigen binding protein, such as antibody or fragment of the invention comprises at least 85%, such as at least 90%, at least 95%, at least 97%, at least 98% or at least 99% sequence identity to the specified sequence.

Binding to Target Antigen

The antigen binding protein of the invention may bind to the catalytic domain of human BMP1 with a binding affinity (KD) as measured by SPR of less than 100 nM. In a further embodiment, the KD is 50 nM or less, such as 10 nM or less. In a yet further embodiment, the KD is less than 5 nM, such as less than 2 nM. For example, according to one aspect, there is provided a human anti-BMP1 antibody which binds to the catalytic domain of BMP1 with a binding affinity (KD) as measured by SPR of less than 2 nM.

The antigen binding protein of the invention may bind to the catalytic domain of human TLL1 with a binding affinity (KD) as measured by SPR of less than 100 nM. In a further embodiment, the KD is 50 nM or less, such as 10 nM or less. In a yet further embodiment, the KD is less than 5 nM, such as less than 2 nM. For example, according to one aspect, there is provided a human anti-TLL1 antibody which binds to the catalytic domain of TLL1 with a binding affinity (KD) as measured by SPR of less than 2 nM.

The antigen binding protein of the invention may bind to the catalytic domain of human TLL2 with a binding affinity (KD) as measured by SPR of less than 100 nM. In a further embodiment, the KD is 50 nM or less, such as 10 nM or less. In a yet further embodiment, the KD is less than 5 nM, such as less than 4 nM. For example, according to one aspect, there is provided a human anti-TLL2 antibody which binds to the catalytic domain of TLL2 with a binding affinity (KD) as measured by SPR of less than 4 nM.

For example, according to one aspect, there is provided a human anti-BMP1, anti-TLL1, and anti-TLL2 antibody which binds to the catalytic domain of BMP1 with a binding affinity (KD) as measured by SPR of less than 2 nM, which binds to the catalytic domain of TLL2 with a binding affinity (KD) as measured by SPR of less than 2 nM and which binds to the catalytic domain of TLL2 with a binding affinity (KD) as measured by SPR of less than 4 nM.

Described herein are other assays which may be used to define antigen binding protein function.

Polynucleotides and Expression Vectors

In one aspect of the invention there is provided a polynucleotide encoding the BMP1, TLL1 and/or TLL2 antigen binding protein described herein.

In one embodiment, the polynucleotide sequence encoding the BMP1, TLL1 and/or TLL2 antigen binding protein comprises a VL comprising a polynucleotide sequence having at least 70% sequence identity with SEQ ID NO: 11.

In one embodiment, the polynucleotide sequence encoding the BMP1, TLL1 and/or TLL2 antigen binding protein comprises a VH chain comprising a polynucleotide sequence having at least 70% sequence identity with SEQ ID NO: 12.

In one embodiment, the polynucleotide sequence encoding the BMP1, TLL1 and/or TLL2 antigen binding protein comprises a heavy chain comprising a polynucleotide sequence having at least 70% sequence identity with SEQ ID NO: 13.

In one embodiment, the polynucleotide sequence encoding the BMP1, TLL1 and/or TLL2 antigen binding protein comprises a light chain comprising a polynucleotide sequence having at least 70% sequence identity with SEQ ID NO: 14.

In one embodiment, the polynucleotide sequence encoding the BMP1, TLL1 and/or TLL2 antigen binding protein consists of a sequence of SEQ ID NO: 13 and/or 14.

To express the antigen binding proteins, such as antibodies, or fragments thereof, polynucleotides encoding partial or full-length light and heavy chains, as described herein, are inserted into expression vectors such that the genes are operatively linked to transcriptional and translational control sequences. Therefore, in one aspect of the invention there is provided an expression vector comprising the polynucleotide sequence as defined herein.

In one embodiment, the expression vector comprises the heavy chain of SEQ ID NO: 13.

In one embodiment, the expression vector comprises the light chain of SEQ ID NO: 14.

In one embodiment, the expression vector comprises the heavy chain of SEQ ID NO: 13 and the light chain of SEQ ID NO: 14.

It will be understood that the nucleotide sequences described herein comprise additional sequences encoding amino acid residues to aid with translation, purification and detection, however alternative sequences may be used depending upon the expression system used. These optional sequences can be removed, modified or substituted if alternate design, translation, purification or detection strategies are adopted.

Mutations can be made to the DNA or cDNA that encode polypeptides which are silent as to the amino acid sequence of the polypeptide, but which provide preferred codons for translation in a particular host. The preferred codons for translation of a nucleic acid in, e.g. *E. coli* and *S. cerevisiae*, as well as mammalian, specifically human, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly, artificial gene synthesis, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity.

Expression vectors include, for example, plasmids, retroviruses, cosmids, yeast artificial chromosomes (YACs) and Epstein-Barr virus (EBV) derived episomes. The polynucleotide is ligated into a vector such that transcriptional and translational control sequences within the vector serve their intended function of regulating the transcription and translation of the polynucleotide. Expression and/or control sequences can include promoters, enhancers, transcription terminators, a start codon (i.e. ATG) 5' to the coding sequence, splicing signals for introns and stop codons. The expression vector and expression control sequences are chosen to be compatible with the expression host cell used. SEQ ID NO: 11-12 comprise the nucleotide sequences encoding single chain variable fragments of the invention, comprising a VH region and a VL region. It will be understood that polynucleotides or expression vectors of the invention may encode the VH region, the VL region or both; or encode the heavy chain, light chain, or both. Therefore, polynucleotides encoding the VH and VL regions (or heavy chain and light chain) can be inserted into separate vectors, alternatively sequences encoding both regions or chains are inserted into the same expression vector. The polynucleotide(s) are inserted into the expression vector by standard methods (e.g. ligation of complementary restriction sites on the polynucleotide and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described herein. The expression vector can also encode a signal peptide that facilitates secretion of the antigen binding protein, such as antibody (or fragment thereof) from a host cell. The polynucleotide may be cloned into the vector such that the signal peptide is linked in-frame to the amino terminus of the antigen binding protein. The signal peptide can be an immunoglobulin signal peptide or a heterologous signal peptide (i.e. a signal peptide from a non-immunoglobulin protein).

In one aspect of the invention there is provided a cell (e.g. a host cell or recombinant host cell) comprising the polynucleotide or expression vector as defined herein. It will be understood that the cell may comprise a first vector encoding the light chain of the antibody or fragment thereof, and a second vector encoding the heavy chain of the antibody or fragment thereof. Alternatively, the heavy and light chains both encoded on the same expression vector may be introduced into the cell.

In one embodiment, the polynucleotide or expression vector encodes a membrane anchor or transmembrane domain fused to the antibody or fragment thereof, wherein the antibody or fragment thereof is presented on an extracellular surface of the cell.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors.

Mammalian cell lines available as hosts for expression are well known in the art and include many immortalized cell lines available from the American Type Culture Collection (ATCC). These include, inter alia, Chinese hamster ovary (CHO) cells, human embryonic kidney (HEK) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Antigen-binding fragments of antibodies such as the scFv and Fv fragments can be isolated and expressed in *E. coli* using methods known in the art.

The antigen binding proteins are produced by culturing the host cells for a period of time sufficient to allow for expression of the antigen binding proteins in the host cells or, more preferably, secretion of the antigen binding proteins into the culture medium in which the host cells are grown. Antigen binding proteins can be recovered from the culture medium using standard protein purification methods.

Antibodies (or fragments) of the invention can be obtained and manipulated using the techniques disclosed for example in Green and Sambrook, *Molecular Cloning: A Laboratory Manual* (2012) 4th Edition Cold Spring Harbour Laboratory Press.

Monoclonal antibodies in particular can be produced using hybridoma technology, by fusing a specific antibody-producing B cell with a myeloma (B cell cancer) cell that is selected for its ability to grow in tissue culture and for an absence of antibody chain synthesis.

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma,
b) culturing the immortalized cells (hybridoma) formed and recovering the cells producing the antibodies having the desired specificity.

Alternatively, the use of a hybridoma cell is not required. Antigen binding proteins capable of binding to the target antigens as described herein may be isolated from a suitable antibody library via routine practice, for example, using the phage display, yeast display, ribosomal display, or mammalian display technology known in the art. Accordingly, monoclonal antibodies in particular can be obtained, for example, by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection, and
d) recovering the antibodies having the desired specificity.

Pharmaceutical Compositions

According to a further aspect, there is provided a composition comprising the BMP1, TLL1 and/or TLL2 binding protein as defined herein. In such embodiments, the composition may comprise the antigen binding protein, optionally in combination with other excipients. Also included are compositions comprising one or more additional active agents (e.g. active agents suitable for treating the diseases mentioned herein).

According to a further aspect, there is provided a pharmaceutical composition comprising the BMP1, TLL1 and/or TLL2 binding protein as defined herein, together with a pharmaceutically acceptable diluent or carrier. The antigen binding proteins described herein can be incorporated into pharmaceutical compositions suitable for administration to a subject. Typically, the pharmaceutical composition comprises an antigen binding protein described herein and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, salts, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or fragment thereof may also be included in pharmaceutical compositions.

The compositions described herein may be in a variety of forms. These include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions to be administered by injection or continuous infusion (examples include, but are not limited to, intravenous, intraperitoneal, intradermal, subcutaneous, intramuscular, intraocular, and intraportal).

The preferred mode of administration is parenteral (e.g. intravenous, subcutaneous, intraperitoneal, intramuscular). In a preferred embodiment, the antigen binding protein is administered by intravenous infusion or injection. In another preferred embodiment, the antigen binding protein is administered by intramuscular or subcutaneous injection. In another preferred embodiment, the antigen binding protein is administered by subcutaneous injection, typically once per month.

Therapeutic compositions typically must be sterile and stable under the conditions of manufacture and storage. The composition can be formulated as a solution, microemulsion, dispersion, liposome, or other ordered structure suitable to high drug concentration.

It is within the scope of the invention to use the pharmaceutical composition of the invention in therapeutic methods for the treatment of diseases as described herein as an adjunct to, or in conjunction with, other established therapies normally used in the treatment of such diseases.

In a further aspect of the invention, the antigen binding protein, composition or pharmaceutical composition is administered sequentially, simultaneously or separately with at least one active agent.

The pharmaceutical composition may be included in a kit containing the antigen binding protein together with other medicaments, and/or with instructions for use. For convenience, the kit may comprise the reagents in predetermined amounts with instructions for use. The kit may also include devices used for administration of the pharmaceutical composition.

The antigen binding protein described herein may also be used in methods of treatment. It will be appreciated by those skilled in the art that references herein to treatment refer to the treatment of established conditions. However, compounds of the invention may, depending on the condition, also be useful in the prevention of certain diseases. The antigen binding protein described herein is used in an effective amount for therapeutic, prophylactic or preventative treatment. A therapeutically effective amount of the antigen binding protein described herein is an amount effective to ameliorate or reduce one or more symptoms of, or to prevent or cure, the disease.

Treatment Methods

According to a further aspect of the invention, there is provided the BMP1, TLL1 and/or TLL2 binding protein as defined herein or the pharmaceutical composition as defined herein, for use as a medicament or for use in therapy.

The antigen binding proteins of the invention neutralize the activity of BMP1, TLL1 and/or TLL2, and may be particularly useful for treatment of diseases associated with BMP1, TLL1 and/or TLL2 activity, including for example treatment of diseases where inhibition of BMP1, TLL1 and/or TLL2 is of therapeutic benefit. For example, the antigen binding proteins of the invention may be particularly useful for treatment of diseases where inhibition of tissue ECM (extracellular matrix) production and/or maturation would be beneficial, or where inhibition of myostatin activity would be beneficial, or where inhibition of fibrosis would be beneficial.

In some embodiments, the disease associated with BMP1, TLL1 and/or TLL2 activity is selected from a fibrosis related disease or disorder, for example diseases associated with pathological fibrotic conditions or diseases (e.g. prevention and regression of fibrosis) in body organs or tissues, e.g., such conditions of the:

heart (e.g., myocardial infarction ("MI"), prevention of heart failure post-MI, heart failure (e.g., heart failure with reduced ejection fraction (HFrEF), heart failure with preserved ejection fraction), cardiac arrhythmias (e.g., atrial fibrillation), cardiac fibrosis (e.g., hypertrophic cardiomyopathy), acute decompensated heart failure, atrial fibrillation);

lung (e.g. chronic obstructive pulmonary disease ("COPD"), pulmonary/lung fibrosis (e.g., idiopathic pulmonary fibrosis ("IPF"), pulmonary arterial hypertension (PAH));

kidney (e.g. diabetic nephropathy, post-acute kidney injury, chronic kidney disease ("CKD"), delayed graft function post-transplantation, renal fibrosis, peritoneal fibrosis and prevention of peritoneal fibrosis in peritoneal dialysis patients (e.g., in end-stage renal patients to delay the time to transition to hemodialysis), focal segmental glomerulosclerosis (FSGS));

liver (e.g. liver cirrhosis, non-alcoholic steatohepatitis ("NASH"), hepatic fibrosis (e.g., post-HCV liver fibrosis));

eye (e.g. glaucoma, corneal scarring);

skeletal muscle (e.g. muscular dystrophies, including Duchenne, Becker, limb-girdle, congenital, facioscapulohumeral, myotonic, oculopharyngeal, distal, and Emery-Dreifuss, repetitive muscle injury);

skin (e.g. keloids, wound healing, adhesions, hypertrophic scarring and other scarring, e.g., associated with burns, surgery or other trauma, Dupuytren's contracture, lymphedema, scleroderma);

the vasculature (e.g. stroke, and collagen vascular diseases such as systemic lupus erythematosus, rheumatoid arthritis and scleroderma); and the nervous system (e.g. spinal cord injury, multiple sclerosis).

In some embodiments, the disease associated with BMP1, TLL1 and/or TLL2 activity is selected from cancer and cancer cell metastasis.

In some embodiments, the disease associated with BMP1, TLL1 and/or TLL2 activity is selected from:

idiopathic pulmonary fibrosis;

hypertrophic cardiomyopathy; and prevention of peritoneal fibrosis in peritoneal dialysis patients.

In one particular embodiment, the disease associated with BMP1, TLL1 and/or TLL2 activity is NASH (Nonalcoholic steatohepatitis). NASH is a subtype of non-alcoholic fatty liver disease characterized by hepatic inflammation and a substantial risk of progression to cirrhosis with more advanced stages of the disease being characterized by inflammation.

In some embodiments, the disease associated with BMP1, TLL1 and/or TLL2 activity is selected from muscular diseases characterized by reduced muscle function and/or mass, e.g., muscular dystrophy (e.g., Duchenne, Becker, limb-girdle, congenital, facioscapulohumeral, myotonic, oculopharyngeal, distal, and Emery-Dreifuss), sarcopenia, and cachexia associated with, e.g., heart failure, CKD, COPD, cancer, or old age.

Accordingly, provided is a BMP1, TLL1 and/or TLL2 binding protein as defined herein or a pharmaceutical composition as defined herein for use in the treatment of a fibrosis related disease or disorder as defined herein.

According to a further aspect, provided is a method for the treatment of a fibrosis related disease or disorder as defined herein in a subject in need thereof, comprising administering to the subject a therapeutically effective amount of a BMP1, TLL1 and/or TLL2 antigen binding protein as defined herein or a pharmaceutical composition as defined herein.

According to a further aspect, provided is use of a BMP1, TLL1 and/or TLL2 binding protein as defined herein, or a pharmaceutical composition as defined herein in the manufacture of a medicament for use in the treatment of a fibrosis related disease or disorder as defined herein.

A BMP1, TLL1 and/or TLL2 binding protein as defined herein can also be used to promote muscle growth and/or improve muscle function, for example in cachectic patient populations to reduce frailty (e.g., for muscle wasting).

Thus, according to a further aspect, provided is a method for promoting muscle growth and/or improving muscle function in a subject in need thereof comprising administering to the subject a therapeutically effective amount of a BMP1, TLL1 and/or TLL2 binding protein as defined herein, or a pharmaceutical composition as defined herein.

According to a further aspect, provided is a BMP1, TLL1 and/or TLL2 binding protein as defined herein, or a pharmaceutical composition as defined herein for use in promoting muscle growth and/or improving muscle function.

According to a further aspect, provided is use of a BMP1, TLL1 and/or TLL2 binding protein as defined herein, or a pharmaceutical composition as defined herein in the manufacture of a medicament for promoting muscle growth and/or improving muscle function.

Other features and advantages of the present invention will be apparent from the description provided herein. It should be understood, however, that the description and the specific examples while indicating preferred embodiments of the invention are given by way of illustration only, since various changes and modifications will become apparent to those skilled in the art. The invention will now be described using the following, non-limiting examples:

EXAMPLES

Antibody Generation and Characterization

An in vitro antibody discovery platform was used to identify and affinity mature a fully human antibody specific for human BMP1/TLL.

Clones from the selection outputs were screened in a series of experiments to understand binding kinetics, potency, and biophysical properties following which a lead panel of 16 monoclonal antibodies with the desired functional properties were selected. The lead panel of 16 antibodies were expressed and purified from HEK293-6E cells for further functionalization and characterization studies. Functional characterization was carried out against recombinant human and ortholog species, as well as human serum & rat plasma (endogenous expression).

Because no effector function is required for the desired mechanism of action, residues L235 and G237 within the CH2 domain of the heavy chain constant region were mutated to alanine residues (LAGA mutations). These mutations have previously been shown to remove the ability of IgG1 antibodies to lyse target cells via ADCC or CDC [Bartholomew et al. (1995). Immunology 85, 41-48; Bret et al. (1997) Immunology 91, 346-353]

13Y039-4B06-4334 and 13Y039-3E07-2944 were selected for in vivo characterisation. These antibodies were cloned as reverse chimeric mAbs with human variable region on the mouse IgG2a LAGA Fc and mouse Kappa (referred to herein as Compound A for 4B06-4334 and Compound B for 3E07-2944) and human variable region on rat IgG2b LAGA Fc and rat Kappa (referred to herein as Compound C for 4B06-4334 and Compound D for 3E07-2944). These reverse chimeras were tested in the AngII/PE efficacy studies described below.

Binding Characterisation of Mammalian Expressed Anti-BMP1/TLL Antibodies

Binding characterisation of mammalian expressed anti-BMP1/TLL antibodies by surface plasmon resonance (SPR).

Binding of HEK Expressed Full Lead Panel to Human BMP1 CD+CUB1 by Surface Plasmon Resonance (SPR)

The 16 lead panel antibodies expressed in HEK cells were evaluated for binding to a truncated version of human BMP containing the catalytic domain and truncated domain (Human BMP1 CD+CUB1 truncated antigen) by SPR using BIACORE T200. HBS-EP+ buffer was used and the experiment run at 25° C. Protein A was immobilised to a CM5 sensor chip via amine coupling. The lead panel antibodies were captured onto protein A surface. Human BMP1 CD+CUB1 was then passed over the captured antibodies at various concentrations. The results are shown in Table 1 below.

TABLE 1

Human antibodies binding to human BMP1 CD + CUB1 truncated antigen. KD values determined via SPR.

| Antibody Clone Name | KD (nM) | Buffer[1] |
|---|---|---|
| 13Y039-3E07-2944 | 4.3 | HBS-EP |
| | 4.25 | HBS-EP |
| | 0.09 | Enzyme Dilution Buffer |
| | 3.66 | HBS-EP |
| | 0.05 | Enzyme Dilution Buffer |
| | 0.02 | Enzyme Dilution Buffer |
| | 0.03 | Enzyme Dilution Buffer |
| 13Y039-8F02-2949 | 1.6 | HBS-EP |
| 13Y039-4B06-4376 | 3.7 | HBS-EP |
| 13Y039-4B06-4373 | 3.3 | HBS-EP |
| 13Y039-4B06-4364 | 2.4 | HBS-EP |
| 13Y039-4B06-4351 | 1.9 | HBS-EP |
| 13Y039-4B06-4348 | 1.5 | HBS-EP |
| 13Y039-4B06-4334 | 0.009 | Enzyme Dilution Buffer |
| | 0.01 | Enzyme Dilution Buffer |
| | 2.5 | HBS-EP |
| | 1.73 | HBS-EP |
| | 0.04 | Enzyme Dilution Buffer |
| 13Y039-4B06-4328 | 2.8 | HBS-EP |
| 13Y039-4B06-4327 | 1.5 | HBS-EP |
| 13Y039-4B06-4325 | 2.8 | HBS-EP |
| 13Y039-4B06-4324 | 3.9 | HBS-EP |
| 13Y039-127G03-2890 | 0.3 | HBS-EP |
| 13Y039-152B02-2948 | 1.4 | HBS-EP |
| 13Y039-152B02-2940 | 1.9 | HBS-EP |
| 13Y039-152B02-2935 | 0.8 | HBS-EP |

[1]Enzyme dilution buffer = HEPES (25 mM), $CaCl_2$ (5 mM), $ZnCl_2$ solution (1 μM) and Brij35 (0.01%); HBS-EP buffer = HEPES (0.2M), NaCl (3M), EDTA (60 mM), polysorbate 20 (1.0%), pH 7.6, supplied as 20X (Teknova); HBS-N buffer = HEPES (0.1M), NaCl (1.5M), supplied as 10X (Cytiva Life Sciences)

The results in Table 1 demonstrate that all 16 antibodies showed binding to human BMP1 CD+CUB1 and demonstrated affinities in the single digit nM range of 0.3-4.3 nM. 13Y039-4B06-4334 and 13Y039-3E07-2944 were further evaluated.

Binding of HEK Expressed Antibodies 13Y039-4B06-4334 and 13Y039-3E07-2944 and Reverse Chimeras to Human TLL2 CD+CUB1 and Mouse BMP1 CD+CUB1 by SPR Both antibodies 13Y039-4B06-4334 and 13Y039-3E07-2944 and the reverse chimeric antibodies were evaluated for binding to human TLL2 CD+CUB1 and mouse BMP1 CD+CUB1 truncated antigens by SPR on a BIACORE T200. Protein A/G was immobilised to a CM5 sensor chip via amine coupling and the antibodies were captured to the protein A/G surface. The antigens were passed over the captured antibody at various concentrations. The measured affinities to human TLL2 CD+CUB1 are shown in Table 2 and the measured affinities to mouse BMP1 CD+CUB1 are shown in Table 3.

TABLE 2

Antibody binding to human TLL2 CD + CUB1 truncated antigen. KD values determined via SPR.

| Ab Clone Name | KD (nM) | Buffer |
|---|---|---|
| 13Y039-3E07-2944 | Non-binder | HBS-EP |
| | Non-binder | HBS-EP |
| 13Y039-4B06-4334 | 3.08 | HBS-EP |

The results in Table 2 demonstrate that 13Y039-4B06-4334 in HBS-EP+ buffer has an affinity of 3.08 nM for human TLL2 CD+CUB1 and that 13Y039-3E07-2944 is a non-binder of human TLL2 CD+CUB1.

TABLE 3

Antibodies binding to mouse BMP1 CD + CUB1 truncated antigen. KD values determined via SPR.

| Ab Clone Name | KD (nM) | Buffer |
|---|---|---|
| 13Y039-3E07-2944 | 6.1 | HBS-EP |
| | 5.23 | HBS-EP |
| 13Y039-4B06-4334 | 1.7 | HBS-EP |

The results in Table 3 demonstrate that affinities of both antibodies for mouse BMP1 CD+CUB1 are within the single digit nM range (1.7-6.1 nM).

Reverse chimeric antibodies with a human variable region on a mouse IgG2a LAGA Fc and mouse constant Kappa region were also evaluated for binding to all CD+CUB1 truncates. These experiments included negative antibody controls of anti RSV mouse IgG2a LAGA Fc with a human variable region and mouse constant Kappa region and anti MOPC21 mouse IgG2a. Both negative controls were non binders to all antigens (see Tables 4, 5 and 6).

Affinities of the reverse chimeras to human BMP1 CD+CUB1 are shown in Table 4. When run in HBS-EP+ the affinities for both antibodies are single digit nM (2.33-5.31 nM). When run in enzyme dilution buffer the affinity is stronger, at double digit pM (40-70 pM). These results are comparable to the human antibody affinities reported in Table 1

Affinities of the reverse chimeras to human TLL2 CD+CUB1 are shown in Table 5. The affinity measured for 13Y039-4B06-4334 was 3.54 nM. 13Y039-3E07-2944 did not bind to human TLL2 CD+CUB1. These results are comparable to the affinities of the human antibodies reported in Table 2

Affinities for the reverse chimeras to mouse BMP1 CD+CUB1 are shown in Table 6. The affinities are in the single digit nM range (0.82-6.2 nM). These results are comparable to the affinities of the human antibodies reported in Table 3.

Both antibody 13Y039-4B06-4334 and its reverse chimera had similar affinity to human BMP1 CD-CUB1, mouse BMP1 CD-CUB1, and human TLL2 CD-CUB1, further supporting the use of the reverse chimera in murine preclinical efficacy studies as a surrogate for 13Y039-4B06-4334.

TABLE 4

Reverse chimeric antibodies with a human variable region on a mouse IgG2a LAGA Fc and mouse constant Kappa region binding to human BMP1 CD + CUB1 truncated antigen. KD values determined via SPR.

| Ab Clone Name | KD (nM) | Buffer |
|---|---|---|
| 13Y039-4B06-4334 human variable region on mouse IgG2a LAGA Fc, mouse cKappa (compound A) | 2.33<br>0.04 | HBS-EP<br>Enzyme Dilution Buffer |
| 13Y039-3E07-2944 human variable region on mouse IgG2a LAGA Fc, mouse cKappa (Compound B) | 0.07<br>5.31 | Enzyme Dilution Buffer<br>HBS-EP |
| Anti RSV human variable region on mouse IgG2a LAGA Fc, mouse cKappa (negative control) | Non-binder<br>Non-binder | HBS-EP<br>Enzyme Dilution Buffer |
| Anti MOPC21 mouse IgG2a (negative control) | Non-binder<br>Non-binder | HBS-EP<br>Enzyme Dilution Buffer |

TABLE 5

Reverse chimeric antibodies with a human variable region on mouse IgG2a LAGA Fc and mouse constant Kappa region, binding to Human TLL2 CD + CUB1 truncated antigen. KD values determined via SPR.

| Ab Clone Name | KD (nM) | Buffer |
|---|---|---|
| 13Y039-4B06-4334 human variable region on mouse IgG2a LAGA Fc, mouse cKappa (Compound A) | 3.55 | HBS-EP |
| 13Y039-3E07-2944 human variable region on mouse IgG2a LAGA Fc, mouse cKappa (Compound B) | Non binder | HBS-EP |
| Anti RSV human variable region on mouse IgG2a LAGA Fc, mouse cKappa (negative control) | Non-binder | HBS-EP |
| Anti MOPC21 mouse IgG2a (negative control) | Non-binder | HBS-EP |

TABLE 6

Reverse chimeric antibodies with a human variable region on mouse IgG2a LAGA Fc and mouse constant Kappa region, binding to mouse BMP1 CD + CUB1 truncated antigen. KD values determined via SPR.

| Ab Clone Name | KD (nM) | Buffer |
|---|---|---|
| 13Y039-4B06-4334 human variable region on mouse IgG2a LAGA Fc, mouse cKappa (Compound A) | 0.82<br>1.98 | HBS-EP<br>HBS-EP |
| 13Y039-3E07-2944 human variable region on mouse IgG2a LAGA Fc, mouse cKappa (Compound B) | 2.66<br>6.2 | HBS-EP<br>HBS-EP |
| Anti RSV human variable region on mouse IgG2a LAGA Fc, mouse cKappa (negative control) | Non-binder<br>Non-binder | HBS-EP<br>HBS-EP |
| Anti MOPC21 mouse IgG2a (negative control) | Non-binder<br>Non-binder | HBS-EP<br>HBS-EP |

Table 7 is a summary of all kinetic and affinity data for the antibody 13Y039-4B06-4334 expressed in HEK cells binding to all CD+CUB1 antigens. This shows that the antibody has single digit nM affinity for all truncated CD+CUB1 targets when run in HBS-EP+ and the affinity is stronger (40 pM) to human BMP1 CD+CUB1 when in enzyme dilution buffer.

TABLE 7

Affinities and kinetics of the human antibody 13Y039-4B06-4334 binding to human BMP1 CD + CUB1, human TLL2 CD + CUB1 and mouse BMP1 CD + CUB1.

| Antigens screened against | Ka (1/Ms) | Kd (1/s) | KD (nM) | Buffer |
|---|---|---|---|---|
| Human BMP1 CD + CUB1 | 2.75E+05 | 6.84E−04 | 2.5 | HBS-EP |
| | 3.67E+05 | 6.37E−04 | 1.73 | HBS-EP |
| | 6.95E+06 | 2.49E−04 | 0.04 | Enzyme Dilution Buffer |
| Human TLL2 CD + CUB1 | 3.50E+05 | 10.77E−04 | 3.08 | HBS-EP |
| Mouse BMP1 CD + CUB1 | 4.40E+05 | 7.47E−04 | 1.7 | HBS-EP |

Binding of Anti BMP1/TLL Antibody 13Y039-4B06-4334 to Full Length Human and Orthologue Species of BMP1/TLL Antigens by Surface Plasmon Resonance (SPR)

13Y039-4B06-4334 was expressed in CHO cells and tested for binding to all full length BMP1 and TLL antigens across human and all orthologue species (cyno, rat and mouse). The proteins used in this assay were recombinant versions of naturally occurring proteins, as compared to the truncated antigens used in the selection assays described above. Results were generated in two buffers: HBS-EP+ and HBS-N+5 mM $CaCl_2$ and 1 μM $ZnCl_2$. Protein A was immobilised to a CM5 sensor chip via amine coupling and the antibodies were captured to the protein A surface. The antigens were diluted in both buffers and passed over the captured antibody at various concentrations.

13Y039-4B06-4334 bound recombinant human BMP1 with an affinity of 23.6 pM, TLL1 with an affinity of 880 pM, and TLL2 with an affinity of 4270 pM. High affinity binding was dependent upon the addition of $Zn^{2+}$ and $Ca^{2+}$, consistent with the importance of these cations in enzyme structure and function.

The results are shown in Table 8.

TABLE 8

Binding of anti BMP1/TLL antibody 13Y039-4B06-4334 to full length human and orthologue species of BMP1/TLL antigens.

| Antigen | KD in HBS-EP (M) | Average KD in HBS-EP (M) | KD in HBS-N + $CaCl_2$ and $ZnCl_2$ (M) | Average KD in HBS-N + $CaCl_2$ and $ZnCl_2$ (M) |
|---|---|---|---|---|
| Human BMP1-1 | 3.37E-09<br>2.38E-09 | 2.87E-09 | 3.25E-11<br>1.46E-11 | 2.36E-11 |
| Mouse BMP1-3: 126-707* | 9.77E-09<br>1.46E-08 | 1.22E-08 | 3.80E-10<br>1.50E-10 | 2.65E-10 |
| Human TLL1 | 1.15E-08<br>1.73E-08 | 1.44E-08 | 7.10E-10<br>1.05E-09 | 8.80E-10 |
| Cyno TLL1 | 1.13E-08<br>2.91E-08 | 2.02E-08 | 5.00E-13<br>7.80E-13 | 6.40E-13 |
| Mouse TLL1 | 4.56E+09<br>4.93E-09 | 4.74E-09 | 1.08E-09<br>1.22E-09 | 1.15E-09 |
| Rat TLL1 | 6.37E-09<br>9.09E-09 | 7.73E-09 | 8.00E-10<br>1.58E-09 | 1.19E-09 |
| Human TLL2 | NA[1]<br>NA | NA | 4.45E-09<br>4.10E-09 | 4.27E-09 |
| Cyno TLL2 | 2.80E-08<br>3.69E-08 | 3.25E-08 | 6.86E-09<br>6.01E-09 | 6.44E-09 |
| Rat TLL2 | 9.47E-09<br>7.95E-09 | 8.71E-09 | 2.90E-10<br>2.70E-10 | 2.80E-10 |

[1]NA = binding data not generated for this enzyme

In Vitro Target Engagement Potency

Screening of Mammalian Expressed Lead Panel of 16 Anti-BMP-1/TLL Monoclonal Antibodies (mAbs), Using FRET Based Assays, for Activity Against Recombinant Human BMP-1-1, Human TLL-1, Mouse BMP-1-3 (707 Truncate), Mouse TLL-1, Rat TLL-1, Rat TLL-2 and Cynomolgus TLL-1 Enzymes Activity of BMP-1/TLL enzymes was detected using assays based on fluorescence resonance energy transfer (FRET). A peptide substrate spanning the BMP1/TLL cleavage site of physiological protein substrate prolysyl oxidase was labeled with two fluorophores, specifically a donor and quencher (acceptor) molecule (hereafter referred to as the "prolysyl oxidase FRET peptide"). When the donor fluorophore is excited by light at its excitation wavelength, a transient higher wavelength light emission is usually produced as the molecule returns to its ground state. However, in the FRET peptide, the close proximity of the acceptor fluorophore results in transfer of this energy versus emission of fluorescence signal and effectively quenches fluorescence. Cleavage of the peptide substrate by an enzyme (in this case BMP-1, TLL-1 or TLL-2 of the relevant species) results in separation of the fluorophores which permits fluorescence emission from the donor fluorophore. Antibody inhibition of BMP1/TLL enzyme mediated breakdown of the peptide was determined by measuring the donor emission.

A serial dilution of antibody samples was prepared in enzyme dilution buffer. The antibody samples were pre-incubated with enzyme (diluted in enzyme dilution buffer) with gentle agitation. Following this pre-incubation, the prolysyl oxidase FRET peptide was added and incubated. After incubation, the enzyme reaction was stopped with EDTA. Fluorescence was measured using an excitation wavelength of 485 nm and an emission wavelength of 535 nm. Screening was performed on the lead panel of 16 antibodies produced in HEK cells. $IC_{50}$ values were calculated and compared (Table 9). In this initial screen the 4B06 family showed effective inhibition of human BMP-1 with $IC_{50}$ values between 0.01 nM and 0.09 nM; which were typically lower than other families tested. Initial 13Y039-4B06-4334 $IC_{50}$ values demonstrated effective inhibition across all enzymes: huBMP-1 ($IC_{50}$), 0.03 nM; huTLL-1, 0.02 nM; huTLL-2, 0.03 nM; mTLL-1, 0.06 nM; cynoTLL1, 0.05 nM.

TABLE 9

Summary of initial screening of lead panel of antibodies against huBMP-1, huTLL-1, mTLL-1, cynoTLL-1, and huTLL-2.[1]

| Antibody Clone | 62.5 pM huBMP1 $IC_{50}$ (nM) | 250 pM Biotinylated huTLL-1 $IC_{50}$ (nM) | 800 pM Biotinylated mTLL-1 $IC_{50}$ (nM) | 750 pM Biotinylated cynoTLL-1 $IC_{50}$ (nM) | 500 pM huTLL-2 $IC_{50}$ (nM) |
|---|---|---|---|---|---|
| 13Y039-127G03-2890 | 0.40 | 18.20 | 0.88 | 0.22 (AL) | 0.15 (AL) |
| 13Y039-152B02-2935 | 0.25 | 0.09 (AL) | 0.07 (AL) | 0.11 (AL) | 0.20 (AL) |
| 13Y039-152B02-2948 | 0.31 | 0.08 (AL) | 0.11 (AL) | 0.07 (AL) | 0.86 |
| 13Y039-152B02-2940 | 0.13 | 0.05 (AL) | 0.10 (AL) | 0.06 (AL) | 0.28 |
| 13Y039-3E07-2944 | 0.40 | 0.14 | 0.14 (AL) | 0.10 (AL) | ≥398.11 |
| 13Y039-4B06-4324 | 0.02 (AL) | 0.03 (AL) | 0.10 (AL) | 0.07 (AL) | 0.04 (AL) |
| 13Y039-4B06-4325 | 0.03 (AL) | 0.02 (AL) | 0.07 (AL) | 0.05 (AL) | 0.05 (AL) |
| 13Y039-4B06-4327 | 0.01 (AL) | 0.01 (AL) | 0.04 (AL) | 0.02 (AL) | 0.03 (AL) |
| 13Y039-4B06-4328 | 0.03 (AL) | 0.04 (AL) | 0.07 (AL) | 0.07 (AL) | 0.02 (AL) |
| 13Y039-4B06-4334 | 0.03 (AL) | 0.02 (AL) | 0.06 (AL) | 0.05 (AL) | 0.03 (AL) |
| 13Y039-4B06-4348 | 0.02 (AL) | 0.04 (AL) | 0.12 (AL) | 0.18 (AL) | 0.04 (AL) |
| 13Y039-4B06-4351 | 0.03 (AL) | 0.05 (AL) | 0.14 (AL) | 0.13 (AL) | 0.03 (AL) |
| 13Y039-4B06-4364 | 0.02 (AL) | 0.06 (AL) | 0.13 (AL) | 0.11 (AL) | 0.05 (AL) |
| 13Y039-4B06-4373 | 0.09 | 0.04 (AL) | 0.13 (AL) | 0.08 (AL) | 0.10 (AL) |
| 13Y039-4B06-4376 | 0.05 | 0.07 (AL) | 0.16 (AL) | 0.15 (AL) | 0.09 (AL) |
| 13Y039-8F02-2949 | 0.06 | FAIL | 0.56 | 0.02 (AL) | FAIL |

Figure 2:
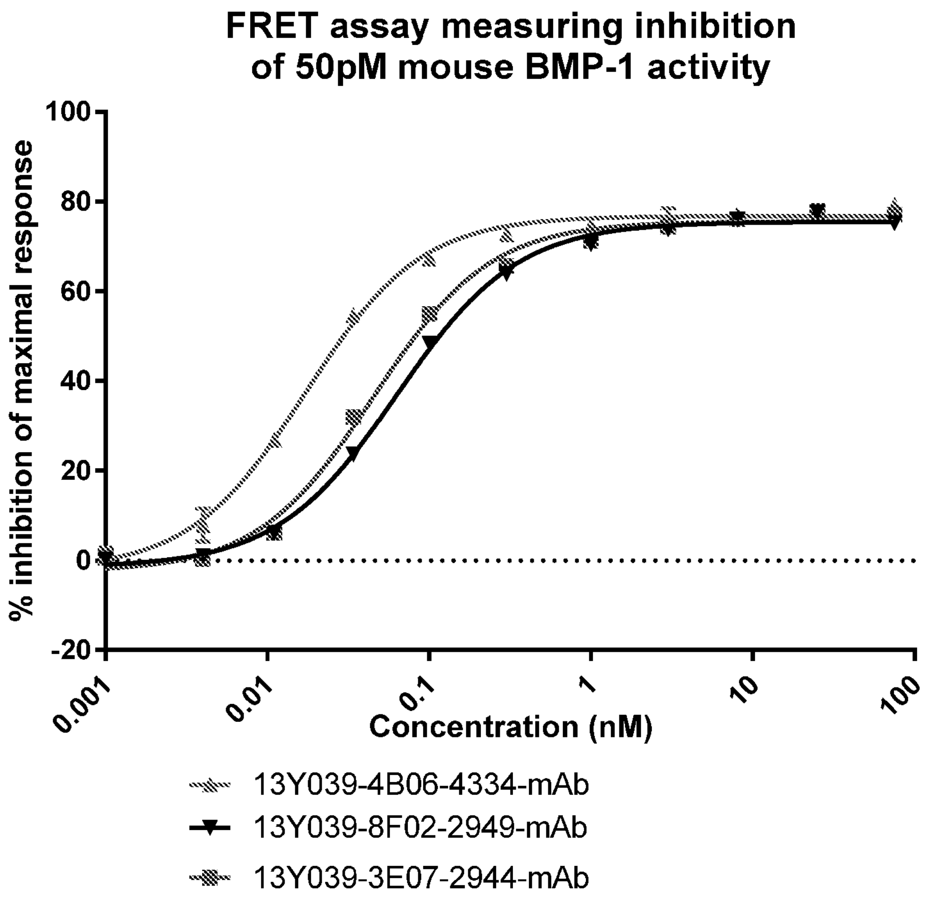
FIG. 2: FRET assay measuring inhibition of 50 pM mouse BMP-1 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 3:
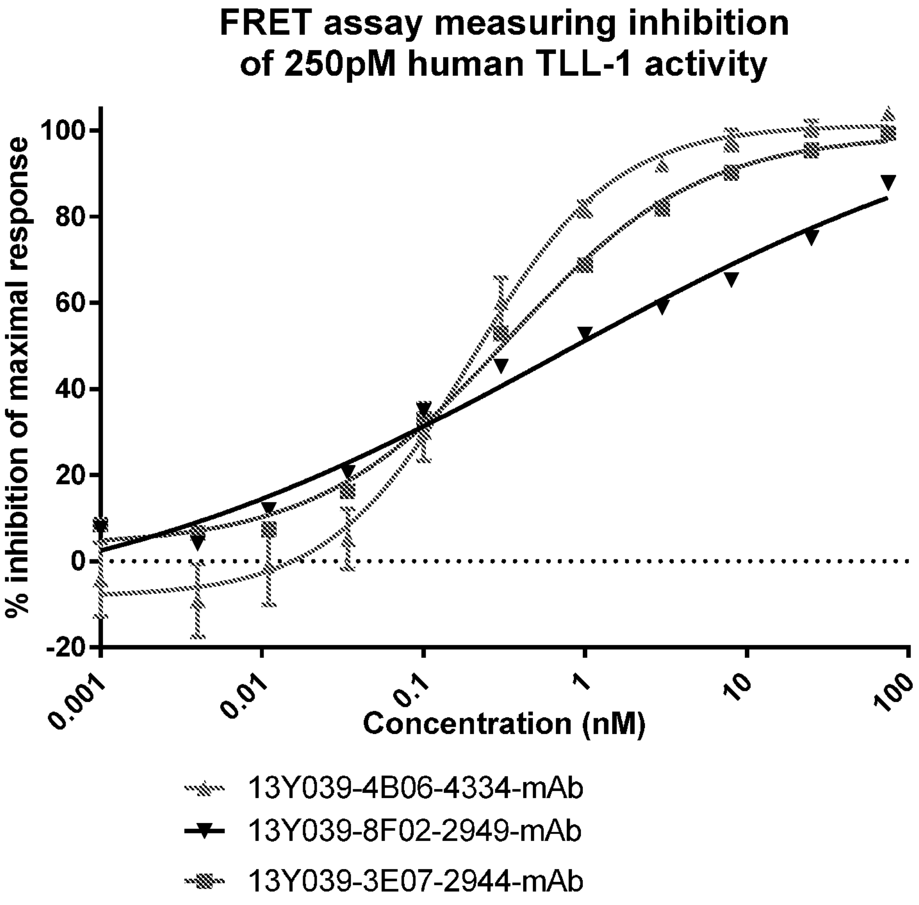
FIG. 3: FRET assay measuring inhibition of 250 pM biotinylated human TLL-1 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 4:
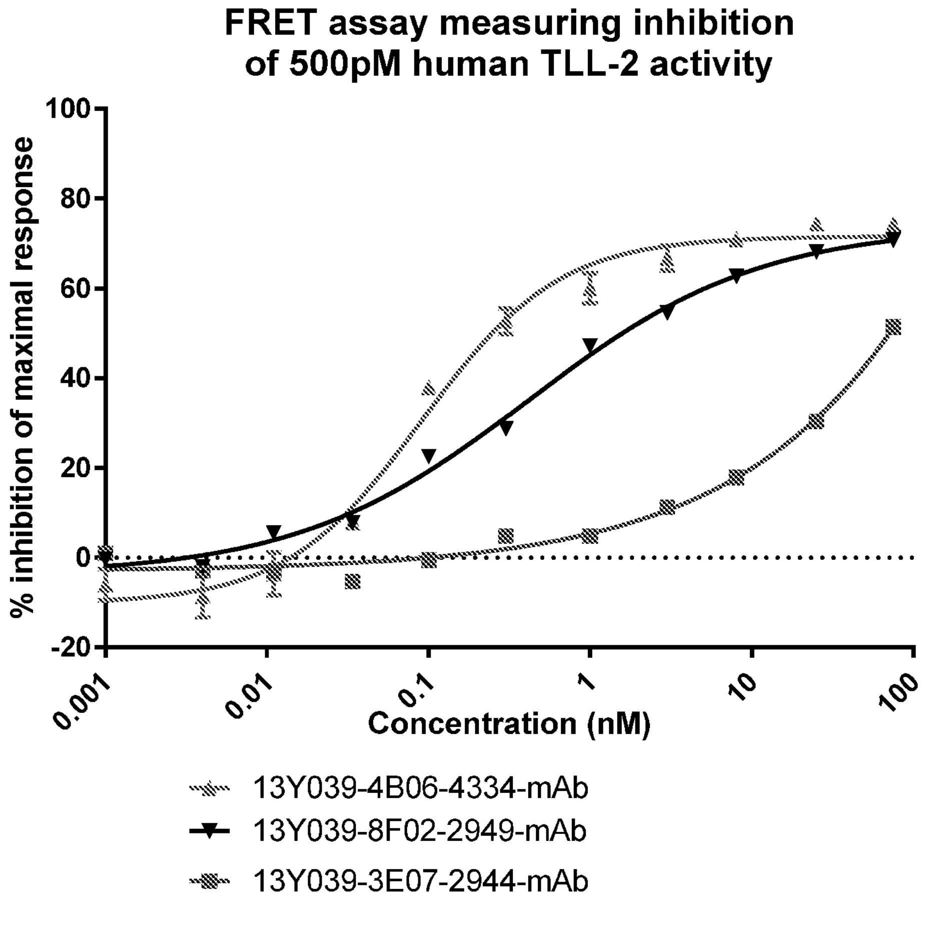
FIG. 4: FRET assay measuring inhibition of 500 pM human TLL-2 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 5:
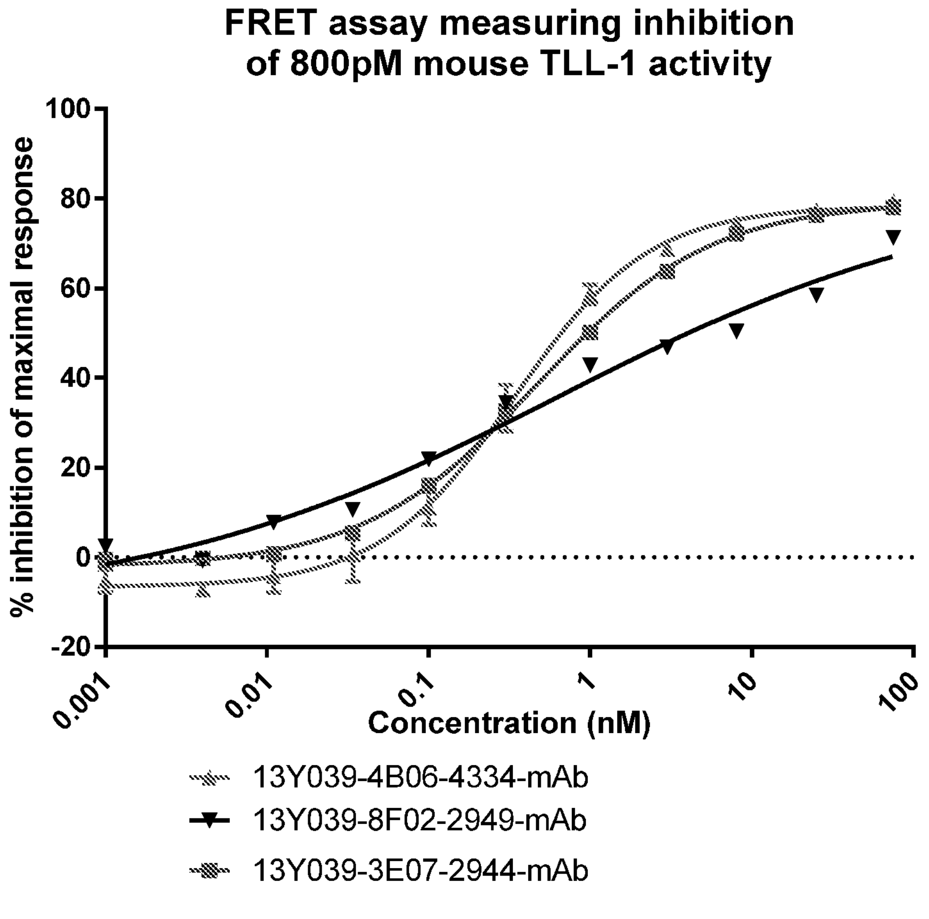
FIG. 5: FRET assay measuring inhibition of 800 pM biotinylated mouse TLL-1 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 6:
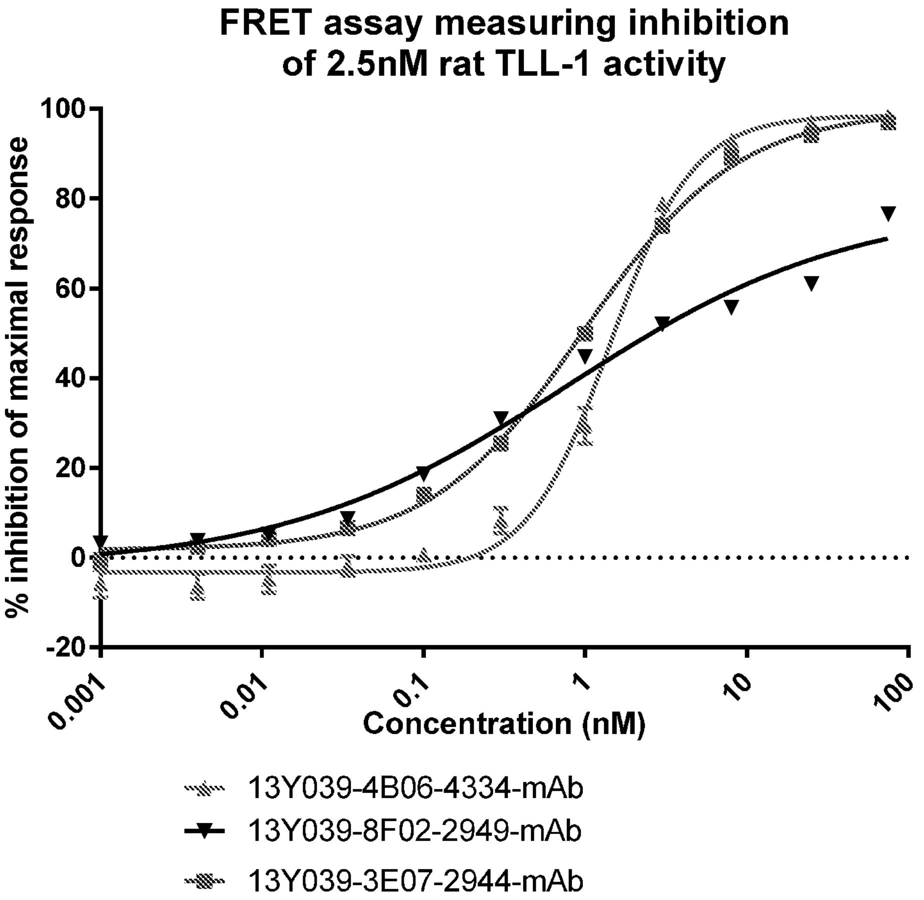
FIG. 6: FRET assay measuring inhibition of 2.5 nM rat TLL-1 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 7:
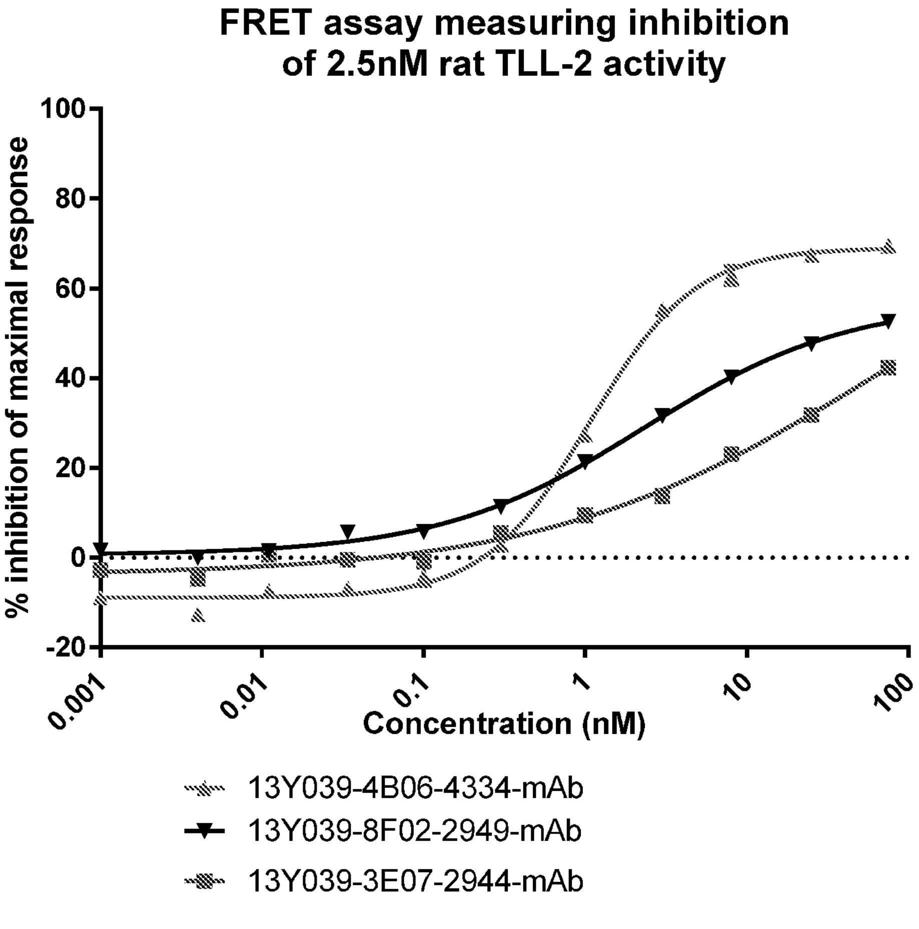
FIG. 7: FRET assay measuring inhibition of 2.5 nM rat TLL-2 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 8:
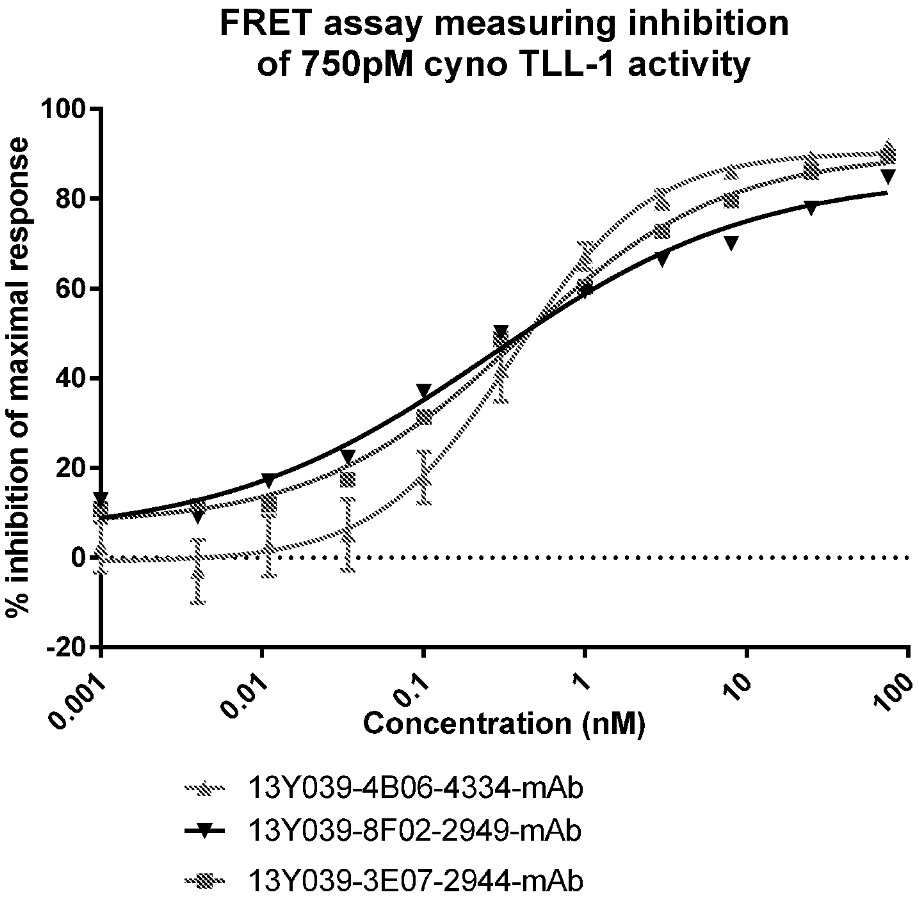
FIG. 8: FRET assay measuring inhibition of 750 pM biotinylated cyno TLL-1 activity by anti-BMP1/TLL antibody molecules. Dose-response curves were plotted for 13Y039-4B06-4334, 13Y039-3E07-2944, and 13Y039-8F02-2949. Molecules were tested from a top concentration of 75 nM with a 3-fold dilution series across 11-points. Figure shows the mean of duplicate data points, with standard deviation as error bars.
Figure 9:
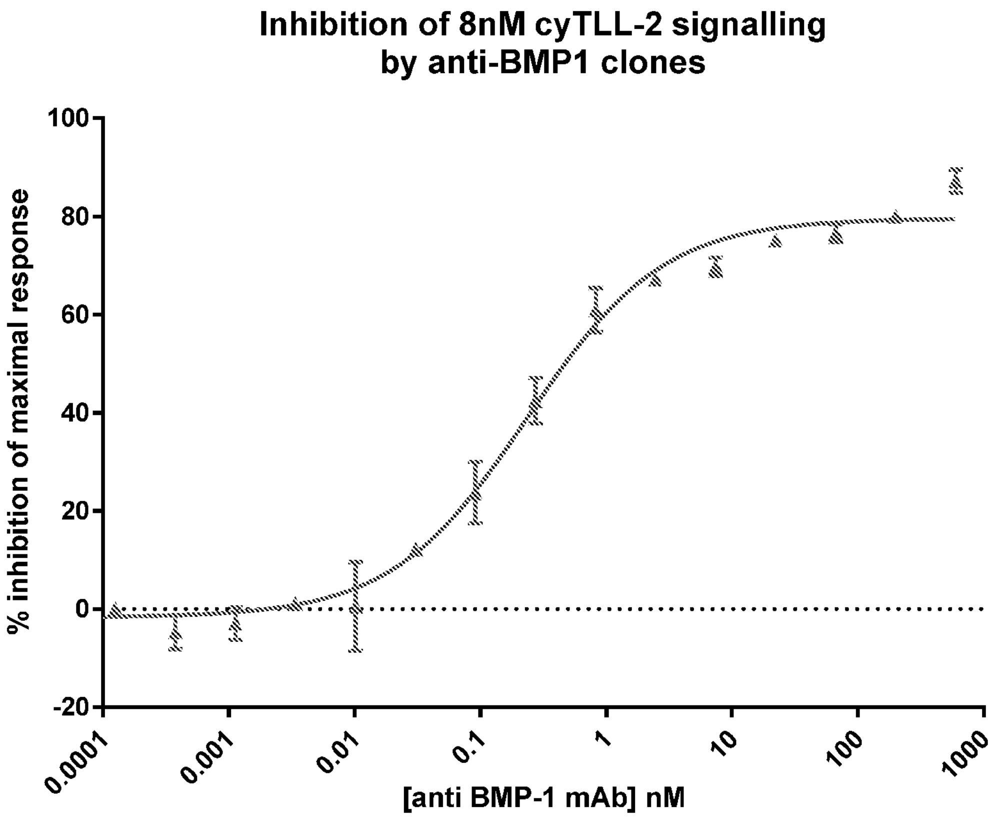
FIG. 9: FRET assay measuring inhibition of 8 nM biotinylated cyno TLL-2 activity by anti-BMP1/TLL antibody molecules. Dose-response curves were plotted for 13Y039-4B06-4334, which was tested from a top concentration of 600 nM with a 3-fold dilution series across 22-points. Figure shows the mean of duplicate data points, with standard deviation as error bars.

[1]"(AL)" indicates that the measured IC50 value was below the assay limit, meaning that any difference in these values may not be significantly different from one another as the assay is not sensitive enough to separate the molecules Three antibodies were further characterized: 13Y039-3E07-2944, 13Y039-8F02-2949, and 13Y039-41B06-4334. They were tested to investigate inhibition of huBMP-1, mBMP-1, huTLL-1, huTLL-2, mTLL-1, ratTLL-1, rat-TLL-2 cynoTLL-1, and cynoTLL-2 activity. Full dose-response curves were plotted for each enzyme, with a representative graph for each enzyme shown in FIGS. 1-9 (FIG. 1, huBMP-1; FIG. 2, mBMP-1; FIG. 3, huTLL-1; FIG. 4, huTLL-2; FIG. 5, mTLL-1; FIG. 6, ratTLL-1; FIG. 7, rat TLL-2; FIG. 8, cynoTLL-1; FIG. 9, cynoTLL-2).

Antibody 13Y039-4B06-4334 inhibited all enzymes tested. $IC_{50}$ values across all experiments are shown in Table 10, with mean and standard deviation calculated. The mean $IC_{50}$ values for each enzyme were: huBMP-1, 0.04 nM; huTLL-1, 0.05 nM; huTLL-2, 0.05 nM; mBMP-1, 0.02 nM; mTLL-1, 0.23 nM; ratTLL-1, 0.50 nM; ratTLL-2, 0.67 nM; cynoTLL-1, 0.10 nM; cynoTLL-2, 0.31 nM.

TABLE 10

Summary data table of Antibody 13Y039-4B06-4334 IC50 values across all experiments.

| | 62.5 pM Human BMP-1 $IC_{50}$ (nM) | 250 pM BT Human TLL-1 $IC_{50}$ (nM) | 500 pM Human TLL-2 $IC_{50}$ (nM) | 50 pM Mouse BMP-1 $IC_{50}$ (nM) | 800 pM BT Mouse TLL-1 $IC_{50}$ (nM) | 2.5 nM Rat TLL-1 $IC_{50}$ (nM) | 2.5 nM Rat TLL-2 $IC_{50}$ (nM) | 750 pM BT Cyno TLL-1 $IC_{50}$ (nM) | 8 nM BT Cyno TLL-2 $IC_{50}$ (nM) |
|---|---|---|---|---|---|---|---|---|---|
| 13Y039-4B06-4334-Mean $IC_{50}$ (Standard Deviation) | 0.04 (0.03) | 0.05 (0.03) | 0.05 (0.01) | 0.02 (0.00) | 0.23 (0.12) | 0.50 (0.09) | 0.67 (0.21) | 0.10 (0.04) | 0.31 (0.12) |

13Y039-4B06-4334 was expressed in HEK and CHO cells and inhibition of recombinant human BMP1, human TLL1, and human TLL2 activity by the HEK- and CHO-expressed protein batches was measured by FRET generally as described above. Potencies were comparable between HEK293-expressed and polyclonal CHO-expressed protein batches (Table 11) when profiled against recombinant human BMP1, human TLL1, human TLL2, and human serum.

TABLE 11

Inhibition of recombinant human BMP1, TLL1 and TLL2 and inhibition of human serum BMP1/TLL activity by 13Y039-4B06-4334

| | Human BMP1 $pK_{i,\ app}$ | Human TLL1 $pIC_{50}$ | Human TLL2 $pIC_{50}$ | Human serum $pIC_{50}$ |
|---|---|---|---|---|
| HEK-expressed 13Y039-4B06-4334 | 11.09 ± 0.01 | 10.8 ± 0.5 | 10.6 ± 0.1 | 9.5 ± 0.5 |
| HEK-expressed 13Y039-4B06-4334 | 11.08 ± 0.02 | 10.2± 0.2 | 10.3 ± 0.1 | |
| CHO-expressed 13Y039-4B06-4334 | 11.07 ± 0.11 | 10.4 ± 0.2 | 10.5 ± 0.1 | 9.4 ± 0.2 |

In order to test the biological efficacy of 13Y039-4B06-4334 in preclinical rodent species, reverse chimeras consisting of the variable domain of 13Y039-4B06-4334 fused to the mouse or rat IgG2a Fc-disabled were generated. These constructs were profiled for activity against recombinant human BMP1 and mouse BMP1, as well as human serum, mouse plasma, and rat plasma using the prolysyl oxidase FRET peptide as described above.

The reverse chimeric antibodies and the antibody 13Y039-4B06-4334 had similar pKi, app values in both the recombinant human BMP1 and mouse BMP1 assays, supporting their use in preclinical efficacy studies as a surrogate for 13Y039-4B06-4334. Activity in human serum and mouse or rat plasma was confirmed for 13Y039-4B06-4334 and the reverse chimeric antibodies (Table 12).

TABLE 12

Inhibition of recombinant human BMP1 and BMP1/TLL activity in human serum, mouse plasma, and rat plasma by the reverse chimeras of 13Y039-4B06-4334

| | Human BMP1 $pK_{i,\ app}$ | Mouse BMP1 $pK_{i,\ app}$ | Human serum $pIC_{50}$ | Mouse plasma $pIC_{50}$ | Rat plasma $pIC_{50}$ |
|---|---|---|---|---|---|
| 13Y039-4B06-4334 | 11.7 | 11.1 | 9.5 ± 0.5 (n = 7) | | 9.8 ± 1.1 (n = 2) |
| 13Y039-4B06-4334 reverse chimera mouse IgG2a LAGA (Compound A) | 12.3 | 11.4 | 10.1 (n = 1) | 7.5 (n = 1) | |
| 13Y039-4B06-4334 reverse chimera rat IgG2a LAGA (Compound C) | 11.8 | 11.3 | 8.7 (n = 1) | | 9.1 ± 0.5 (n = 2) |

Binding to Fcγ Receptors, FcRN and C1q

Binding of anti-BMP1/TLL antibodies including 13Y039-4B06-4334 on an hIgG1 LAGA backbone to soluble recombinant Fcγ receptors, FcRn and C1q was determined by surface plasmon resonance (SPR).

The HEK expressed antibodies 13Y039-4B06-4334 and 13Y039-3E07-2944, and the CHO expressed antibody 13Y039-4B06-4334 were assessed for binding to recombinant soluble human Fc gamma receptors (FcγR). Antibodies were analysed against a positive control antibody containing a wild type human IgG1 Fc region (Fix Fc+) and a negative control antibody containing two point mutations (L235A/G237A) in the Fc region which reduce the interaction with Fc gamma receptors (Fix Fc-). Binding of HEK-expressed 13Y039-4B06-4334, CHO-expressed 13Y039-4B06-4334, and HEK-expressed 13Y039-3E07-2944 to human Fcγ receptors, mouse Fcγ receptors, and cynomolgus macaque Fcγ receptors was assessed by SPR with the Fcγ receptor captured on the surface and the antibody to be tested flowed over the receptor at the desired concentration.

As expected with the Fc-disabling mutations, all antibodies having an hIgG1 LAGA backbone did not bind human Fcγ receptors (FcγRI, FcγRIIaH, FcγRIIR, FcγRIIb, FcγRIIIaV, and FcγRIIIaF), mouse Fcγ receptors (FcγRI, FcγRIIb, FcγRIIIa/b, and FcγRIV), or cynomolgus macaque Fcγ receptors (FcγRIIa, FcγRIIb, and FcγRIII), therefore reducing the potential to induce antibody-dependent cytotoxicity (ADCC).

Binding of anti-BMP1/TLL antibodies to the human, cyno, and mouse neonatal Fc receptor FcRn was assessed by SPR. 13Y039-4B06-4334, 13Y039-3E07-2944 and human IgG1 WT control Fix Fc+ were assessed for binding to recombinant soluble human and cyno FcRn. Compound A (13Y039-4B06-4334, mIgG2a LAGA), Compound B (13Y039-3E07-2944, mIgG2a LAGA), anti-RSV mouse IgG2a LAGA, Anti-RSV rat IgG2b LAGA, Compound C (13Y039-4B06-4334 rat IgG2b LAGA), and Compound D (13Y039-3E07-2944 rat IgG2b) were assessed for binding to recombinant soluble mouse FcRn. Fix Fc+, rat IgG2b wild type control and mouse IgG2a control (anti-MOPC) were included. Human and cyno FcRn were tested with hIgG1, and mouse FcRn was tested with rat IgG2b and mIgG2a 13Y039-4B06-4334 and 13Y039-3E07-2944 showed binding to human and cyno FcRn at pH 6 but not at pH 7.4, indicating that the LAGA mutations have not affected binding to human or cyno FcRn. The relative binding affinity of CHO-expressed 13Y039-4B06-4334 for human FcRn was comparable to that of the IgG1 (Fix Fc+) control antibody. Compound A, Compound B and Compound D showed binding to mouse FcRn at pH 6 but not at pH 7.4. Capture of Compound C on the Protein A surface was very unstable, so there was insufficient antibody on the surface to assess binding to mouse FcRn.

Binding of 13Y039-4B06-4334 to human C1q was assessed by SPR with Fix Fc+ and Fix Fc-used as controls. Antibodies were diluted and immobilised via amine coupling to the sensor chip. Human C1q was diluted in HBS-N+10 mM $CaCl_2$ and injected over the immobilized constructs. Fix Fc+ showed binding as expected to C1q (KD=36.3 nM), and Fix Fc− showed no binding to C1q, as is expected for an Fc disabled antibody. 13Y039-4B06-4334 showed binding comparable to the Fix Fc+ control antibody (KD=36.3 nM).

Figure 10:
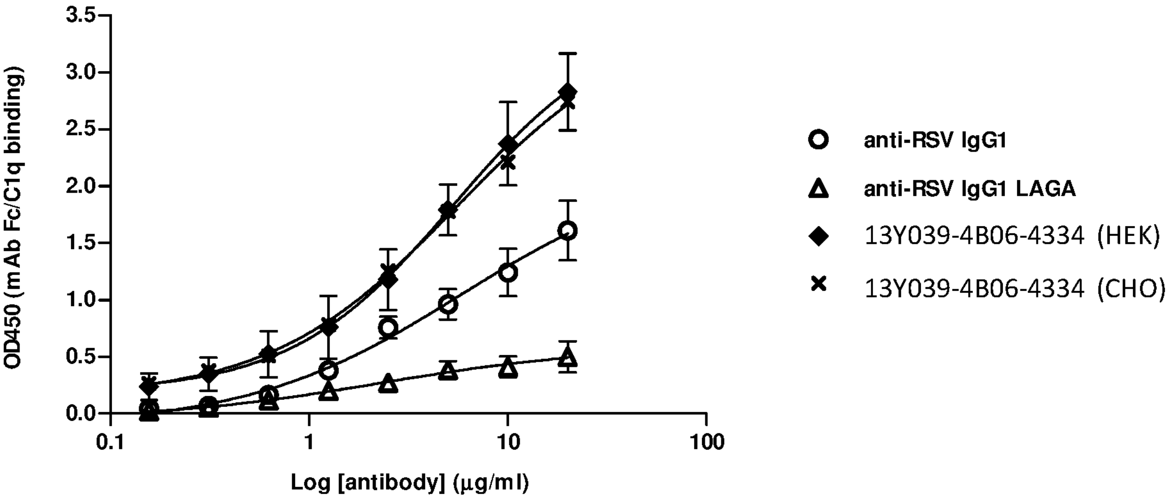
FIG. 10: Binding of 13Y039-4B06-4334 (HEK-expressed and CHO-expressed antibody) to human C1q measured by ELISA.

Binding of 13Y039-4B06-4334 to human C1q was also assessed in an ELISA. Human C1q protein was added to antibody and binding was detected using anti-C1q biotin detection reagent and streptavidin-HRP. The colorimetric signal was detected using SureBlue TMB and the colorimetric reaction was allowed to develop and then measured at 450 nm. The positive control test mAb (anti-RSV IgG1) showed a dose-response effect as expected, while the negative control test mAb (anti-RSV LAGA) showed minimal binding to C1q which was as expected. ELISA confirmed that CHO-expressed 13Y039-4B06-4334 binds to C1q with a similar affinity to the hIgG1 WT control. 13Y039-4B06-4334 expressed in both HEK and CHO cells binds to human C1q at a higher level than the positive binding control antibody, anti-RSV IgG1 with a wildtype Fc. Each data point in FIG. 10 is representative of n=3 experiments with the exception of 13Y039-4B06-4334 expressed in CHO cells which was only repeated once, but data showed that the molecule behaved comparably to the other CHO material, and anti-RSV WT which represents n=2 because of its known binding activity.

Taken together, these results demonstrate that 13Y039-4B06-4334 is Fc disabled with respect to binding to human and cyno Fcγ receptors, although binding is still seen to human C1q. The Fc disabling mutations have not affected binding to human FcRn.

In Vitro Cellular Activity

13Y039-4B06-4334 also inhibits BMP1-catalyzed cleavage of its native substrate, procollagen I, in a fibroblast-based collagen formation assay ("scar-in-a-jar", SIJ). In this assay, stimulation of human primary cardiac fibroblasts with Ficoll induces procollagen formation and cleavage by endogenous BMP1, as measured by the release of procollagen type I C-terminal peptide (PICP). 13Y039-4B06-4334 inhibited PICP formation in a dose-dependent manner, demonstrating that the antibody blocks cleavage of this endogenous protein substrate and attenuates a key element of the fibrosis mechanism in a disease-relevant cell type. Across multiple studies, the average pIC50 value for 13Y039-4B06-4334 in normal human cardiac fibroblasts (NHCFs) was 9.6 (±0.2, n=3).

The mouse reverse chimera for 13Y039-4B06-4334 (compound A) showed activity in the SIJ assay with a pIC50 of 9.8 (±0.6, n=2), comparable to that observed for 13Y039-4B06-4334.

Myostatin Latent Complex Cleavage Assay

Anti-BMP1/TLL antibodies were profiled for inhibition of human BMP-1 in cleaving the myostatin latent complex. Recombinant human BMP-1 was pre-treated with a concentration range of anti-BMP1/TLL antibodies before addition to recombinant human myostatin latent complex. BMP-1 alone cleaved the myostatin latent complex, releasing active myostatin which was measured to indicate the activity of BMP-1. When BMP-1 was pre-incubated with anti BMP1/TLL antibodies, overall its enzymatic activity decreased with an increase in antibody concentration. The levels of myostatin released from the complex were measured in a meso scale discovery (MSD) assay which used an anti-myostatin antibody for capture and detection of the myostatin homodimer. The MSD measurements of the myostatin levels were used to calculate the % inhibition of the anti-BMP1/TLL antibodies.

Figure 11:
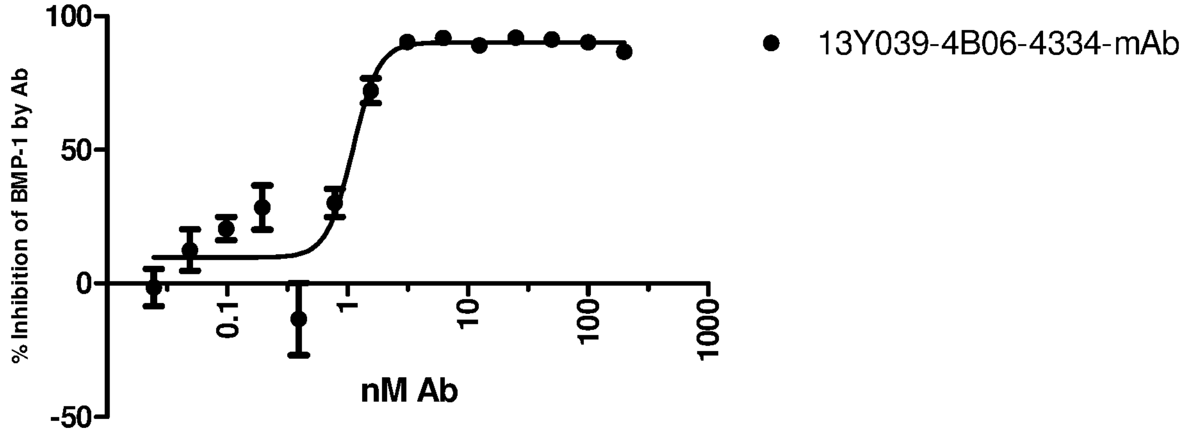
FIG. 11: Inhibition by anti-BMP-1/TLL antibody 13Y039-4B06-4334 of cleavage of latent complex—MSD assay to measure released myostatin.

The data in FIG. 11 shows that the anti-BMP1/TLL antibody 13Y039-4B06-4334 inhibited BMP1 cleavage of the myostatin latent complex in a dose responsive manner. These results confirm that 13Y039-4B06-4334, inhibits BMP1 enzymatic activity as BMP-1 is prevented from cleaving the myostatin latent complex to release myostatin.

In vivo Target Engagement, Pharmacodynamic Markers, Antifibrotic and Anabolic Activity Pharmacodynamic Markers in the Mouse AngII/PE Model Mice administered angiotensin-II (AngII) and phenylephrine (PE) by subcutaneous osmotic pump develop cardiac fibrosis over a two-week treatment period (hereafter referred to as the AngII/PE model). This AngII/PE model was used to evaluate the effect of Compound A, a reverse chimeric construct combining the variable region of 13Y039-4B06-4334 with a murine IgG2a LAGA Fc domain, on pharmacodynamic markers of BMP1 inhibition and cardiac fibrosis.

Figure 12:
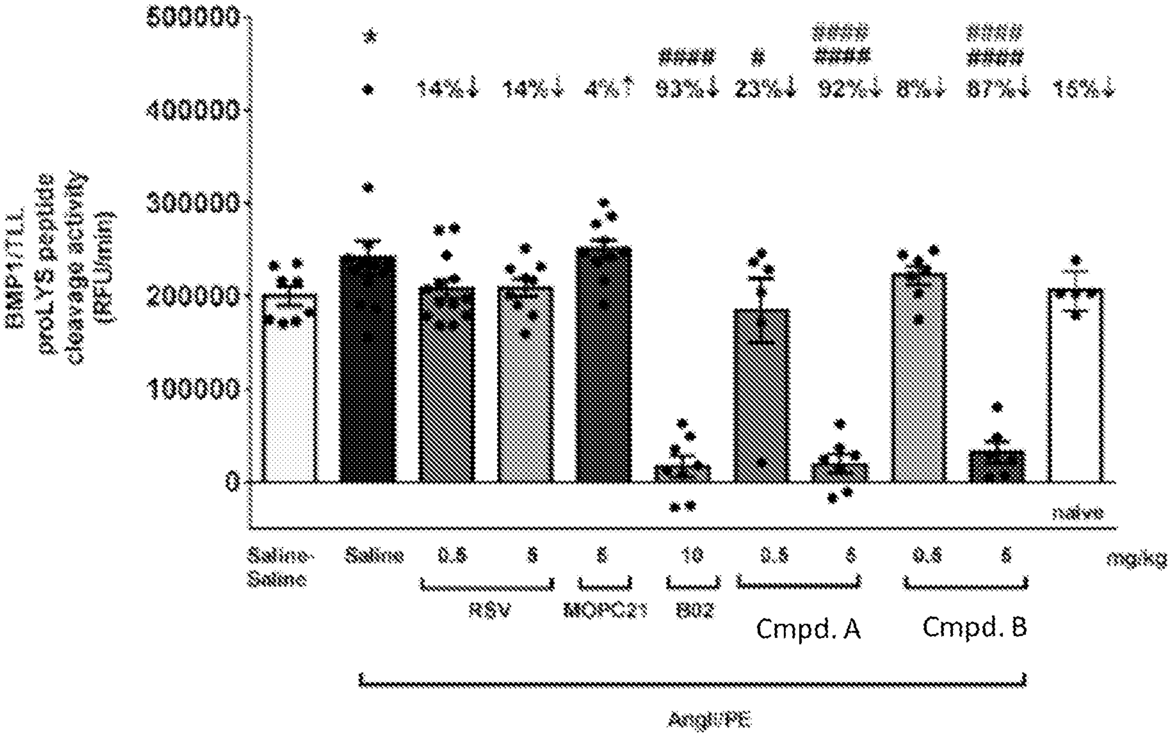
FIG. 12: Plasma BMP1 activity from animals studied in mouse AngII/PE model. For reference, plasma BMP1 levels were determined in naïve mice that had neither received an osmotic pump or i.p. injections (white bar on far right). Compounds A-D are antibodies cloned as reverse chimeric mAbs with human variable region on the mouse IgG2a LAGA Fc and mouse Kappa (referred to herein as Compound A for 4B06-4334 and Compound B for 3E07-2944) and human variable region on rat IgG2b LAGA Fc and rat Kappa (referred to herein as Compound C for 4B06-4334 and Compound D for 3E07-2944). (AngII/PE vs. saline compared by unpaired t-test, *p<0.05; AngII/PE vs. mAb groups compared by one-way ANOVA, #p<0.05, ####p<0.0001; RSV controls vs. dose-paired Compound A or E07, ####p<0.0001).

Starting at the time of osmotic pump implantation, mice were dosed once-weekly for two weeks. The anti-RSV (mouse IgG2a LAGA/mouse cK) and MOPC-21 (mouse variable and constant region mouse IgG2a/mouse cK) antibodies were used as controls. 13Y039-152B02-1 ("B02") is the mouse reverse chimera (human variable region on a mouse IgG2a/mouse cK) tool anti-BMP1/TLL mAb, while Compound B is the mouse reverse chimera (mouse IgG2a LAGA/mouse cK) of another antibody, 13Y039-3E07-2944. In this study, both Compound A/B02 and Compound B inhibited ex vivo BMP1 activity from harvested plasma in a dose-dependent manner (FIG. 12).

Figure 13:
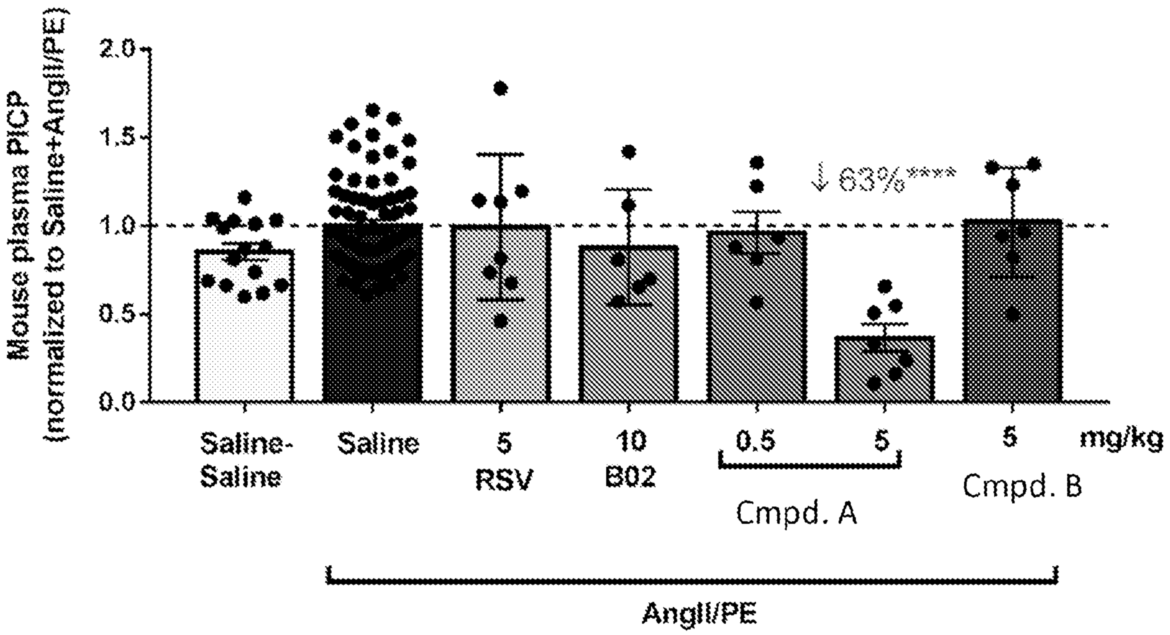
FIG. 13: Plasma PICP measurements from selected groups in the mouse AngII/PE model. PICP levels were measured over multiple immunoblots. Each gel contained all AngII/PE+saline samples, and one of the other test groups. On each gel, all band intensities were normalized to the mean of the respective AngII/PE+saline group. The data were then combined into one graph for visualization. (AngII/PE+saline vs. other groups compared by unpaired t-test, ****p<0.0001).

Using a western blot assay, a significant reduction in circulating procollagen type I C-terminal peptide (PICP) levels in AngII/PE mice treated with 5 mg/kg Compound A was also detected (FIG. 13).

Figure 14:
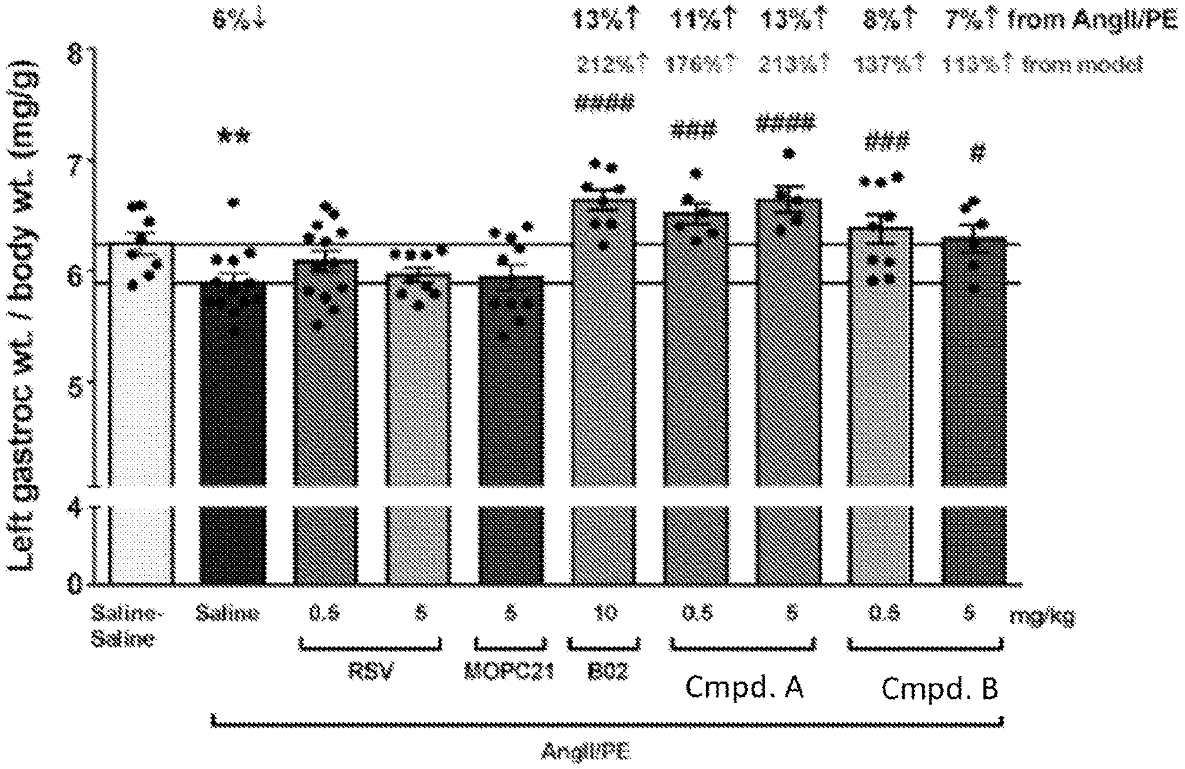
FIG. 14: Effect of Compound A on skeletal muscle mass in the AngII/PE model. Percentages in black above the treatment groups refer to the increase in normalized gastrocnemius weight above AngII/PE group, while the percentages in red refer to the increase above the model window (the difference between the saline-saline group and the AngII/PE-saline group. (AngII/PE vs. saline compared by unpaired t-test, **p<0.01; AngII/PE vs. mAb groups compared by one-way ANOVA, #p<0.05, ###p<0.001, ####p<0.0001).
Figure 15:
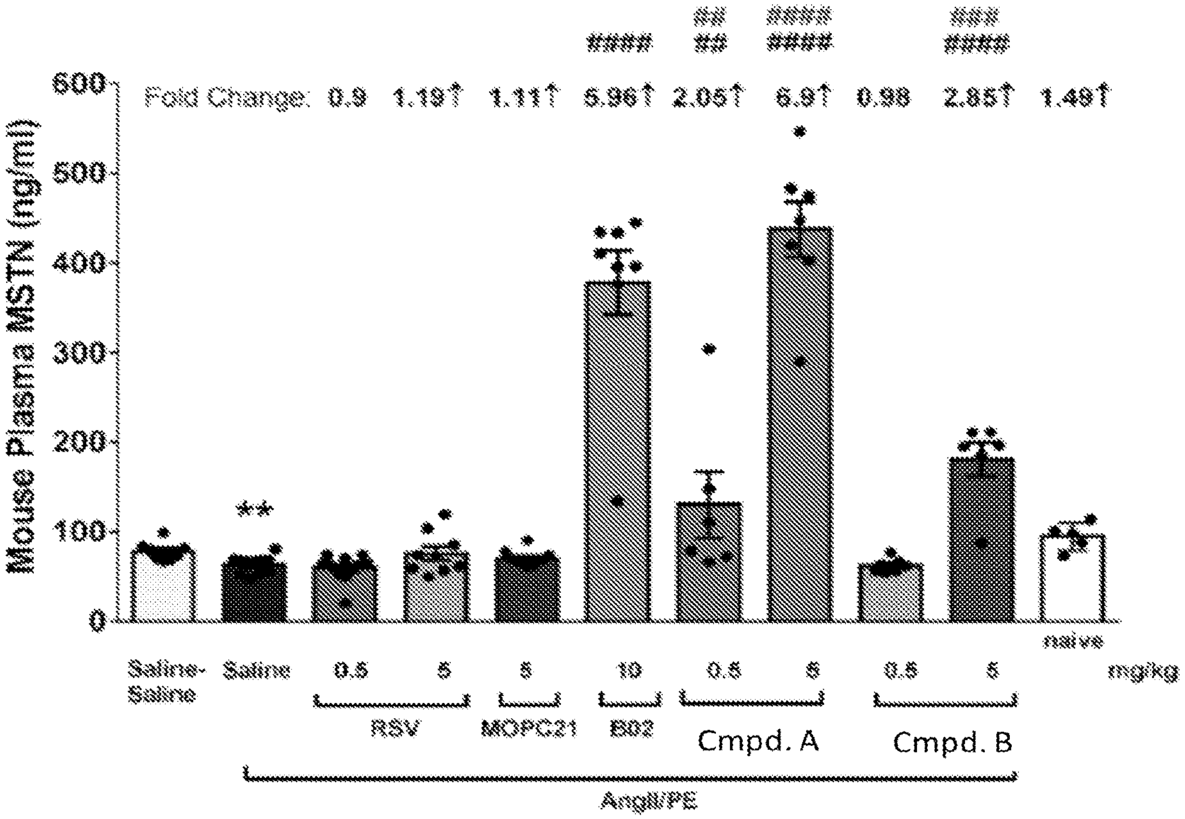
FIG. 15: Effect of Compound A on total plasma myostatin (MSTN) levels in the AngII/PE model. Total plasma myostatin was measured by ELISA. Fold changes are expressed relative to the AngII/PE control. (AngII/PE vs. saline compared by unpaired t-test, **p<0.01; AngII/PE vs. mAb groups compared by one-way ANOVA, ##p<0.01, ####p<0.0001; RSV controls vs. dose-paired Compound A or Compound B, ##p<0.01, ###p<0.001, ####p<0.0001).

An additional effect of Compound A in the mouse AngII/PE model was a significant increase in skeletal muscle mass at high levels of BMP1 inhibition. AngII/PE infusion resulted in a significant reduction in left gastrocnemius weight, normalized to total body weight (6.24±0.10 mg/g vs. 5.89±0.08 mg/g, $p<0.01$, by unpaired t-test). Treatment with Compound A at both 0.5 mg/kg and 5 mg/kg resulted in a restoration of muscle mass to a level greater than the saline osmotic pump control (FIG. 14). Accompanying this observation was an accumulation of total myostatin in the plasma of these animals, as determined using a commercial ELISA assay that detects total (i.e. free and bound) myostatin species (FIG. 15).

Circulating myostatin has been shown to be mostly bound in a latent complex, MSTN-LC, by its inhibitory prodomain fragment (>70% in mouse, with the remainder as other inhibitory complexes; Hill, 2002). Cleavage of the prodomain by BMP1/TLL liberates active myostatin, which signals as a negative growth factor. Thus, the increase in muscle mass and total plasma myostatin levels with Compound A dosing may arise from decreased degradation by BMP1/TLL of the prodomain, and subsequent relief of negative growth regulation that would otherwise accompany release of mature myostatin at local tissue sites in skeletal muscle.

Figure 16:
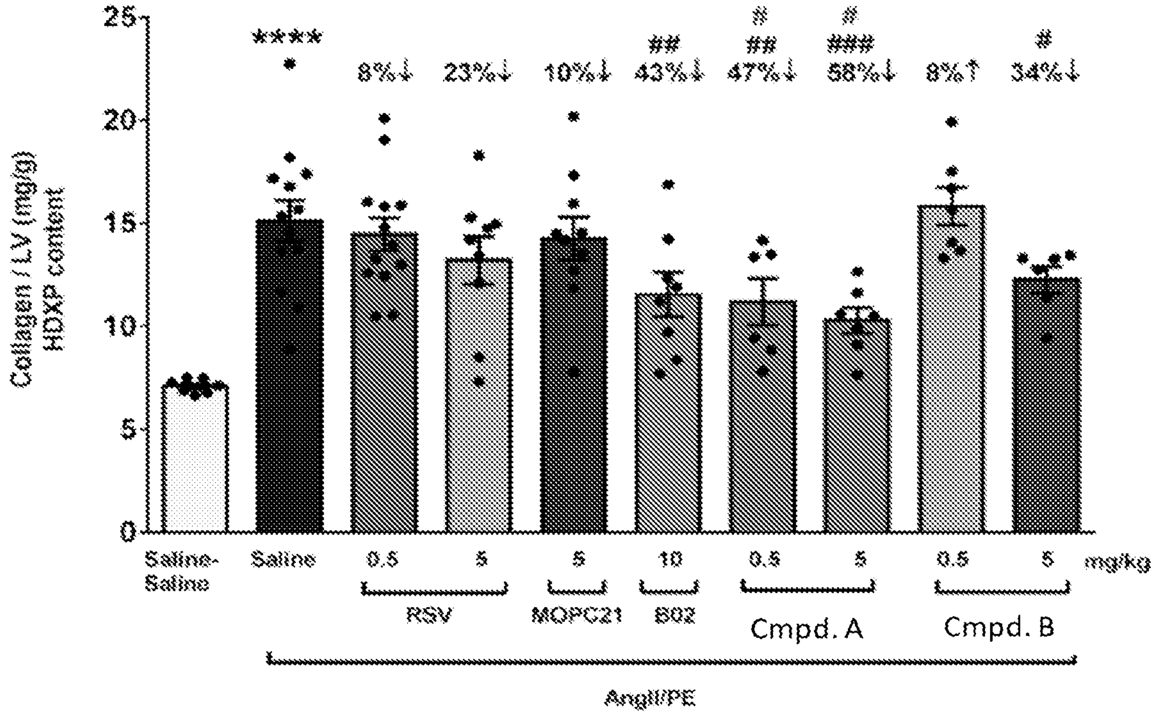
FIG. 16: Left ventricular hydroxyproline (HDXP) content in the mouse AngII/PE study. Percent changes are calculated versus the AngII/PE group. (AngII/PE vs. saline compared by unpaired t-test, ****p<0.0001; AngII/PE vs. mAb groups compared by one-way ANOVA (one-sided), #p<0.05, ##p<0.01, ###p<0.001; RSV controls vs. dose-paired Compound A compared by one-way ANOVA (one-sided), #p<0.05).

Antifibrotic Effects of the Mouse Reverse Chimera (Compound A) in the Murine AngII/PE Model Two-week infusion of AngII/PE in mice leads to a significant increase in collagen production in cardiac tissue, as measured by left ventricular hydroxyproline (HDXP) content (compare the two first bars in FIG. 16), as measured by liquid chromatography/mass spectrometry (LC/MS).

In this model, treatment with Compound A yielded a reduction (47% at 0.5 mg/kg and 58% at 5 mg/kg) in HDXP content that was statistically significant when compared to either the AngII/PE control or the dose-paired anti-RSV mAb controls. Despite the reduction in this fibrosis biomarker, however, no significant change in fibrosis by histopathological analyses was observed.

Effects of the Rat Reverse Chimera (Compound C) in the Dahl Salt-Sensitive Rat Model When fed high-salt chow (8% NaCl), the Dahl salt-sensitive (Dahl S) rat strain rapidly develops hypertension and associated comorbidities, such as renal dysfunction, hyperlipidemia, and insulin resistance. In previous studies, it was shown that this strain also develops cardiac and renal fibrosis.

To assess the cardiac antifibrotic effects of BMP1 inhibition in this model, Dahl S rats were fed 0.3% NaCl chow (normal salt content) until 4-5 weeks of age; this was increased on Day 0 to 1% NaCl chow and then on Day 7 to 8% NaCl chow. 5 mg/kg anti-RSV mAb control, or 5 mg/kg Compound C (the rat reverse chimera of 13Y039-4B06-4334, n=12 for each group) was dosed subcutaneously on a weekly basis from Day 0 to Day 28 and rats were sacrificed on Day 35. The study included a control group (n=12) that received a 0.3% diet and vehicle injections throughout. For both Compound C and the anti-RSV control, exposures at both peak and trough were within the anticipated target range between the rat plasma assay (Table 12) IC90 and IC95 values of 1,180 and 11,800 ng/mL.

Figure 17A:
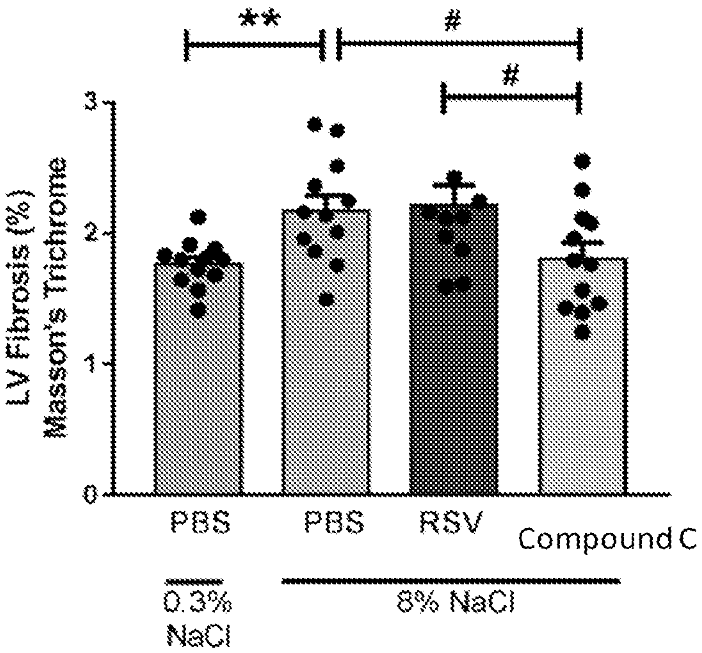
FIGS. 17A and 17B: Effect of Compound C on fibrosis (FIG. 17A) and skeletal muscle mass (FIG. 17B) in the rat Dahl S model.

At the end of the study, sections of the left ventricles were stained with Masson's Trichome to identify fibrotic areas, which were quantified by image analysis. Vehicle-injected rats on 8% NaCl chow exhibited a significant increase in LV fibrosis (~24%) as compared to the normal salt controls, indicating a model effect. Treatment with Compound C, but not the anti-RSV control mAb, yielded a significant reduction (~88%) in LV fibrosis compared to vehicle-treated controls (FIG. 17A).

Figure 17B:
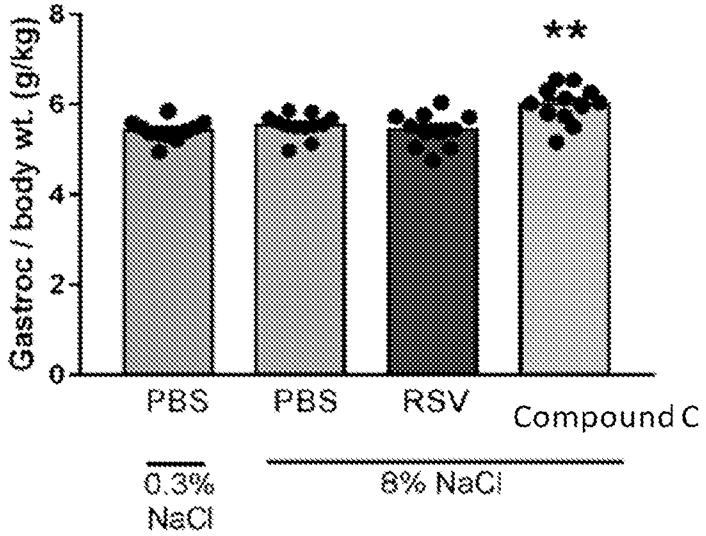

To assess the muscle effects of BMP1 inhibition in this model, the gastrocnemius muscle was isolated and weighed at the end of the study. As had been observed in the AngII/PE model (FIG. 14), treatment with the anti-BMP1 antibody yielded a significant increase (e.g., 9% vs. PBS+8% NaCl) in skeletal muscle mass, when compared to the vehicle or control animals (FIG. 17B).

Figure 18:
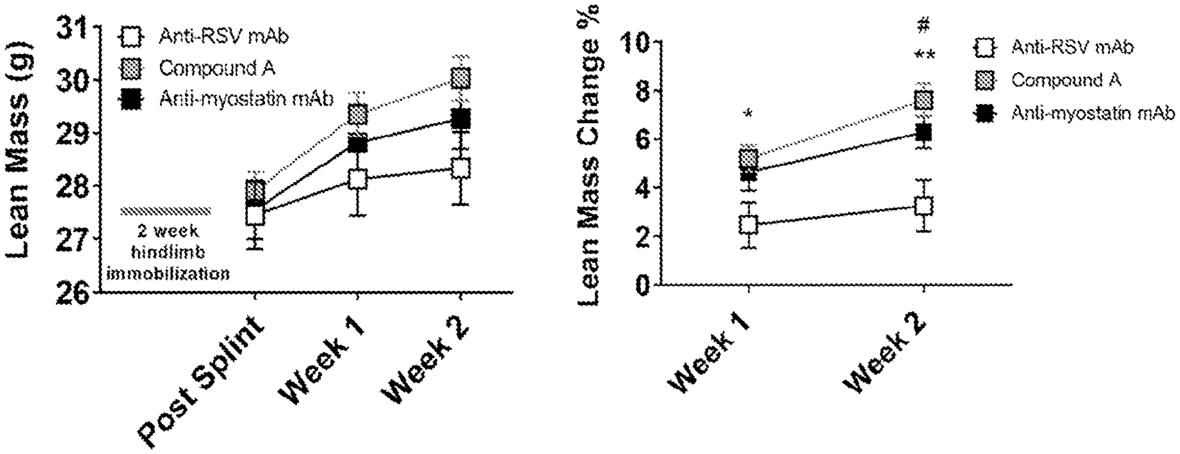
FIG. 18: Lean mass measurements in the 2-week recovery phase after hindlimb immobilization in aged mice. Data are shown as a time-course of absolute lean mass (left) and as percent change relative to the post-splint measurement (right). (Percent lean mass change compared by one-way ANOVA. Compound A vs. anti-RSV mAb: *p<0.05, **p<0.01; anti-myostatin mAb vs. anti-RSV mAb: #p<0.05).

Anabolic Effects of the Mouse Reverse Chimera (Compound A) in the Murine Hindlimb Immobilization Model To assess the effect of BMP1 inhibition on skeletal muscle growth and function, the reverse chimera Compound A was tested in the murine hindlimb immobilization model. In the first study, designed to test muscle recovery after immobilization, aged mice (males, 22 months old) received a splint to immobilize their right hindlimb for 2 weeks. After removal of the splint, the mice were placed in one of three treatment groups and dosed for 2 weeks with either (i) anti-RSV control mAb, 5 mg/kg/week, s.c; (ii)) Compound A, 5 mg/kg/week, s.c; or (iii) anti-myostatin mAb (positive control), 30 mg/kg, 3 doses over 2 weeks, s.c (n-10 per group). Body composition, as measured by quantitative NMR (qNMR), skeletal muscle function, and muscle wet weights were determined after this two-week recovery period. Pharmacodynamic markers associated with BMP1 inhibition were all significantly impacted in the Compound A-treated group, including a 92% reduction in plasma BMP1 activity, a 77% reduction in plasma PICP, and 7.9-fold increase in total myostatin levels. Two-week treatment with Compound A resulted in an ~5% increase in lean mass, significantly greater than that observed with the control anti-RSV mAb (FIG. 18).

Figure 19:
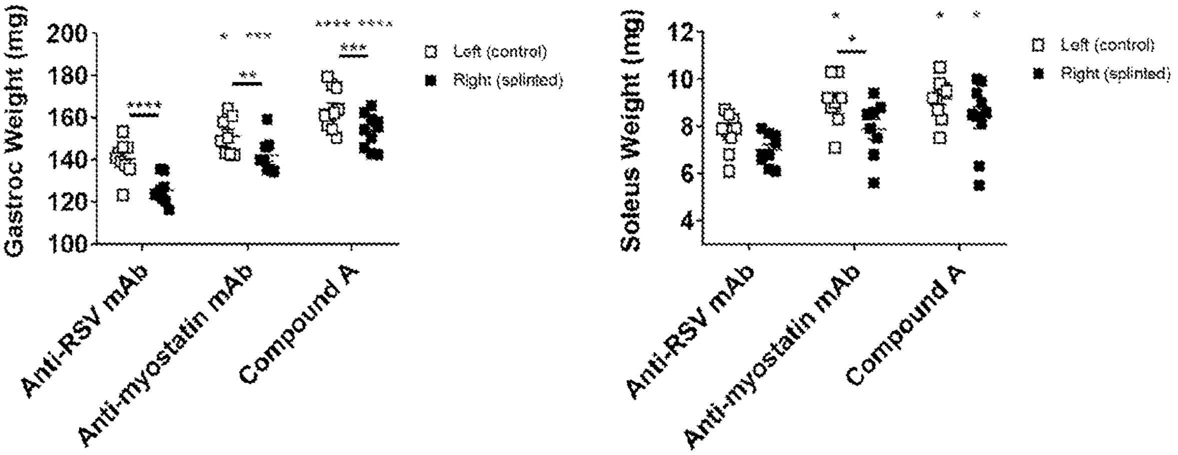
FIG. 19: Gastrocnemius (left) and soleus (right) wet weights measured at the conclusion of the hindlimb immobilization study in aged mice. Empty squares are the weights of the unsplinted left hindlimb, while filled squares are the weights of the splinted right hindlimb. (Muscle weights compared by 2-way ANOVA. Compound A or anti-myostatin mAb vs. anti-RSV mAb in unsplinted limb, *p<0.05, ****p<0.0001; Compound A or anti-myostatin mAb vs. anti-RSV mAb in splinted limb, *p<0.05, *p<0.001, **p<0.0001; Splinted vs. unsplinted limbs, *p<0.05, p<0.01, *p<0.001, ****p<0.0001).

In addition, treatment with Compound A resulted in an increase in gastrocnemius and soleus wet weights in both the control and splinted limbs, as measured at the completion of the 2-week recovery period. This increase was significantly greater than that observed for the control-treated mice (FIG. 19).

Figure 20:
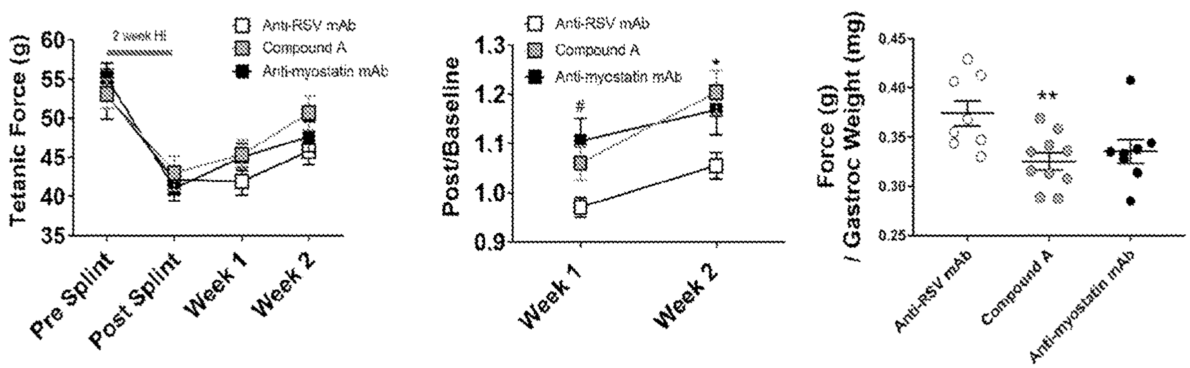
FIG. 20: In vivo muscle contractility measurements determined longitudinally through the hindlimb immobilization study in aged mice. Muscle contractility values are shown as absolute tetanic force measurements (left panel), tetanic force relative to the post-splint value (middle panel) and normalized to the gastrocnemius wet weight (right panel). (Relative tetanic force compared by one-way ANOVA: Compound A vs. anti-RSV mAb, *p<0.05, anti-myostatin mAb vs. anti-RSV mAb, #p<0.05. Normalized force compared by one-way ANOVA, **p<0.01).

Along with the observed increases in muscle mass, which had been previously noted in the AngII/PE model, treatment with Compound A also yielded a significant improvement in muscle function. The increase in muscle mass was not proportional to the increase in force, resulting in a decrease in force:muscle weight ratio (far right panel of FIG. 20), a phenomenon which has been observed in previously generated myostatin knockout mouse strains (Amthor, 2007).

The results from this study demonstrate that inhibition of BMP1/TLL by Compound A not only promotes skeletal muscle growth in recovery from disuse atrophy in aged mice, but also yields an improvement in muscle function.

These results suggest that inhibition of BMP1/TLL by 13Y039-4B06-4334 in the clinical setting would have a benefit in patient populations where frailty and skeletal muscle loss accompany ongoing fibrotic processes.

Pharmacokinetics of 13Y039-4B06-4334

The pharmacokinetics of 13Y039-4B06-4334 were determined following both single and repeat dosing in Wistar Han rats.

Single Dose Pharmacokinetics in Rat

The pharmacokinetics of 13Y039-4B06-4334 were determined following a single intravenous (bolus) or single subcutaneous administration at a nominal dose of 1 mg/kg in Wistar Han rats (n=3).

The individual and mean pharmacokinetic parameters following a single intravenous or subcutaneous administration at 1 mg/kg are presented in Table 13. 13Y039-4B06-4334 is cleared slowly with a mean terminal half-life of approximately 5 days, excluding animal 1, which had a notably faster clearance. The mean volume of distribution, 94 mL/kg, is close to blood volume suggesting the antibody is mainly confined to the systemic circulation.

TABLE 13

The pharmacokinetic parameters of 13Y039-4B06-4334 in Wistar Han rats following a single intravenous or subcutaneous administration at a nominal dose of 1 mg/kg.

| Animal | Cmax (μg/mL) | Tmax (hr) | AUC (hr * μg/mL) | AUCINf (hr * μg/mL) | Half-life (hv) | MRT (hr) | Cl/Cl_F* (mL/hr/kg) | Vss/Vz_F* (mL/kg) |
|---|---|---|---|---|---|---|---|---|
| Intravenous Data | | | | | | | | |
| 4 | 27.2 | 3 | 1870 | 1920 | 129 | 138 | 0.521 | 81.7 |
| 5 | 20.9 | 0.25 | 1830 | 2310 | 117 | 173 | 0.433 | 134 |
| 6 | 24.1 | 0.25 | 1390 | 1410 | 121 | 120 | 0.707 | 94.2 |
| Mean | 24.1 | 0.25** | 1700 | 1880 | 122 | 144 | 0.554 | 103 |
| Subcutaneous Data | | | | | | | | |
| 1 | 8.19 | 72 | 1480 | n/a | n/a | n/a | n/a | n/a |
| 2 | 9.32 | 72 | 1940 | 1990 | 116 | 182 | 0.502 | 83.9 |
| 3 | 7.77 | 72 | 1890 | 1930 | 103 | 191 | 0.519 | 76.8 |
| Mean | 8.43 | 72 | 1770 | 1960 | 110 | 187 | 0.511 | 80.4 |

*CL_F and Vz_F are calculated for subcutaneous administration,

**Median reported

Repeat Dose Pharmacokinetics in Rat

Following weekly subcutaneous dosing at 1 mg/kg for 4 weeks, two of the three animals maintained expected exposure (Cmax and AUC6-168). The level of accumulation (2.9-fold increase in AUC6-168) was as expected for a monoclonal antibody with a 5 day half-life (Table 14). The reduced exposure seen in the third animal could be due to an ADA response, but this could not be confirmed.

TABLE 14

The pharmacokinetic parameters of 13Y039-4B06-4334 in Wistar Han rats following 4 weekly subcutaneous doses of 1 mg/kg.

| | Parameter | Animal 16 | Animal 17 | Animal 18 | Mean |
|---|---|---|---|---|---|
| Week 1 | Cmax (μg/ml) | 6.92 | 5.94 | 5.62 | 6.16 |
| | AUC (hr*μg/ml) | 741 | 708 | 746 | 732 |
| Week 4 | Cmax (μg/ml) | 2.61 | 15.7 | 13.3 | 14.5* |
| | AUC (hr*μg/ml) | 176 | 2320 | 1990 | 2160* |

*Excludes one animal

EMBODIMENTS

Embodiment 1 is a BMP1, TLL1 and/or TLL2 binding protein, which comprises:

(a)(i) any one or a combination of CDRs selected from CDRH1, CDRH2, CDRH3 from SEQ ID NO: 7, 22, 40, 54, 67, 82, 96, 110, 124, 138, 152, 166, 180, 194, 207, and 222 and/or CDRL1, CDRL2, CDRL3 from SEQ ID NO: 8, 21, 39, 53, 68, 81, 95, 109, 123, 137, 151, 165, 179, 193, 208, and 221; or (ii) a CDR variant of (i) wherein the variant has 1, 2, or 3 amino acid modifications; or (b) a VH region comprising a sequence at least 80% identical to the sequence of SEQ ID NO: 7, 22, 40, 54, 67, 82, 96, 110, 124, 138, 152, 166, 180, 194, 207, or 222 and/or a VL region comprising a sequence at least 80% identical to the sequence of SEQ ID NO: 8, 21, 39, 53, 68, 81, 95, 109, 123, 137, 151, 165, 179, 193, 208, or 221.

Embodiment 2 is the BMP1, TLL1 and/or TLL2 binding protein according to embodiment 1, wherein the CDR of (a)(i) is: CDRL1 of SEQ ID NO: 1; CDRL2 of SEQ ID NO: 2; CDRL3 of SEQ ID NO: 3; CDRH1 of SEQ ID NO: 4; CDRH2 of SEQ ID NO: 5; and/or CDRH3 of SEQ ID NO: 6.

Embodiment 3 is the BMP1, TLL1 and/or TLL2 binding protein according to embodiment 1 or 2, comprising one or more of:

a LCDR1 comprising a sequence having at least 80% sequence identity with RASQSVSSYLA (SEQ ID NO: 1); and/or a LCDR2 comprising a sequence having at least 80% sequence identity with DASNRAT (SEQ ID NO: 2); and/or a LCDR3 comprising a sequence having at least 80% sequence identity with QQSDSWPPT (SEQ ID NO: 3); and/or a HCDR1 comprising a sequence having at least 80% sequence identity with GYYMS (SEQ ID NO: 4); and/or a HCDR2 comprising a sequence having at least 80% sequence identity with WINPLSGETNYAQKFQG (SEQ ID NO: 5); and/or a HCDR3 comprising a sequence having at least 80% sequence identity with DTGELDGMNWYFDL (SEQ ID NO: 6).

Embodiment 4 is the BMP1, TLL1 and/or TLL2 binding protein according to any one of embodiments 1 to 3, which comprises a VH region comprising a CDR1 comprising a sequence having at least 80% sequence identity with GYYMS (SEQ ID NO: 4); a CDR2 comprising a sequence having at least 80% sequence identity with WINPLSGETNYAQKFQG (SEQ ID NO: 5); and/or a CDR3 comprising a sequence having at least 80% sequence identity with DTGELDGMNWYFDL (SEQ ID NO: 6).

Embodiment 5 is the BMP1, TLL1 and/or TLL2 binding protein according to any one of embodiments 1 to 4, which comprises a VH region comprising a CDR1 comprising a sequence of GYYMS (SEQ ID NO: 4), a CDR2 comprising a sequence of WINPLSGETNYAQKFQG (SEQ ID NO: 5) and/or a CDR3 comprising a sequence of DTGELDGMNWYFDL (SEQ ID NO: 6).

Embodiment 6 is the BMP1, TLL1 and/or TLL2 binding protein according to any one of embodiments 1 to 5, which comprises a VL region comprising a CDR1 comprising a sequence having at least 80% sequence identity with RASQSVSSYLA (SEQ ID NO: 1); a CDR2 comprising a sequence having at least 80% sequence identity with DASNRAT (SEQ ID NO: 2); and/or a CDR3 comprising a sequence having at least 80% sequence identity with QQSDSWPPT (SEQ ID NO: 3).

Embodiment 7 is the BMP1, TLL1 and/or TLL2 binding protein according to any one of embodiments 1 to 6, which comprises a VL region comprising a CDR1 comprising a sequence of RASQSVSSYLA (SEQ ID NO: 1); a CDR2 comprising a sequence of DASNRAT (SEQ ID NO: 2); and/or a CDR3 comprising a sequence of QQSDSWPPT (SEQ ID NO: 3).

Embodiment 8 is the BMP1, TLL1 and/or TLL2 binding protein according to any one of embodiments 1 to 7, which comprises a LCDR1 comprising a sequence of RASQSVSSYLA (SEQ ID NO: 1), a LCDR2 comprising a sequence of DASNRAT (SEQ ID NO: 2); a LCDR3 comprising a sequence of QQSDSWPPT (SEQ ID NO: 3); a HCDR1 comprising a sequence of GYYMS (SEQ ID NO: 4); a HCDR2 comprising a sequence of WINPLSGETNYAQKFQG (SEQ ID NO: 5); and/or a HCDR3 comprising a sequence of DTGELDGMNWYFDL (SEQ ID NO: 6).

Embodiment 9 the BMP1, TLL1 and/or TLL2 binding protein according to any one of embodiments 1 to 8, wherein all 6 CDRs are present in the binding protein.

Embodiment 10 is a BMP1, TLL1 and/or TLL2 binding protein comprising the following 6 CDRs:

```
LCDR1 of
                              (SEQ ID NO: 1)
RASQSVSSYLA;

LCDR2 of
                              (SEQ ID NO: 2)
DASNRAT;

LCDR3 of
                              (SEQ ID NO: 3)
QQSDSWPPT;

HCDR1 of
                              (SEQ ID NO: 4)
GYYMS;
```

-continued

```
HCDR2 of
                              (SEQ ID NO: 5)
WINPLSGETNYAQKFQG;
and

HCDR3 of
                              (SEQ ID NO: 6)
DTGELDGMNWYFDL.
```

Embodiment 11 is the BMP1, TLL1 and/or TLL2 binding protein according to embodiment 10, wherein the binding protein comprises a VH region that is 80% identical to SEQ ID NO: 7 and/or a VL region that is 80% identical to SEQ ID NO: 8.

Embodiment 12 is the BMP1, TLL1 and/or TLL2 binding protein according to embodiment 10 or embodiment 11, wherein the binding protein comprises a VH region that is 100% identical to SEQ ID NO: 7 and/or a VL region that is 100% identical to SEQ ID NO: 8.

Embodiment 13 is the BMP1, TLL1 and/or TLL2 binding protein according to any one of embodiments 10 to 12, wherein the binding protein comprises a heavy chain (HC) sequence at least 80% identical to SEQ ID NO: 10; and/or a light chain (LC) sequence at least 80% identical to SEQ ID NO: 9.

Embodiment 14 is the BMP1, TLL1 and/or TLL2 binding protein according to any one of embodiments 10 to 13, wherein the binding protein comprises a heavy chain (HC) sequence that is 100% identical to SEQ ID NO: 10; and/or a light chain (LC) sequence that is 100% identical to SEQ ID NO: 9.

Embodiment 15 is a BMP1, TLL1 and/or TLL2 binding protein, which comprises a VH region that is 100% identical to SEQ ID NO: 7 and a VL region that is 100% identical to SEQ ID NO: 8.

Embodiment 16 is the BMP1, TLL1 and/or TLL2 binding protein according to embodiment 15, which comprises a light chain that is 100% identical to SEQ ID NO: 9 and a heavy chain that is 100% identical to SEQ ID NO: 10.

Embodiment 17 is a polynucleotide sequence encoding the BMP1, TLL1 and/or TLL2 binding protein according to any one of embodiments 1 to 16.

Embodiment 18 is the polynucleotide sequence according to embodiment 17, which comprises SEQ ID NO: 13 encoding the heavy chain; and/or SEQ ID NO: 14 encoding the light chain.

Embodiment 19 is an expression vector comprising the polynucleotide sequence as defined in embodiment 17 or embodiment 18.

Embodiment 20 is a recombinant host cell comprising the polynucleotide sequence as defined in embodiment 17 or embodiment 18, or the expression vector as defined in embodiment 19.

Embodiment 21 is a method for the production of a BMP1, TLL1 and/or TLL2 binding protein, which method comprises culturing the recombinant host cell of embodiment 20 under conditions suitable for expression of the polynucleotide sequence or expression vector, whereby a polypeptide comprising the BMP1, TLL1 and/or TLL2 binding protein is produced.

Embodiment 22 is the BMP1, TLL1 and/or TLL2 binding protein produced by the method of embodiment 21.

Embodiment 23 is a pharmaceutical composition comprising the BMP1, TLL1 and/or TLL2 binding protein as defined in any one of embodiments 1 to 16 or embodiment 22, and a pharmaceutically acceptable diluent or carrier.

Embodiment 24 is a pharmaceutical composition according to embodiment 23, comprising the BMP1, TLL1 and/or TLL2 binding protein as defined in embodiment 15 or embodiment 16.

Embodiment 25 is a method for the treatment of a fibrosis related disease or disorder in a subject in need thereof comprising administering to the subject a therapeutically effective amount of the BMP1, TLL1 and/or TLL2 binding protein as defined in any one of embodiments 1 to 16 or embodiment 22, or the pharmaceutical composition as defined in embodiment 23 or embodiment 24 to the subject.

Embodiment 26 is the method according to embodiment 25, wherein the subject is a human.

Embodiment 27 is a BMP1, TLL1 and/or TLL2 binding protein as defined in any one of embodiments 1 to 16 or embodiment 22, or a pharmaceutical composition as defined in embodiment 23 or embodiment 24 for use in therapy.

Embodiment 28 is a BMP1, TLL1 and/or TLL2 binding protein as defined in any one of embodiments 1 to 16 or embodiment 22, or a pharmaceutical composition as defined in embodiment 23 or embodiment 24 for use in the treatment of a fibrosis related disease or disorder.

Embodiment 29 is use of a BMP1, TLL1 and/or TLL2 binding protein as defined in any one of embodiments 1 to 16 or claim 22, or a pharmaceutical composition as defined in embodiment 23 or 24 in the manufacture of a medicament for use in the treatment of a fibrosis related disease or disorder.

Embodiment 30 is the method or use as defined in any one of the preceding claims, wherein the fibrosis related disease or disorder is cardiac fibrosis, pulmonary or lung fibrosis, hepatic fibrosis, renal fibrosis, peritoneal fibrosis, or non-alcoholic steatohepatitis (NASH).

Embodiment 31 is the method or use as defined in embodiment 30, wherein the cardiac fibrosis is hypertrophic cardiomyopathy; and the pulmonary or lung fibrosis is idiopathic pulmonary fibrosis.

Embodiment 32 is a method for promoting muscle growth and/or improving muscle function in a subject in need thereof comprising administering to the subject a therapeutically effective amount of the BMP1, TLL1 and/or TLL2 binding protein as defined in any one of embodiments 1 to 16 or embodiment 22, or the pharmaceutical composition as defined in embodiment 23 or embodiment 24 to the subject.

Embodiment 33 is the method according to embodiment 32, wherein the subject is a human.

Embodiment 34 is a BMP1, TLL1 and/or TLL2 binding protein as defined in any one of embodiments 1 to 16 or embodiment 22, or a pharmaceutical composition as defined in embodiment 23 or embodiment 24 for use in promoting muscle growth and/or improving muscle function.

Embodiment 35 is use of a BMP1, TLL1 and/or TLL2 binding protein as defined in any one of embodiments 1 to 16 or embodiment 22, or a pharmaceutical composition as defined in embodiment 23 or 24 in the manufacture of a medicament for promoting muscle growth and/or improving muscle function.

SEQUENCE LISTING

| SEQ ID NO. | Description | Sequence |
|---|---|---|
| 1 | 13Y039-4B06-4334_LCDR1 | RASQSVSSYLA |
| 2 | 13Y039-4B06-4334_LCDR2 | DASNRAT |
| 3 | 13Y039-4B06-4334_LCDR3 | QQSDSWPPT |
| 4 | 13Y039-4B06-4334_HCDR1 | GYYMS |
| 5 | 13Y039-4B06-4334_HCDR2 | WINPLSGETNYAQKFQG |
| 6 | 13Y039-4B06-4334_HCDR3 | DTGELDGMNWYFDL |
| 7 | 13Y039-4B06-4334_VH | QVQLVQSGAEVKKPGASVKVSCKASGYTFLGYYMSWVRQAPG QGLEWMGWINPLSGETNYAQKFQGRVTMTRDTSISTAYMELS RLRSDDTAVYYCARDTGELDGMNWYFDLWGRGTLVTVSS |
| 8 | 13Y039-4B06-4334_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 9 | 13Y039-4B06-4334-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 10 | 13Y039-4B06-4334-mAb\|heavy_chain\| | QVQLVQSGAEVKKPGASVKVSCKASGYTFLGYYMSWVRQAPG QGLEWMGWINPLSGETNYAQKFQGRVTMTRDTSISTAYMELS RLRSDDTAVYYCARDTGELDGMNWYFDLWGRGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKKVEPKSCDKTHTCPPCPAPELAGAPSVFLFPPKPKDTL |

-continued

SEQUENCE LISTING

| SEQ ID NO. | Description | Sequence |
|---|---|---|
| | | MISRTPEVTCVVVDVSHEDPEVKFNWYVDGVEVHNAKTKPREE<br>QYNSTYRVVSVLTVLHQDWLNGKEYKCKVSNKALPAPIEKTISK<br>AKGQPREPQVYTLPPSRDELTKNQVSLTCLVKGFYPSDIAVEW<br>ESNGQPENNYKTTPPVLDSDGSFFLYSKLTVDKSRWQQGNVF<br>SCSVMHEALHNHYTQKSLSLSPGK |
| 11 | 13Y039-4B06-4334_VL | GAGATCGTGCTGACCCAGAGCCCTGCAACCCTGTCCCTGAG<br>CCCTGGCGAAAGGGCCACTCTGAGCTGCAGGGCCAGCCAG<br>AGCGTGAGCAGCTACCTCGCCTGGTACCAGCAGAAGCCCGG<br>CCAGGCCCCTAGGCTGCTGATCTACGACGCCAGCAACAGGG<br>CCACCGGCATTCCCGCAAGGTTCAGCGGCAGCGGCAGCGG<br>CACCGACTTCACCCTGACCATCAGCAGCCTGGAGCCCGAAG<br>ACTTCGCAGTCTACTACTGCCAGCAGAGCGACAGCTGGCCC<br>CCCACCTTCGGGGGCGGCACCAAGGTGGAGATCAAG |
| 12 | 13Y039-4B06-4334_VH | CAGGTGCAGCTCGTGCAGAGCGGCGCCGAGGTGAAAAAGC<br>CCGGCGCCTCTGTCAAGGTGAGCTGCAAGGCCAGCGGCTA<br>CACCTTCCTGGGCTACTACATGAGCTGGGTGAGGCAGGCTC<br>CCGGACAGGGCCTGGAGTGGATGGGCTGGATCAACCCCCT<br>GAGCGGCGAGACCAACTACGCCCAGAAGTTCCAGGGCAGG<br>GTGACCATGACCAGGGACACCAGCATCAGCACCGCCTACAT<br>GGAACTGAGCAGGCTGAGGAGCGACGACACCGCCGTGTATT<br>ACTGCGCCAGGGACACCGGCGAGCTGGACGGCATGAACTG<br>GTACTTCGACCTGTGGGGCAGGGGCACCCTGGTGACAGTGA<br>GCAGC |
| 13 | 13Y039-4B06-4334_HC | ATGGGCTGGTCCTGCATCATCCTGTTTCTGGTGGCCACCGC<br>CACCGGTGTGCACAGCCAGGTGCAGCTCGTGCAGAGCGGC<br>GCCGAGGTGAAAAAGCCCGGCGCCTCTGTCAAGGTGAGCTG<br>CAAGGCCAGCGGCTACACCTTCCTGGGCTACTACATGAGCT<br>GGGTGAGGCAGGCTCCCGGACAGGGCCTGGAGTGGATGGG<br>CTGGATCAACCCCCTGAGCGGCGAGACCAACTACGCCCAGA<br>AGTTCCAGGGCAGGGTGACCATGACCAGGGACACCAGCATC<br>AGCACCGCCTACATGGAACTGAGCAGGCTGAGGAGCGACGA<br>CACCGCCGTGTATTACTGCGCCAGGGACACCGGCGAGCTG<br>GACGGCATGAACTGGTACTTCGACCTGTGGGGCAGGGGCAC<br>CCTGGTGACAGTGAGCAGCGCCAGCACCAAGGGCCCCAGC<br>GTGTTCCCCCTGGCCCCCAGCAGCAAGAGCACCAGCGGCG<br>GCACAGCCGCCCTGGGCTGCCTGGTGAAGGACTACTTCCCC<br>GAGCCCGTGACCGTGTCCTGGAACAGCGGAGCCCTGACCA<br>GCGGCGTGCACACCTTCCCCGCCGTGCTGCAGAGCAGCGG<br>CCTGTACAGCCTGAGCAGCGTGGTGACCGTGCCCAGCAGCA<br>GCCTGGGCACCCAGACCTACATCTGTAACGTGAACCACAAG<br>CCCAGCAACACCAAGGTGGACAAGAAGGTGGAGCCCAAGAG<br>CTGTGACAAGACCCACACCTGCCCCCCCTGCCCTGCCCCCG<br>AGCTGGCCGGAGCCCCCAGCGTGTTCCTGTTCCCCCCCAAG<br>CCTAAGGACACCCTGATGATCAGCAGAACCCCCGAGGTGAC<br>CTGTGTGGTGGTGGATGTGAGCCACGAGGACCCTGAGGTGA<br>AGTTCAACTGGTACGTGGACGGCGTGGAGGTGCACAATGCC<br>AAGACCAAGCCCAGGGAGGAGCAGTACAACAGCACCTACCG<br>GGTGGTGTCCGTGCTGACCGTGCTGCACCAGGATTGGCTGA<br>ACGGCAAGGAGTACAAGTGTAAGGTGTCCAACAAGGCCCTG<br>CCTGCCCCTATCGAGAAAACCATCAGCAAGGCCAAGGGCCA<br>GCCCAGAGAGCCCCAGGTGTACACCCTGCCCCCTAGCAGAG<br>ATGAGCTGACCAAGAACCAGGTGTCCCTGACCTGCCTGGTG<br>AAGGGCTTCTACCCCAGCGACATCGCCGTGGAGTGGGAGAG<br>CAACGGCCAGCCCGAGAACAACTACAAGACCACCCCCCCTG<br>TGCTGGACAGCGATGGCAGCTTCTTCCTGTACAGCAAGCTG<br>ACCGTGGACAAGAGCAGATGGCAGCAGGGCAACGTGTTCAG<br>CTGCTCCGTGATGCACGAGGCCCTGCACAATCACTACACCC<br>AGAAGAGCCTGAGCCTGTCCCCTGGCAAG |
| 14 | 13Y039-4B06-4334_LC | ATGGGCTGGTCCTGCATCATCCTGTTTCTGGTGGCCACCGC<br>CACCGGTGTGCACAGCGAGATCGTGCTGACCCAGAGCCCTG<br>CAACCCTGTCCCTGAGCCCTGGCGAAAGGGCCACTCTGAGC<br>TGCAGGGCCAGCCAGAGCGTGAGCAGCTACCTCGCCTGGTA<br>CCAGCAGAAGCCCGGCCAGGCCCCTAGGCTGCTGATCTACG<br>ACGCCAGCAACAGGGCCACCGGCATTCCCGCAAGGTTCAGC<br>GGCAGCGGCAGCGGCACCGACTTCACCCTGACCATCAGCA<br>GCCTGGAGCCCGAAGACTTCGCAGTCTACTACTGCCAGCAG<br>AGCGACAGCTGGCCCCCCACCTTCGGGGGCGGCACCAAGG<br>TGGAGATCAAGCGTACGGTGGCCGCCCCCAGCGTGTTCATC<br>TTCCCCCCCAGCGATGAGCAGCTGAAGAGCGGCACCGCCA |

-continued

SEQUENCE LISTING

| SEQ ID NO. | Description | Sequence |
|---|---|---|
| | | GCGTGGTGTGTCTGCTGAACAACTTCTACCCCCGGGAGGCC AAGGTGCAGTGGAAGGTGGACAATGCCCTGCAGAGCGGCAA CAGCCAGGAGAGCGTGACCGAGCAGGACAGCAAGGACTCC ACCTACAGCCTGAGCAGCACCCTGACCCTGAGCAAGGCCGA CTACGAGAAGCACAAGGTGTACGCCTGTGAGGTGACCCACC AGGGCCTGTCCAGCCCCGTGACCAAGAGCTTCAACCGGGG CGAGTGC |
| 15 | 13Y039-3E07-2944_LCDR1 | QASQDIANYLN |
| 16 | 13Y039-3E07-2944_LCDR2 | DASNLET |
| 17 | 13Y039-3E07-2944_LCDR3 | QQADTLPFT |
| 18 | 13Y039-3E07-2944_HCDR1 | GDYWS |
| 19 | 13Y039-3E07-2944_HCDR2 | EIDWSGATNYNPSLKS |
| 20 | 13Y039-3E07-2944_HCDR3 | GGSKELSFDI |
| 21 | 13Y039-3E07-2944_VL | DIQMTQSPSSLSASVGDRVTITCQASQDIANYLNWYQQKPGKA PKLLIYDASNLETGVPSRFSGSGSGTDFTFTISSLQPEDIATYYC QQADTLPFTFGGGTKVEIK |
| 22 | 13Y039-3E07-2944_VH | QVQLQQWGAGLLKPSETLSLTCAVYGGSFFGDYWSWIRQPPG KGLEWIGEIDWSGATNYNPSLKSRVTISVDTSKNQFSLKLSSVT AADTAVYYCARGGSKELSFDIWGQGTMVTVSS |
| 23 | 13Y039-3E07-2944-mAb\|light_chain\| | DIQMTQSPSSLSASVGDRVTITCQASQDIANYLNWYQQKPGKA PKLLIYDASNLETGVPSRFSGSGSGTDFTFTISSLQPEDIATYYC QQADTLPFTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 24 | 13Y039-3E07-2944-mAb\|heavy_chain\| | QVQLQQWGAGLLKPSETLSLTCAVYGGSFFGDYWSWIRQPPG KGLEWIGEIDWSGATNYNPSLKSRVTISVDTSKNQFSLKLSSVT AADTAVYYCARGGSKELSFDIWGQGTMVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELAGAPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGK |
| 25 | 13Y039-3E07-2944\|VL\| | GACATCCAGATGACCCAGTCTCCATCCTCCCTGTCTGCATCT GTAGGAGACAGAGTCACCATCACTTGCCAGGCGAGTCAGGA CATTGCCAACTATTTAAATTGGTATCAGCAGAAACCAGGGAA AGCCCCTAAGCTCCTGATCTACGATGCATCCAATTTGGAAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGCCGATACCCTCCCTTTCACTT TTGGCGGAGGGACCAAGGTTGAGATCAAA |
| 26 | 13Y039-3E07-2944\|VH\| | CAAGTACAATTACAACAGTGGGGAGCTGGTTTATTAAAGCCT TCAGAAACTTTAAGTTTGACCTGTGCTGTTTACGGTGGATCAT TTTTTGGTGATTACTGGAGTTGGATTCGTCAACCACCAGGCA AAGGATTGGAGTGGATCGGTGAGATAGACTGGTCAGGCGCG ACTAACTACAATCCAAGTTTAAAATCCAGGGTTACTATCTCCG TAGACACGTCCAAGAACCAGTTCTCCCTGAAGCTGAGTTCTG TGACCGCCGCAGACACGGCGGTGTACTACTGCGCCAGAGG CGGTTCTAAAGAATTGTCATTCGACATATGGGGTCAGGGTAC AATGGTCACCGTCTCCTCA |
| 27 | 13Y039-3E07-2944-HC | CAAGTACAATTACAACAGTGGGGAGCTGGTTTATTAAAGCCT TCAGAAACTTTAAGTTTGACCTGTGCTGTTTACGGTGGATCAT |

-continued

SEQUENCE LISTING

| SEQ ID NO. | Description | Sequence |
|---|---|---|
| | | TTTTTGGTGATTACTGGAGTTGGATTCGTCAACCACCAGGCA AAGGATTGGAGTGGATCGGTGAGATAGACTGGTCAGGCGCG ACTAACTACAATCCAAGTTTAAAATCCAGGGTTACTATCTCCG TAGACACGTCCAAGAACCAGTTCTCCCTGAAGCTGAGTTCTG TGACCGCCGCAGACACGGCGGTGTACTACTGCGCCAGAGG CGGTTCTAAAGAATTGTCATTCGACATATGGGGTCAGGGTAC AATGGTCACCGTCTCCTCAGCCAGCACCAAGGGCCCCAGCG TGTTCCCCCTGGCCCCCAGCAGCAAGAGCACCAGCGGCGG CACAGCCGCCCTGGGCTGCCTGGTGAAGGACTACTTCCCCG AGCCCGTGACCGTGTCCTGGAACAGCGGAGCCCTGACCAG CGGCGTGCACACCTTCCCCGCCGTGCTGCAGAGCAGCGGC CTGTACAGCCTGAGCAGCTGGTGACCGTGCCCAGCAGCAGC CTGGGCACCCAGACCTACATCTGTAACGTGAACCACAAGCC CAGCAACACCAAGGTGGACAAGAAGGTGGAGCCCAAGAGCT GTGACAAGA CCCACACCTGCCCCCCCTGCCCTGCCCCCGAGCTGGCCGG AGCCCCCAGC GTGTTCCTGTTCCCCCCCAAGCCTAAGGACACCCTGATGATC AGCAGAACCCCCGAGGTGACCTGTGTGGTGGTGGATGTGAG CCACGAGGACCCTGAGGTGAAGTTCAACTGGTACGTGGACG GCGTGGAGGTGCACAATGCCAAGACCAAGCCCAGGGAGGA GCAGTACAACAGCACCTACCGGGTGGTGTCCGTGCTGACCG TGCTGCACCAGGATT GGCTGAACGGCAAGGAGTACAAGTGTAAGGTGTCCAACAAG GCCCTGCCTGCCCCTATCGAGAAAACCATCAGCAAGGCCAA GGGCCAGCCCAGAGAGCCCCAGGTGTAC ACCCTGCCCCCTAGCAGAGATGAGCTGACCAAGAACCAGGT GTCCCTGACCTGCCTGGTGAAGGGCTTCTACCCCAGCGACA TCGCCGTGGAGTGGGAGAGCAACGGCCAGCCCGAGAACAA CTACAAGACCACCCCCCCTGTGCTGGACAGCGATGGCAGCT TCTTCCTGTACAGCAAGCTGACCGTGGACAAGAGCAGATGG CAGCAGGGCAACGTGTTCAGCTGCTCCGTGATGCACGAGGC CCTGCACAATCACTACACCCAGAAGAGCCTGAGCCTGTCCC CTGGCAAG |
| 28 | 13Y039-3E07-2944_LC | GACATCCAGATGACCCAGTCTCCATCCTCCCTGTCTGCATCT GTAGGAGACAGAGTCACCATCACTTGCCAGGCGAGTCAGGA CATTGCCAACTATTTAAATTGGTATCAGCAGAAACCAGGGAA AGCCCCTAAGCTCCTGATCTACGATGCATCCAATTTGGAAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGCCGATACCCTCCCTTTCACTT TTGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |
| 33 | 13Y039-8F02-2949_LCDR1 | RASQGISSWLA |
| 34 | 13Y039-8F02-2949_LCDR2 | AASSLQS |
| 35 | 13Y039-8F02-2949_LCDR3 | QQALSLPYT |
| 36 | 13Y039-8F02-2949_HCDR1 | EWAIS |
| 37 | 13Y039-8F02-2949_HCDR2 | AIIPKFGTAEYAQKFQG |
| 38 | 13Y039-8F02-2949_HCDR3 | GAKYYYAEDYMDV |
| 39 | 13Y039-8F02-2949_VL | DIQMTQSPSSVSASVGDRVTITCRASQGISSWLAWYQQKPGKA PKLLIYAASSLQSGVPSRFSGSGSGTDFTLTISSLQPEDFATYYC QQALSLPYTFGGGTKVEIK |

-continued

SEQUENCE LISTING

| SEQ ID NO. | Description | Sequence |
|---|---|---|
| 40 | 13Y039-8F02-2949_VH | QVQLVQSGAEVKKPGSSVKVSCKASGGTFSEWAISWVRQAPG QGLEWMGAIIPKFGTAEYAQKFQGRVTITADESTSTAYMELSSL RSEDTAVYYCARGAKYYYAEDYMDVWGKGTTVTVSS |
| 41 | 13Y039-8F02-2949-mAb\|light_chain\| | DIQMTQSPSSVSASVGDRVTITCRASQGISSWLAWYQQKPGKA PKLLIYAASSLQSGVPSRFSGSGSGTDFTLTISSLQPEDFATYYC QQALSLPYTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 42 | 13Y039-8F02-2949-mAb\|heavy_chain\| | QVQLVQSGAEVKKPGSSVKVSCKASGGTFSEWAISWVRQAPG QGLEWMGAIIPKFGTAEYAQKFQGRVTITADESTSTAYMELSSL RSEDTAVYYCARGAKYYYAEDYMDVWGKGTTVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELAGAPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK |
| 43 | 13Y039-8F02-2949\|VL\| | GACATCCAGATGACCCAGTCTCCATCTTCCGTGTCTGCATCT GTAGGAGACAGAGTCACCATCACTTGTCGGGCGAGTCAGGG TATTAGCAGCTGGTTAGCCTGGTATCAGCAGAAACCAGGGAA AGCCCCTAAGCTCCTGATCTATGCTGCATCCAGTTTGCAAAG TGGGGTCCCATCAAGGTTCAGCGGCAGTGGATCTGGGACAG ATTTCACTCTCACCATCAGCAGCCTGCAGCCTGAAGATTTTG CAACTTATTACTGTCAGCAGGCACTCAGTCTCCCTTACACTTT TGGCGGAGGGACCAAGGTTGAGATCAAA |
| 44 | 13Y039-8F02-2949\|VH\| | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGAGTGGGCTATCAGCTGGGTGCGACAGGCCCC TGGACAAGGGCTTGAGTGGATGGGAGCTATCATCCCTAAGT TTGGTACAGCAGAGTACGCACAGAAGTTCCAGGGCAGAGTC ACGATTACCGCGGACGAATCCACGAGCACAGCCTACATGGA GCTGAGCAGCCTGAGATCTGAGGACACGGCGGTGTACTACT GCGCCAGAGGTGCTAAGTACTACTACGCTGAGGACTACATG GACGTATGGGGCAAGGGTACAACTGTCACCGTCTCCTCA |
| 45 | 13Y039-8F02-2949_LC | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGAGTGGGCTATCAGCTGGGTGCGACAGGCCCC TGGACAAGGGCTTGAGTGGATGGGAGCTATCATCCCTAAGT TTGGTACAGCAGAGTACGCACAGAAGTTCCAGGGCAGAGTC ACGATTACCGCGGACGAATCCACGAGCACAGCCTACATGGA GCTGAGCAGCCTGAGATCTGAGGACACGGCGGTGTACTACT GCGCCAGAGGTGCTAAGTACTACTACGCTGAGGACTACATG GACGTATGGGGCAAGGGTACAACTGTCACCGTCTCCTCAGC CAGCACCAAGGGCCCCAGCGTGTTCCCCCTGGCCCCCAGC AGCAAGAGCACCAGCGGCGGCACAGCCGCCCTGGGCTGCC TGGTGAAGGACTACTTCCCCGAGCCCGTGACCGTGTCCTGG AACAGCGGAGCCCTGACCAGCGGCGTGCACACCTTCCCCG CCGTGCTGCAGAGCAGCGGCCTGTACAGCCTGAGCAGCGT GGTGACCGTGCCCAGCAGCAGCCTGGGCACCCAGACCTAC ATCTGTAACGTGAACCACAAGCCCAGCAACACCAAGGTGGA CAAGAAGGTGGAGCCCAAGAGCTGTGACAAGACCCACACCT GCCCCCCCTGCCCTGCCCCCGAGCTGGCCGGAGCCCCCAG CGTGTTCCTGTTCCCCCCCAAGCCTAAGGACACCCTGATGAT CAGCAGAACCCCCGAGGTGACCTGTGTGGTGGTGGATGTGA GCCACGAGGACCCTGAGGTGAAGTTCAACTGGTACGTGGAC GGCGTGGAGGTGCACAATGCCAAGACCAAGCCCAGGGAGG AGCAGTACAACAGCACCTACCGGGTGGTGTCCGTGCTGACC GTGCTGCACCAGGATTGGCTGAACGGCAAGGAGTACAAGTG TAAGGTGTCCAACAAGGCCCTGCCTGCCCCTATCGAGAAAA CCATCAGCAAGGCCAAGGGCCAGCCCAGAGAGCCCCAGGT GTACACCCTGCCCCCTAGCAGAGATGAGCTGACCAAGAACC AGGTGTCCCTGACCTGCCTGGTGAAGGGCTTCTACCCCAGC GACATCGCCGTGGAGTGGGAGAGCAACGGCCAGCCCGAGA ACAACTACAAGACCACCCCCCCTGTGCTGGACAGCGATGGC AGCTTCTTCCTGTACAGCAAGCTGACCGTGGACAAGAGCAG |

-continued

SEQUENCE LISTING

| SEQ ID NO. | Description | Sequence |
|---|---|---|
| | | ATGGCAGCAGGGCAACGTGTTCAGCTGCTCCGTGATGCACG AGGCCCTGCACAATCACTACACCCAGAAGAGCCTGAGCCTG TCCCCTGGCAAG |
| 46 | 13Y039-8F02-2949_LC | GACATCCAGATGACCCAGTCTCCATCTTCCGTGTCTGCATCT GTAGGAGACAGAGTCACCATCACTTGTCGGGCGAGTCAGGG TATTAGCAGCTGGTTAGCCTGGTATCAGCAGAAACCAGGGAA AGCCCCTAAGCTCCTGATCTATGCTGCATCCAGTTTGCAAAG TGGGGTCCCATCAAGGTTCAGCGGCAGTGGATCTGGGACAG ATTTCACTCTCACCATCAGCAGCCTGCAGCCTGAAGATTTTG CAACTTATTACTGTCAGCAGGCACTCAGTCTCCCTTACACTTT TGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |
| 47 | 13Y039-4B06-4376_LCDR1 | RASQSVSSYLA |
| 48 | 13Y039-4B06-4376_LCDR2 | DASNRAT |
| 49 | 13Y039-4B06-4376_LCDR3 | QQSDSWPPT |
| 50 | 13Y039-4B06-4376_HCDR1 | GYYMN |
| 51 | 13Y039-4B06-4376_HCDR2 | WINPSSGETNYAQKFQG |
| 52 | 13Y039-4B06-4376_HCDR3 | DTGELDGMNWYFDL |
| 53 | 13Y039-4B06-4376_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 54 | 13Y039-4B06-4376_VH | QVQLVQSGAEVKKPGASVKVSCKASGYTFMGYYMNWVRQAP GQGLEWMGWINPSSGETNYAQKFQGRVTMTRDTSISTAYMEL SRLRSDDTAVYYCARDTGELDGMNWYFDLWGRGTLVTVSS |
| 55 | 13Y039-4B06-4376-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 56 | 13Y039-4B06-4376-mAb\|heavy_chain\| | QVQLVQSGAEVKKPGASVKVSCKASGYTFMGYYMNWVRQAP GQGLEWMGWINPSSGETNYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 57 | 13Y039-4B06-4376\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |

-continued

SEQUENCE LISTING

| SEQ ID NO. | Description | Sequence |
|---|---|---|
| 58 | 13Y039-4B06-4376\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCATGGGCTACTATATGAATTGGGTGCGACAGGCCCCT GGACAAGGGCTTGAGTGGATGGGATGGATCAACCCTTCTAG TGGTGAGACAAACTATGCACAGAAGTTTCAGGGCAGGGTCA CCATGACCAGGGACACGTCCATCAGCACAGCCTACATGGAG CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA |
| 59 | 13Y039-4B06-4376_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCATGGGCTACTATATGAATTGGGTGCGACAGGCCCCT GGACAAGGGCTTGAGTGGATGGGATGGATCAACCCTTCTAG TGGTGAGACAAACTATGCACAGAAGTTTCAGGGCAGGGTCA CCATGACCAGGGACACGTCCATCAGCACAGCCTACATGGAG CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA GCCAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCCT GGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 60 | 13Y039-4B06-4376_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 61 | 13Y039-4B06-4373_LCDR1 | RASQSVSSYLA |
| 62 | 13Y039-4B06-4373_LCDR2 | DASNRAT |
| 63 | 13Y039-4B06-4373_LCDR3 | QQSDSWPPT |

-continued

SEQUENCE LISTING

| SEQ ID NO. | Description | Sequence |
|---|---|---|
| 64 | 13Y039-4B06-4373_HCDR1 | SYYMN |
| 65 | 13Y039-4B06-4373_HCDR2 | IINPSSGETSYAQKFQG |
| 66 | 13Y039-4B06-4373_HCDR3 | DTGELDGMNWYFDL |
| 67 | 13Y039-4B06-4373_VH | QVQLVQSGAEVKKPGASVKVSCKASGYTFRSYYMNWVRQAP GQGLEWMGIINPSSGETSYAQKFQGRVTMTRDTSTSTVYMELS SLRSEDTAVYYCARDTGELDGMNWYFDLWGRGTLVTVSS |
| 68 | 13Y039-4B06-4373_VL | EIVLTQSPATLSLSPGERATLSCRASQSVSSSYLAWYQQKPGQA PRLLIYDASNRATGIPARFSGSGSGTDFTLTISSLEPEDFAVYYC QQSDSWPPTFGGGTKVEIK |
| 69 | 13Y039-4B06-4373-mAb\|light_chain\| | EIVLTQSPATLSLSPGERATLSCRASQSVSSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 70 | 13Y039-4B06-4373-mAb\|heavy_chain\| | QVQLVQSGAEVKKPGASVKVSCKASGYTFRSYYMNWVRQAP GQGLEWMGIINPSSGETSYAQKFQGRVTMTRDTSTSTVYMELS SLRSEDTAVYYCARDTGELDGMNWYFDLWGRGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKKVEPKSCDKTHTCPPCPAPELAGAPSVFLFPPKPKDTL MISRTPEVTCVVVDVSHEDPEVKFNWYVDGVEVHNAKTKPREE QYNSTYRVVSVLTVLHQDWLNGKEYKCKVSNKALPAPIEKTISK AKGQPREPQVYTLPPSRDELTKNQVSLTCLVKGFYPSDIAVEW ESNGQPENNYKTTPPVLDSDGSFFLYSKLTVDKSRWQQGNVF SCSVMHEALHNHYTQKSLSLSPGK |
| 71 | 13Y039-4B06-4373\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 72 | 13Y039-4B06-4373\|VH\| | CAGGTGCAGCTGGTGCAGTCTGGGGCTGAGGTGAAGAAGC CTGGGGCCTCAGTGAAGGTTTCCTGCAAGGCATCTGGATAC ACCTTCAGGAGCTACTATATGAATTGGGTGCGACAGGCCCCT GGACAAGGGCTTGAGTGGATGGGAATAATCAACCCTAGTTC GGGTGAGACAAGCTACGCACAGAAGTTCCAGGGCAGAGTCA CCATGACCAGGGACACGTCCACGAGCACAGTCTACATGGAG CTGAGCAGCCTGAGATCTGAGGACACGGCGGTGTACTACTG CGCCAGAGACACGGGAGAACTTGACGGAATGAACTGGTACT TCGACCTATGGGGGAGAGGTACCTTGGTCACCGTCTCCTCA |
| 73 | 13Y039-4B06-4373_HC | CAGGTGCAGCTGGTGCAGTCTGGGGCTGAGGTGAAGAAGC CTGGGGCCTCAGTGAAGGTTTCCTGCAAGGCATCTGGATAC ACCTTCAGGAGCTACTATATGAATTGGGTGCGACAGGCCCCT GGACAAGGGCTTGAGTGGATGGGAATAATCAACCCTAGTTC GGGTGAGACAAGCTACGCACAGAAGTTCCAGGGCAGAGTCA CCATGACCAGGGACACGTCCACGAGCACAGTCTACATGGAG CTGAGCAGCCTGAGATCTGAGGACACGGCGGTGTACTACTG CGCCAGAGACACGGGAGAACTTGACGGAATGAACTGGTACT TCGACCTATGGGGGAGAGGTACCTTGGTCACCGTCTCCTCA GCCAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCCT GGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC |

-continued

SEQUENCE LISTING

| SEQ ID NO. | Description | Sequence |
|---|---|---|
| | | AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 74 | 13Y039-4B06-4373_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 75 | 13Y039-4B06-4364_LCDR1 | RASQSVSSYLA |
| 76 | 13Y039-4B06-4364_LCDR2 | DASNRAT |
| 77 | 13Y039-4B06-4364_LCDR3 | QQSDSWPPT |
| 78 | 13Y039-4B06-4364_HCDR1 | GYYMS |
| 79 | 13Y039-4B06-4364_HCDR2 | WINPNSGETIYAQKFQG |
| 80 | 13Y039-4B06-4364_HCDR3 | DTGELDGMNWYFDL |
| 81 | 13Y039-4B06-4364_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 82 | 13Y039-4B06-4364_VH | QVQLVQSGAEVKKPGASVKVSCKASGYTFRGYYMSWVRQAP GQGLEWMGWINPNSGETIYAQKFQGRVTMTRDTSISTAYMELS RLRSDDTAVYYCARDTGELDGMNWYFDLWGRGTLVTVSS |
| 83 | 13Y039-4B06-4364-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 84 | 13Y039-4B06-4364-mAb\|heavy_chain\| | QVQLVQSGAEVKKPGASVKVSCKASGYTFRGYYMSWVRQAP GQGLEWMGWINPNSGETIYAQKFQGRVTMTRDTSISTAYMELS RLRSDDTAVYYCARDTGELDGMNWYFDLWGRGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKKVEPKSCDKTHTCPPCPAPELAGAPSVFLFPPKPKDTL MISRTPEVTCVVVDVSHEDPEVKFNWYVDGVEVHNAKTKPREE |

-continued

SEQUENCE LISTING

| SEQ ID NO. | Description | Sequence |
|---|---|---|
| | | QYNSTYRVVSVLTVLHQDWLNGKEYKCKVSNKALPAPIEKTISK AKGQPREPQVYTLPPSRDELTKNQVSLTCLVKGFYPSDIAVEW ESNGQPENNYKTTPPVLDSDGSFFLYSKLTVDKSRWQQGNVF SCSVMHEALHNHYTQKSLSLSPGK |
| 85 | 13Y039-4B06-4364\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 86 | 13Y039-4B06-4364\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCCGGGGCTACTATATGAGTTGGGTGCGACAGGCCCC TGGACAAGGGCTTGAGTGGATGGGATGGATCAACCCTAACA GTGGTGAGACAATTTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC A |
| 87 | 13Y039-4B06-4364_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCCGGGGCTACTATATGAGTTGGGTGCGACAGGCCCC TGGACAAGGGCTTGAGTGGATGGGATGGATCAACCCTAACA GTGGTGAGACAATTTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC AGCCAGCACCAAGGGCCCCAGCGTGTTCCCCCTGGCCCCC AGCAGCAAGAGCACCAGCGGCGGCACAGCCGCCCTGGGCT GCCTGGTGAAGGACTACTTCCCCGAGCCCGTGACCGTGTCC TGGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 88 | 13Y039-4B06-4364_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC |

-continued

SEQUENCE LISTING

| SEQ ID NO. | Description | Sequence |
|---|---|---|
| | | TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 89 | 13Y039-4B06-4351_LCDR1 | RASQSVSSYLA |
| 90 | 13Y039-4B06-4351_LCDR2 | DASNRAT |
| 91 | 13Y039-4B06-4351_LCDR3 | QQSDSWPPT |
| 92 | 13Y039-4B06-4351_HCDR1 | GYYMS |
| 93 | 13Y039-4B06-4351_HCDR2 | WINPNSGETFYAQKFQG |
| 94 | 13Y039-4B06-4351_HCDR3 | DTGELDGMNWYFDL |
| 95 | 13Y039-4B06-4351_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 96 | 13Y039-4B06-4351_VH | QVQLVQSGAEVKKPGASVKVSCKASGYTFSGYYMSWVRQAP GQGLEWMGWINPNSGETFYAQKFQGRVTMTRDTSISTAYMEL SRLRSDDTAVYYCARDTGELDGMNWYFDLWGRGTLVTVSS |
| 97 | 13Y039-4B06-4351-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 98 | 13Y039-4B06-4351-mAb\|heavy_chain\| | QVQLVQSGAEVKKPGASVKVSCKASGYTFSGYYMSWVRQAP GQGLEWMGWINPNSGETFYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 99 | 13Y039-4B06-4351\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 100 | 13Y039-4B06-4351\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCTCGGGCTACTATATGAGTTGGGTGCGACAGGCCCC TGGACAAGGGCTTGAGTGGATGGGATGGATCAACCCTAACA GTGGTGAGACATTTTATGCACAGAAGTTTCAGGGCAGGGTCA CCATGACCAGGGACACGTCCATCAGCACAGCCTACATGGAG CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA |
| 101 | 13Y039-4B06-4351_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCTCGGGCTACTATATGAGTTGGGTGCGACAGGCCCC TGGACAAGGGCTTGAGTGGATGGGATGGATCAACCCTAACA GTGGTGAGACATTTTATGCACAGAAGTTTCAGGGCAGGGTCA CCATGACCAGGGACACGTCCATCAGCACAGCCTACATGGAG |

-continued

SEQUENCE LISTING

| SEQ ID NO. | Description | Sequence |
|---|---|---|
| | | CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA GCCAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCCT GGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 102 | 13Y039-4B06-4351_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 103 | 13Y039-4B06-4348_LCDR1 | RASQSVSSYLA |
| 104 | 13Y039-4B06-4348_LCDR2 | DASNRAT |
| 105 | 13Y039-4B06-4348_LCDR3 | QQSDSWPPT |
| 106 | 13Y039-4B06-4348_HCDR1 | GYYMS |
| 107 | 13Y039-4B06-4348_HCDR2 | WINPNSGETYYAQKFQG |
| 108 | 13Y039-4B06-4348_HCDR3 | DTGELDGMNWYFDL |
| 109 | 13Y039-4B06-4348_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 110 | 13Y039-4B06-4348_VH | QVQLVQSGAEVKKPGASVKVSCKASGYTFGGYYMSWVRQAP GQGLEWMGWINPNSGETYYAQKFQGRVTMTRDTSISTAYMEL SRLRSDDTAVYYCARDTGELDGMNWYFDLWGRGTLVTVSS |

-continued

SEQUENCE LISTING

| SEQ ID NO. | Description | Sequence |
|---|---|---|
| 111 | 13Y039-4B06-4348-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 112 | 13Y039-4B06-4348-mAb\|heavy_chain\| | QVQLVQSGAEVKKPGASVKVSCKASGYTFGGYYMSWVRQAP GQGLEWMGWINPNSGETYYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 113 | 13Y039-4B06-4348\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 114 | 13Y039-4B06-4348\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCGGGGGCTACTATATGTCGTGGGTGCGACAGGCCCC TGGACAAGGGCTTGAGTGGATGGGATGGATCAACCCTAACA GTGGTGAGACATATTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC A |
| 115 | 13Y039-4B06-4348_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCGGGGGCTACTATATGTCGTGGGTGCGACAGGCCCC TGGACAAGGGCTTGAGTGGATGGGATGGATCAACCCTAACA GTGGTGAGACATATTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC AGCCAGCACCAAGGGCCCCAGCGTGTTCCCCCTGGCCCCC AGCAGCAAGAGCACCAGCGGCGGCACAGCCGCCCTGGGCT GCCTGGTGAAGGACTACTTCCCCGAGCCCGTGACCGTGTCC TGGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCT GCCCCTATCGAGAAAACCATCAGCAAGGCCAAGGGCCAGCC CAGAGAGCCCCAGGTGTACACCCTGCCCCCTAGCAGAGATG AGCTGACCAAGAACCAGGTGTCCCTGACCTGCCTGGTGAAG GGCTTCTACCCCAGCGACATCGCCGTGGAGTGGGAGAGCAA CGGCCAGCCCGAGAACAACTACAAGACCACCCCCCCTGTGC TGGACAGCGATGGCAGCTTCTTCCTGTACAGCAAGCTGACC GTGGACAAGAGCAGATGGCAGCAGGGCAACGTGTTCAGCTG CTCCGTGATGCACGAGGCCCTGCACAATCACTACACCCAGA AGAGCCTGAGCCTGTCCCCTGGCAAG |

-continued

SEQUENCE LISTING

| SEQ ID NO. | Description | Sequence |
|---|---|---|
| 116 | 13Y039-4B06-4348_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 117 | 13Y039-4B06-4328_LCDR1 | RASQSVSSYLA |
| 118 | 13Y039-4B06-4328_LCDR2 | DASNRAT |
| 119 | 13Y039-4B06-4328_LCDR3 | QQSDSWPPT |
| 120 | 13Y039-4B06-4328_HCDR1 | GYYMN |
| 121 | 13Y039-4B06-4328_HCDR2 | WINPLSGETNYAQKFQG |
| 122 | 13Y039-4B06-4328_HCDR3 | DTGELDGMNWYFDL |
| 123 | 13Y039-4B06-4328_VL\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 124 | 13Y039-4B06-4328_VH | QVQLVQSGAEVKKPGASVKVSCKASGYTFHGYYMNWVRQAP GQGLEWMGWINPLSGETNYAQKFQGRVTMTRDTSISTAYMEL SRLRSDDTAVYYCARDTGELDGMNWYFDLWGRGTLVTVSS |
| 125 | 13Y039-4B06-4328-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 126 | 13Y039-4B06-4328-mAb\|heavy_chain\| | QVQLVQSGAEVKKPGASVKVSCKASGYTFHGYYMNWVRQAP GQGLEWMGWINPLSGETNYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 127 | 13Y039-4B06-4328\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 128 | 13Y039-4B06-4328\|VH\| | CAGGTGCAGCTGGTGCAGTCTGGGGCTGAGGTGAAGAAGC CTGGGGCCTCAGTGAAGGTCTCCTGCAAGGCTTCTGGATAC |

-continued

SEQUENCE LISTING

| SEQ ID NO. | Description | Sequence |
|---|---|---|
| | | ACCTTCCATGGCTACTATATGAATTGGGTGCGACAGGCCCCT<br>GGACAAGGGCTTGAGTGGATGGGATGGATCAACCCTCTGAG<br>TGGTGAGACAAACTATGCACAGAAGTTTCAGGGCAGGGTCA<br>CCATGACCAGGGACACGTCCATCAGCACAGCCTACATGGAG<br>CTGAGCAGGCTGAGATCTGACGACACGGCGGTGTACTACTG<br>CGCCAGAGACACGGGAGAACTTGACGGAATGAACTGGTACT<br>TCGACCTATGGGGGAGAGGTACCTTGGTCACCGTCTCCTCA |
| 129 | 13Y039-4B06-4328_HC | CAGGTGCAGCTGGTGCAGTCTGGGGCTGAGGTGAAGAAGC<br>CTGGGGCCTCAGTGAAGGTCTCCTGCAAGGCTTCTGGATAC<br>ACCTTCCATGGCTACTATATGAATTGGGTGCGACAGGCCCCT<br>GGACAAGGGCTTGAGTGGATGGGATGGATCAACCCTCTGAG<br>TGGTGAGACAAACTATGCACAGAAGTTTCAGGGCAGGGTCA<br>CCATGACCAGGGACACGTCCATCAGCACAGCCTACATGGAG<br>CTGAGCAGGCTGAGATCTGACGACACGGCGGTGTACTACTG<br>CGCCAGAGACACGGGAGAACTTGACGGAATGAACTGGTACT<br>TCGACCTATGGGGGAGAGGTACCTTGGTCACCGTCTCCTCA<br>GCCAGCACCAAGGGCCCCAGCGTGTTCCCCCTGGCCCCCA<br>GCAGCAAGAGCACCAGCGGCGGCACAGCCGCCCTGGGCTG<br>CCTGGTGAAGGACTACTTCCCCGAGCCCGTGACCGTGTCCT<br>GGAACAGCGGAGCCCTGACCAGCGGCGTGCACACCTTCCC<br>CGCCGTGCTGCAGAGCAGCGGCCTGTACAGCCTGAGCAGC<br>GTGGTGACCGTGCCCAGCAGCAGCCTGGGCACCCAGACCT<br>ACATCTGTAACGTGAACCACAAGCCCAGCAACACCAAGGTG<br>GACAAGAAGGTGGAGCCCAAGAGCTGTGACAAGACCCACAC<br>CTGCCCCCCCTGCCCTGCCCCCGAGCTGGCCGGAGCCCCC<br>AGCGTGTTCCTGTTCCCCCCCAAGCCTAAGGACACCCTGAT<br>GATCAGCAGAACCCCCGAGGTGACCTGTGTGGTGGTGGATG<br>TGAGCCACGAGGACCCTGAGGTGAAGTTCAACTGGTACGTG<br>GACGGCGTGGAGGTGCACAATGCCAAGACCAAGCCCAGGG<br>AGGAGCAGTACAACAGCACCTACCGGGTGGTGTCCGTGCTG<br>ACCGTGCTGCACCAGGATTGGCTGAACGGCAAGGAGTACAA<br>GTGTAAGGTGTCCAACAAGGCCCTGCCTGCCCCTATCGAGA<br>AAACCATCAGCAAGGCCAAGGGCCAGCCCAGAGAGCCCCA<br>GGTGTACACCCTGCCCCCTAGCAGAGATGAGCTGACCAAGA<br>ACCAGGTGTCCCTGACCTGCCTGGTGAAGGGCTTCTACCCC<br>AGCGACATCGCCGTGGAGTGGGAGAGCAACGGCCAGCCCG<br>AGAACAACTACAAGACCACCCCCCCTGTGCTGGACAGCGAT<br>GGCAGCTTCTTCCTGTACAGCAAGCTGACCGTGGACAAGAG<br>CAGATGGCAGCAGGGCAACGTGTTCAGCTGCTCCGTGATGC<br>ACGAGGCCCTGCACAATCACTACACCCAGAAGAGCCTGAGC<br>CTGTCCCCTGGCAAG |
| 130 | 13Y039-4B06-4328_LC | GAAATTGTGTTGACACAGTCTCCAGCCACCCTGTCTTTGTCT<br>CCAGGGGAAAGAGCCACCCTCTCCTGCAGGGCCAGTCAGA<br>GTGTTAGCAGCTACTTAGCCTGGTACCAACAGAAACCTGGCC<br>AGGCTCCCAGGCTCCTCATCTATGATGCATCCAACAGGGCC<br>ACTGGCATCCCAGCCAGGTTCAGTGGCAGTGGGTCTGGGAC<br>AGACTTCACTCTCACCATCAGCAGCCTAGAGCCTGAAGATTT<br>TGCAGTTTATTACTGTCAGCAGTCCGACTCCTGGCCTCCTAC<br>TTTTGGCGGAGGGACCAAGGTTGAGATCAAACGTACGGTGG<br>CCGCCCCCAGCGTGTTCATCTTCCCCCCCAGCGATGAGCAG<br>CTGAAGAGCGGCACCGCCAGCGTGGTGTGTCTGCTGAACAA<br>CTTCTACCCCCGGGAGGCCAAGGTGCAGTGGAAGGTGGACA<br>ATGCCCTGCAGAGCGGCAACAGCCAGGAGAGCGTGACCGA<br>GCAGGACAGCAAGGACTCCACCTACAGCCTGAGCAGCACCC<br>TGACCCTGAGCAAGGCCGACTACGAGAAGCACAAGGTGTAC<br>GCCTGTGAGGTGACCCACCAGGGCCTGTCCAGCCCCGTGA<br>CCAAGAGCTTCAACCGGGGCGAGTGC |
| 131 | 13Y039-4B06-4327_LCDR1 | RASQSVSSYLA |
| 132 | 13Y039-4B06-4327_LCDR2 | DASNRAT |
| 133 | 13Y039-4B06-4327_LCDR3 | QQSDSWPPT |
| 134 | 13Y039-4B06-4327_HCDR1 | GYYMT |

-continued

SEQUENCE LISTING

| SEQ ID NO. | Description | Sequence |
|---|---|---|
| 135 | 13Y039-4B06-4327_HCDR2 | NINPNSGWTNYAQKFQG |
| 136 | 13Y039-4B06-4327_HCDR3 | DTGELDGMNWYFDL |
| 137 | 13Y039-4B06-4327_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 138 | 13Y039-4B06-4327_VH | QVQLVQSGAEVKKPGASVKVSCKASGYTFPGYYMTWVRQAPG QGLEWMGNINPNSGWTNYAQKFQGRVTMTRDTSISTAYMELS RLRSDDTAVYYCARDTGELDGMNWYFDLWGRGTLVTVSS |
| 139 | 13Y039-4B06-4327-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 140 | 13Y039-4B06-4327-mAb\|heavy_chain\| | QVQLVQSGAEVKKPGASVKVSCKASGYTFPGYYMTWVRQAPG QGLEWMGNINPNSGWTNYAQKFQGRVTMTRDTSISTAYMELS RLRSDDTAVYYCARDTGELDGMNWYFDLWGRGTLVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKKVEPKSCDKTHTCPPCPAPELAGAPSVFLFPPKPKDTL MISRTPEVTCVVVDVSHEDPEVKFNWYVDGVEVHNAKTKPREE QYNSTYRVVSVLTVLHQDWLNGKEYKCKVSNKALPAPIEKTISK AKGQPREPQVYTLPPSRDELTKNQVSLTCLVKGFYPSDIAVEW ESNGQPENNYKTTPPVLDSDGSFFLYSKLTVDKSRWQQGNVF SCSVMHEALHNHYTQKSLSLSPGK |
| 141 | 13Y039-4B06-4327\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 142 | 13Y039-4B06-4327\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCCCTGGCTACTATATGACTTGGGTGCGACAGGCCCCT GGACAAGGGCTTGAGTGGATGGGAAATATCAACCCTAACAG TGGTTGGACAAACTATGCACAGAAGTTTCAGGGCAGGGTCA CCATGACCAGGGACACGTCCATCAGCACAGCCTACATGGAG CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA |
| 143 | 13Y039-4B06-4327_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCCCTGGCTACTATATGACTTGGGTGCGACAGGCCCCT GGACAAGGGCTTGAGTGGATGGGAAATATCAACCCTAACAG TGGTTGGACAAACTATGCACAGAAGTTTCAGGGCAGGGTCA CCATGACCAGGGACACGTCCATCAGCACAGCCTACATGGAG CTGAGCAGGCTGAGATCTGACGACACGGCGGTGTACTACTG CGCCAGAGACACGGGAGAACTTGACGGAATGAACTGGTACT TCGACCTATGGGGGAGAGGTACCTTGGTCACCGTCTCCTCA GCCAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCCT GGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG |

-continued

SEQUENCE LISTING

| SEQ ID NO. | Description | Sequence |
|---|---|---|
| | | GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 144 | 13Y039-4B06-4327_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 145 | 13Y039-4B06-4325_LCDR1 | RASQSVSSYLA |
| 146 | 13Y039-4B06-4325_LCDR2 | DASNRAT |
| 147 | 13Y039-4B06-4325_LCDR3 | QQSDSWPPT |
| 148 | 13Y039-4B06-4325_HCDR1 | GYYMS |
| 149 | 13Y039-4B06-4325_HCDR2 | WINPQSGETNYAQKFQG |
| 150 | 13Y039-4B06-4325_HCDR3 | DTGELDGMNWYFDL |
| 151 | 13Y039-4B06-4325_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 152 | 13Y039-4B06-4325_VH | QVQLVQSGAEVKKPGASVKVSCKASGYTFWGYYMSWVRQAP GQGLEWMGWINPQSGETNYAQKFQGRVTMTRDTSISTAYMEL SRLRSDDTAVYYCARDTGELDGMNWYFDLWGRGTLVTVSS |
| 153 | 13Y039-4B06-4325-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 154 | 13Y039-4B06-4325-mAb\|heavy_chain\| | QVQLVQSGAEVKKPGASVKVSCKASGYTFWGYYMSWVRQAP GQGLEWMGWINPQSGETNYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI |

-continued

SEQUENCE LISTING

| SEQ ID NO. | Description | Sequence |
|---|---|---|
| | | SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 155 | 13Y039-4B06-4325\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 156 | 13Y039-4B06-4325\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCTGGGGCTACTATATGAGTTGGGTGCGACAGGCCCC TGGACAAGGGCTTGAGTGGATGGGATGGATCAACCCTCAGA GTGGTGAGACAAACTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC A |
| 157 | 13Y039-4B06-4325+HC | CAGGTGCAGCTGGTGCAGTCTGGGGCTGAGGTGAAGAAGC CTGGGGCCTCAGTGAAGGTCTCCTGCAAGGCTTCTGGATAC ACCTTCTGGGGCTACTATATGAGTTGGGTGCGACAGGCCCC TGGACAAGGGCTTGAGTGGATGGGATGGATCAACCCTCAGA GTGGTGAGACAAACTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC AGCCAGCACCAAGGGCCCCAGCGTGTTCCCCCTGGCCCCC AGCAGCAAGAGCACCAGCGGCGGCACAGCCGCCCTGGGCT GCCTGGTGAAGGACTACTTCCCCGAGCCCGTGACCGTGTCC TGGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 158 | 13Y039-4B06-4325_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC |

-continued

SEQUENCE LISTING

| SEQ ID NO. | Description | Sequence |
|---|---|---|
| | | GCCTGTGAGGTGACCCACCAGGGCCTGTCCAGCCCCGTGA CCAAGAGCTTCAACCGGGGCGAGTGC |
| 159 | 13Y039-4B06-4324_LCDR1 | RASQSVSSYLA |
| 160 | 13Y039-4B06-4324_LCDR2 | DASNRAT |
| 161 | 13Y039-4B06-4324_LCDR3 | QQSDSWPPT |
| 162 | 13Y039-4B06-4324_HCDR1 | GYYMS |
| 163 | 13Y039-4B06-4324_HCDR2 | WINPMSGETNYAQKFQG |
| 164 | 13Y039-4B06-4324_HCDR3 | DTGELDGMNWYFDL |
| 165 | 13Y039-4B06-4324_VL | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIK |
| 166 | 13Y039-4B06-4324_VH | QVQLVQSGAEVKKPGASVKVSCKASGYTFRGYYMSWVRQAP GQGLEWMGWINPMSGETNYAQKFQGRVTMTRDTSISTAYMEL SRLRSDDTAVYYCARDTGELDGMNWYFDLWGRGTLVTVSS |
| 167 | 13Y039-4B06-4324-mAb\|light_chain\| | EIVLTQSPATLSLSPGERATLSCRASQSVSSYLAWYQQKPGQA PRLLIYDASNRATGIPARFSGSGSGTDFTLTISSLEPEDFAVYYC QQSDSWPPTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |
| 168 | 13Y039-4B06-4324-mAb\|heavy_chain\| | QVQLVQSGAEVKKPGASVKVSCKASGYTFRGYYMSWVRQAP GQGLEWMGWINPMSGETNYAQKFQGRVTMTRDTSISTAYMEL SRLRSDDTAVYYCARDTGELDGMNWYFDLWGRGTLVTVSSAS TKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCDKTHTCPPCPAPELAGAPSVFLFPPKPKD TLMISRTPEVTCVVVDVSHEDPEVKFNWYVDGVEVHNAKTKPR EEQYNSTYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNV FSCSVMHEALHNHYTQKSLSLSPGK |
| 169 | 13Y039-4B06-4324\|VL\| | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAA |
| 170 | 13Y039-4B06-4324\|VH\| | CAGGTGCAGCTGGTGCAGTCTGGGGCTGAGGTGAAGAAGC CTGGGGCCTCAGTGAAGGTCTCCTGCAAGGCTTCTGGATAC ACCTTCCGTGGCTACTATATGAGTTGGGTGCGACAGGCCCC TGGACAAGGGCTTGAGTGGATGGGATGGATCAACCCTATGA GTGGTGAGACAAACTATGCACAGAAGTTTCAGGGCAGGGTC ACCATGACCAGGGACACGTCCATCAGCACAGCCTACATGGA GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC A |
| 171 | 13Y039-4B06-4324_HC | CAGGTGCAGCTGGTGCAGTCTGGGGCTGAGGTGAAGAAGC CTGGGGCCTCAGTGAAGGTCTCCTGCAAGGCTTCTGGATAC ACCTTCCGTGGCTACTATATGAGTTGGGTGCGACAGGCCCC TGGACAAGGGCTTGAGTGGATGGGATGGATCAACCCTATGA GTGGTGAGACAAACTATGCACAGAAGTTTCAGGGCAGGGTC ACCATGACCAGGGACACGTCCATCAGCACAGCCTACATGGA |

-continued

| SEQUENCE LISTING | | |
|---|---|---|
| SEQ ID NO. | Description | Sequence |
| | | GCTGAGCAGGCTGAGATCTGACGACACGGCGGTGTACTACT GCGCCAGAGACACGGGAGAACTTGACGGAATGAACTGGTAC TTCGACCTATGGGGGAGAGGTACCTTGGTCACCGTCTCCTC AGCCAGCACCAAGGGCCCCAGCGTGTTCCCCCTGGCCCCC AGCAGCAAGAGCACCAGCGGCGGCACAGCCGCCCTGGGCT GCCTGGTGAAGGACTACTTCCCCGAGCCCGTGACCGTGTCC TGGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 172 | 13Y039-4B06-4324_LC | GAAATTGTGTTGACACAGTCTCCAGCCACCCTGTCTTTGTCT CCAGGGGAAAGAGCCACCCTCTCCTGCAGGGCCAGTCAGA GTGTTAGCAGCTACTTAGCCTGGTACCAACAGAAACCTGGCC AGGCTCCCAGGCTCCTCATCTATGATGCATCCAACAGGGCC ACTGGCATCCCAGCCAGGTTCAGTGGCAGTGGGTCTGGGAC AGACTTCACTCTCACCATCAGCAGCCTAGAGCCTGAAGATTT TGCAGTTTATTACTGTCAGCAGTCCGACTCCTGGCCTCCTAC TTTTGGCGGAGGGACCAAGGTTGAGATCAAACGTACGGTGG CCGCCCCCAGCGTGTTCATCTTCCCCCCCAGCGATGAGCAG CTGAAGAGCGGCACCGCCAGCGTGGTGTGTCTGCTGAACAA CTTCTACCCCCGGGAGGCCAAGGTGCAGTGGAAGGTGGACA ATGCCCTGCAGAGCGGCAACAGCCAGGAGAGCGTGACCGA GCAGGACAGCAAGGACTCCACCTACAGCCTGAGCAGCACCC TGACCCTGAGCAAGGCCGACTACGAGAAGCACAAGGTGTAC GCCTGTGAGGTGACCCACCAGGGCCTGTCCAGCCCCGTGA CCAAGAGCTTCAACCGGGGCGAGTGC |
| 173 | 13Y039-127G03-2890_LCDR1 | QASQDISNYLN |
| 174 | 13Y039-127G03-2890_LCDR2 | DASNLET |
| 175 | 13Y039-127G03-2890_LCDR3 | QQADIFPLT |
| 176 | 13Y039-127G03-2890_HCDR1 | SYAIS |
| 177 | 13Y039-127G03-2890_HCDR2 | GIIPVFGSAYYAQKFQG |
| 178 | 13Y039-127G03-2890_HCDR3 | EGRAYYGSESYDDSDYMDV |
| 179 | 13Y039-127G03-2890_VL | DIQMTQSPSSLSASVGDRVTITCQASQDISNYLNWYQQKPGKA PKLLIYDASNLETGVPSRFSGSGSGTDFTFTISSLQPEDIATYYC QQADIFPLTFGGGTKVEIK |

-continued

SEQUENCE LISTING

| SEQ ID NO. | Description | Sequence |
|---|---|---|
| 180 | 13Y039-127G03-2890_VH | QVQLVQSGAEVKKPGSSVKVSCKASGGTFSSYAISWVRQAPG QGLEWMGGIIPVFGSAYYAQKFQGRVTITADESTSTAYMELSSL RSEDTAVYYCAGEGRAYYGSESYDDSDYMDVWGKGTTVTVSS |
| 181 | 13Y039-127G03-2890-mAb\|light_chain\| | DIQMTQSPSSLSASVGDRVTITCQASQDISNYLNWYQQKPGKA PKLLIYDASNLETGVPSRFSGSGSGTDFTFTISSLQPEDIATYYC QQADIFPLTFGGGTKVEIKRTVAAPSVFIFPP SDEQLKSGTASVVCLLNNFYPREAKVQWKVDNALQSGNSQES VTEQDSKDSTYSLSSTLTLSKADYEKHKVYACEVTHQGLSSPVT KSFNRGEC |
| 182 | 13Y039-127G03-2890-mAb\|heavy_chain\| | QVQLVQSGAEVKKPGSSVKVSCKASGGTFSSYAISWVRQAPG QGLEWMGGIIPVFGSAYYAQKFQGRVTITADESTSTAYMELSSL RSEDTAVYYCAGEGRAYYGSESYDDSDYMDVWGKGTTVTVSS ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKKVEPKSCDKTHTCPPCPAPELAGAPSVFLFPPKP KDTLMISRTPEVTCVVVDVSHEDPEVKFNWYVDGVEVHNAKTK PREEQYNSTYRVVSVLTVLHQDWLNGKEYKCKVSNKALPAPIE KTISKAKGQPREPQVYTLPPSRDELTKNQVSLTCLVKGFYPSDI AVEWESNGQPENNYKTTPPVLDSDGSFFLYSKLTVDKSRWQQ GNVFSCSVMHEALHNHYTQKSLSLSPGK |
| 183 | 13Y039-127G03-2890\|VL\| | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGAAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGCCGATATCTTCCCTCTCACTTT TGGCGGAGGGACCAAGGTTGAGATCAAA |
| 184 | 13Y039-127G03-2890\|VH\| | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCTCGTACGCGATCTCGTGGGTGCGACAGGCCCC TGGACAAGGGCTTGAGTGGATGGGAGGGATCATCCCCGTCT TTGGCTCGGCGTACTACGCGCAGAAGTTCCAGGGCAGAGTC ACGATTACCGCGGACGAATCCACGAGCACAGCCTACATGGA GCTGAGCAGCCTGAGATCTGAGGACACGGCGGTGTACTACT GCGCCGGAGAAGGCCGGGCGTATTATGGGTCGGAGTCGTA CGATGACTCTGACTATATGGACGTCTGGGGCAAGGGTACAA CTGTCACCGTCTCCTCA |
| 185 | 13Y039-127G03-2890_HC | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCTCGTACGCGATCTCGTGGGTGCGACAGGCCCC TGGACAAGGGCTTGAGTGGATGGGAGGGATCATCCCCGTCT TTGGCTCGGCGTACTACGCGCAGAAGTTCCAGGGCAGAGTC ACGATTACCGCGGACGAATCCACGAGCACAGCCTACATGGA GCTGAGCAGCCTGAGATCTGAGGACACGGCGGTGTACTACT GCGCCGGAGAAGGCCGGGCGTATTATGGGTCGGAGTCGTA CGATGACTCTGACTATATGGACGTCTGGGGCAAGGGTACAA CTGTCACCGTCTCCTCAGCCAGCACCAAGGGCCCCAGCGTG TTCCCCCTGGCCCCCAGCAGCAAGAGCACCAGCGGCGGCA CAGCCGCCCTGGGCTGCCTGGTGAAGGACTACTTCCCCGAG CCCGTGACCGTGTCCTGGAACAGCGGAGCCCTGACCAGCG GCGTGCACACCTTCCCCGCCGTGCTGCAGAGCAGCGGCCT GTACAGCCTGAGCAGCGTGGTGACCGTGCCCAGCAGCAGC CTGGGCACCCAGACCTACATCTGTAACGTGAACCACAAGCC CAGCAACACCAAGGTGGACAAGAAGGTGGAGCCCAAGAGCT GTGACAAGACCCACACCTGCCCCCCCTGCCCTGCCCCCGAG CTGGCCGGAGCCCCCAGCGTGTTCCTGTTCCCCCCCAAGCC TAAGGACACCCTGATGATCAGCAGAACCCCCGAGGTGACCT GTGTGGTGGTGGATGTGAGCCACGAGGACCCTGAGGTGAA GTTCAACTGGTACGTGGACGGCGTGGAGGTGCACAATGCCA AGACCAAGCCCAGGGAGGAGCAGTACAACAGCACCTACCGG GTGGTGTCCGTGCTGACCGTGCTGCACCAGGATTGGCTGAA CGGCAAGGAGTACAAGTGTAAGGTGTCCAACAAGGCCCTGC CTGCCCCTATCGAGAAAACCATCAGCAAGGCCAAGGGCCAG CCCAGAGAGCCCCAGGTGTACACCCTGCCCCCTAGCAGAGA TGAGCTGACCAAGAACCAGGTGTCCCTGACCTGCCTGGTGA AGGGCTTCTACCCCAGCGACATCGCCGTGGAGTGGGAGAG |

-continued

SEQUENCE LISTING

| SEQ ID NO. | Description | Sequence |
|---|---|---|
| | | CAACGGCCAGCCCGAGAACAACTACAAGACCACCCCCCCTG TGCTGGACAGCGATGGCAGCTTCTTCCTGTACAGCAAGCTG ACCGTGGACAAGAGCAGATGGCAGCAGGGCAACGTGTTCAG CTGCTCCGTGATGCACGAGGCCCTGCACAATCACTACACCC AGAAGAGCCTGAGCCTGTCCCCTGGCAAG |
| 186 | 13Y039-127G03-2890_LC | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGAAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGCCGATATCTTCCCTCTCACTTT TGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |
| 187 | 13Y039-152B02-2948_LCDR1 | QASQDISNYLN |
| 188 | 13Y039-152B02-2948_LCDR2 | DASNLAT |
| 189 | 13Y039-152B02-2948_LCDR3 | QQDDYLPIT |
| 190 | 13Y039-152B02-2948_HCDR1 | DFAIS |
| 191 | 13Y039-152B02-2948_HCDR2 | GIIPIYGTASYAQKFLG |
| 192 | 13Y039-152B02-2948_HCDR3 | DVGVQLVYHGAFDI |
| 193 | 13Y039-152B02-2948_VL | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIK |
| 194 | 13Y039-152B02-2948_VH\| | QVQLVQSGAEVKKPGSSVKVSCKASGGTFSDFAISWVRQAPG QGLEWMGGIIPIYGTASYAQKFLGRVTITADESTSTAYMELSSLR SEDTAVYYCARDVGVQLVYHGAFDIWGQGTMVTVSS |
| 195 | 13Y039-152B02-2948-mAb\|light_chain\| | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIKRTVAAPSVFIFPP SDEQLKSGTASVVCLLNNFYPREAKVQWKVDNALQSGNSQES VTEQDSKDSTYSLSSTLTLSKADYEKHKVYACEVTHQGLSSPVT KSFNRGEC |
| 196 | 13Y039-152B02-2948-mAb\|heavy_chain\| | QVQLVQSGAEVKKPGSSVKVSCKASGGTFSDFAISWVRQAPG QGLEWMGGIIPIYGTASYAQKFLGRVTITADESTSTAYMELSSLR SEDTAVYYCARDVGVQLVYHGAFDIWGQGTMVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELAGAPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSRDELTKNQVSLTCLVKGFYPSDIAVEWES NGQPENNYKTTPPVLDSDGSFFLYSKLTVDKSRWQQGNVFSC SVMHEALHNHYTQKSLSLSPGK |

-continued

SEQUENCE LISTING

| SEQ ID NO. | Description | Sequence |
|---|---|---|
| 197 | 13Y039-152B02-2948\|VL\| | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAA |
| 198 | 13Y039-152B02-2948\|VH\| | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGACTTTGCCATCTCGTGGGTGCGACAGGCCCC TGGACAAGGGCTTGAGTGGATGGGAGGGATCATTCCCATCT ATGGCACGGCGAGCTACGCGCAGAAGTTCCTAGGCAGAGTC ACGATTACCGCGGACGAATCCACGAGCACAGCCTACATGGA GCTGAGCAGCCTGAGATCTGAGGACACGGCGGTGTACTACT GCGCCAGAGATGTGGGCGTCCAACTCGTCTATCACGGGGCG TTCGACATCTGGGGTCAGGGTACAATGGTCACCGTCTCCTCA |
| 199 | 13Y039-152B02-2948_HC | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGACTTTGCCATCTCGTGGGTGCGACAGGCCCC TGGACAAGGGCTTGAGTGGATGGGAGGGATCATTCCCATCT ATGGCACGGCGAGCTACGCGCAGAAGTTCCTAGGCAGAGTC ACGATTACCGCGGACGAATCCACGAGCACAGCCTACATGGA GCTGAGCAGCCTGAGATCTGAGGACACGGCGGTGTACTACT GCGCCAGAGATGTGGGCGTCCAACTCGTCTATCACGGGGCG TTCGACATCTGGGGTCAGGGTACAATGGTCACCGTCTCCTCA GCCAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCCT GGAACAGCGGAGCCCTGACCAGCGGCGTGCACACCTTCCC CGCCGTGCTGCAGAGCAGCGGCCTGTACAGCCTGAGCAGC GTGGTGACCGTGCCCAGCAGCAGCCTGGGCACCCAGACCT ACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 200 | 13Y039-152B02-2948_LC | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |

-continued

SEQUENCE LISTING

| SEQ ID NO. | Description | Sequence |
|---|---|---|
| 201 | 13Y039-152B02-2940_LCDR1 | QASQDISNYLN |
| 202 | 13Y039-152B02-2940_LCDR2 | DASNLAT |
| 203 | 13Y039-152B02-2940_LCDR3 | QQDDYLPIT |
| 204 | 13Y039-152B02-2940_HCDR1 | SDAIS |
| 205 | 13Y039-152B02-2940_HCDR2 | GIITNFGTATYAQKFQG |
| 206 | 13Y039-152B02-2940_HCDR3 | DVGVQLVYHGAFDI |
| 207 | 13Y039-152B02-2940_VH | QVQLVQSGAEVKKPGSSVKVSCKASGGTFSSDAISWVRQAPG QGLEWMGGIITNFGTATYAQKFQGRVTITADESTSTAYMELSSL RSEDTAVYYCARDVGVQLVYHGAFDIWGQGTMVTVSS |
| 208 | 13Y039-152B02-2940_VL | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIK |
| 209 | 13Y039-152B02-2940-mAb\|light_chain\| | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIKRTVAAPSVFIFPP SDEQLKSGTASVVCLLNNFYPREAKVQWKVDNALQSGNSQES VTEQDSKDSTYSLSSTLTLSKADYEKHKVYACEVTHQGLSSPVT KSFNRGEC |
| 210 | 13Y039-152B02-2940-mAb\|heavy_chain\| | QVQLVQSGAEVKKPGSSVKVSCKASGGTFSSDAISWVRQAPG QGLEWMGGIITNFGTATYAQKFQGRVTITADESTSTAYMELSSL RSEDTAVYYCARDVGVQLVYHGAFDIWGQGTMVTVSSASTKG PSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELAGAPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISKA KGQPREPQVYTLPPSRDELTKNQVSLTCLVKGFYPSDIAVEWE SNGQPENNYKTTPPVLDSDGSFFLYSKLTVDKSRWQQGNVFS CSVMHEALHNHYTQKSLSLSPGK |
| 211 | 13Y039-152B02-2940\|VL\| | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAA |
| 212 | 13Y039-152B02-2940\|VH\| | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCTCCGACGCGATCTCGTGGGTGCGACAGGCCCC TGGACAAGGGCTTGAGTGGATGGGAGGGATCATCACCAACT TTGGGACCGCCACCTACGCGCAGAAGTTCCAGGGGAGAGTC ACGATTACCGCGGACGAATCCACGAGCACAGCCTACATGGA GCTGAGCAGCCTGAGATCTGAGGACACGGCGGTGTACTACT GCGCCAGAGATGTCGGGGTGCAACTGGTCTATCACGGGGC GTTCGACATCTGGGGTCAGGGTACAATGGTCACCGTCTCCT CA |

-continued

SEQUENCE LISTING

| SEQ ID NO. | Description | Sequence |
|---|---|---|
| 213 | 13Y039-152B02-2940_HC | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCTCCGACGCGATCTCGTGGGTGCGACAGGCCCC TGGACAAGGGCTTGAGTGGATGGGAGGGATCATCACCAACT TTGGGACCGCCACCTACGCGCAGAAGTTCCAGGGGAGAGTC ACGATTACCGCGGACGAATCCACGAGCACAGCCTACATGGA GCTGAGCAGCCTGAGATCTGAGGACACGGCGGTGTACTACT GCGCCAGAGATGTCGGGGTGCAACTGGTCTATCACGGGGC GTTCGACATCTGGGGTCAGGGTACAATGGTCACCGTCTCCT CAGCCAGCACCAAGGGCCCCAGCGTGTTCCCCCTGGCCCC CAGCAGCAAGAGCACCAGCGGCGGCACAGCCGCCCTGGGC TGCCTGGTGAAGGACTACTTCCCCGAGCCCGTGACCGTGTC CTGGAACAGCGGAGCCCTGACCAGCGGCGTGCACACCTTCC CCGCCGTGCTGCAGAGCAGCGGCCTGTACAGCCTGAGCAG CGTGGTGACCGTGCCCAGCAGCAGCCTGGGCACCCAGACC TACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 214 | 13Y039-152B02-2940_LC | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |
| 215 | 13Y039-152B02-2935_LCDR1 | QASQDISNYLN |
| 216 | 13Y039-152B02-2935_LCDR2 | DASNLAT |
| 217 | 13Y039-152B02-2935_LCDR3 | QQDDYLPIT |
| 218 | 13Y039-152B02-2935_HCDR1 | ESAIS |
| 219 | 13Y039-152B02-2935_HCDR2 | GIIPTFDTTNYAQKFQG |

-continued

SEQUENCE LISTING

| SEQ ID NO. | Description | Sequence |
|---|---|---|
| 220 | 13Y039-152B02-2935_HCDR3 | DVGVQLVYHGAFDI |
| 221 | 13Y039-152B02-2935_VL | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIK |
| 222 | 13Y039-152B02-2935_VH | QVQLVQSGAEVKKPGSSVKVSCKASGGTFSESAISWVRQAPG QGLEWMGGIIPTFDTTNYAQKFQGRVTITADESTSTAYMELSSL RSEDTAVYYCARDVGVQLVYHGAFDIWGQGTMVTVSS |
| 223 | 13Y039-152B02-2935-mAb\|light_chain\| | DIQMTQSPSSLSASVGDRVTITCQASQDISNYLNWYQQKPGKA PKLLIYDASNLATGVPSRFSGSGSGTDFTFTISSLQPEDIATYYC QQDDYLPITFGGGTKVEIKRTVAAPSVFIFPP SDEQLKSGTASVVCLLNNFYPREAKVQWKVDNALQSGNSQES VTEQDSKDSTYSLSSTLTLSKADYEKHKVYACEVTHQGLSSPVT KSFNRGEC |
| 224 | 13Y039-152B02-2935-mAb\|heavy_chain\| | QVQLVQSGAEVKKPGSSVKVSCKASGGTFSESAISWVRQAPG QGLEWMGGIIPTFDTTNYAQKFQGRVTITADESTSTAYMELSSL RSEDTAVYYCARDVGVQLVYHGAFDIWGQGTMVTVSSASTKG PSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELAGAPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISKA KGQPREPQVYTLPPSRDELTKNQVSLTCLVKGFYPSDIAVEWE SNGQPENNYKTTPPVLDSDGSFFLYSKLTVDKSRWQQGNVFS CSVMHEALHNHYTQKSLSLSPGK |
| 225 | 13Y039-152B02-2935\|VL\| | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAA |
| 226 | 13Y039-152B02-2935\|VH\| | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGAGTCCGCGATTTCGTGGGTGCGACAGGCCCC TGGACAAGGGCTTGAGTGGATGGGAGGGATCATCCCGACCT TTGACACCACCAACTACGCGCAGAAGTTCCAGGGGAGAGTC ACGATTACCGCGGACGAATCCACGAGCACAGCCTACATGGA GCTGAGCAGCCTGAGATCTGAGGACACGGCGGTGTACTACT GCGCCAGAGATGTCGGGGTGCAACTGGTCTACCACGGCGC GTTCGACATCTGGGGTCAGGGTACAATGGTCACCGTCTCCT CA |
| 227 | 13Y039-152B02-2935_HC | CAGGTGCAGCTGGTGCAGTCTGGGGCTGAGGTGAAGAAGC CTGGGTCCTCGGTGAAGGTCTCCTGCAAGGCTTCTGGAGGC ACCTTCAGCGAGTCCGCGATTTCGTGGGTGCGACAGGCCCC TGGACAAGGGCTTGAGTGGATGGGAGGGATCATCCCGACCT TTGACACCACCAACTACGCGCAGAAGTTCCAGGGGAGAGTC ACGATTACCGCGGACGAATCCACGAGCACAGCCTACATGGA GCTGAGCAGCCTGAGATCTGAGGACACGGCGGTGTACTACT GCGCCAGAGATGTCGGGGTGCAACTGGTCTACCACGGCGC GTTCGACATCTGGGGTCAGGGTACAATGGTCACCGTCTCCT CAGCCAGCACCAAGGGCCCCAGCGTGTTCCCCCTGGCCCC CAGCAGCAAGAGCACCAGCGGCGGCACAGCCGCCCTGGGC TGCCTGGTGAAGGACTACTTCCCCGAGCCCGTGACCGTGTC CTGGAACAGCGGAGCCCTGACCAGCGGCGTGCACACCTTCC CCGCCGTGCTGCAGAGCAGCGGCCTGTACAGCCTGAGCAG CGTGGTGACCGTGCCCAGCAGCAGCCTGGGCACCCAGACC TACATCTGTAACGTGAACCACAAGCCCAGCAACACCAAGGTG GACAAGAAGGTGGAGCCCAAGAGCTGTGACAAGACCCACAC CTGCCCCCCCTGCCCTGCCCCCGAGCTGGCCGGAGCCCCC AGCGTGTTCCTGTTCCCCCCCAAGCCTAAGGACACCCTGAT GATCAGCAGAACCCCCGAGGTGACCTGTGTGGTGGTGGATG TGAGCCACGAGGACCCTGAGGTGAAGTTCAACTGGTACGTG GACGGCGTGGAGGTGCACAATGCCAAGACCAAGCCCAGGG |

-continued

| SEQUENCE LISTING | | |
|---|---|---|
| SEQ ID NO. | Description | Sequence |
| | | AGGAGCAGTACAACAGCACCTACCGGGTGGTGTCCGTGCTG ACCGTGCTGCACCAGGATTGGCTGAACGGCAAGGAGTACAA GTGTAAGGTGTCCAACAAGGCCCTGCCTGCCCCTATCGAGA AAACCATCAGCAAGGCCAAGGGCCAGCCCAGAGAGCCCCA GGTGTACACCCTGCCCCCTAGCAGAGATGAGCTGACCAAGA ACCAGGTGTCCCTGACCTGCCTGGTGAAGGGCTTCTACCCC AGCGACATCGCCGTGGAGTGGGAGAGCAACGGCCAGCCCG AGAACAACTACAAGACCACCCCCCCTGTGCTGGACAGCGAT GGCAGCTTCTTCCTGTACAGCAAGCTGACCGTGGACAAGAG CAGATGGCAGCAGGGCAACGTGTTCAGCTGCTCCGTGATGC ACGAGGCCCTGCACAATCACTACACCCAGAAGAGCCTGAGC CTGTCCCCTGGCAAG |
| 228 | 13Y039-152B02-2935_LC | GACATCCAGATGACCCAGTCTCCATCCTCCCTGTCTGCATCT GTAGGAGACAGAGTCACCATCACTTGCCAGGCGAGTCAGGA CATTAGCAACTATTTAAATTGGTATCAGCAGAAACCAGGGAA AGCCCCTAAGCTCCTGATCTACGATGCATCCAATTTGGCAAC AGGGGTCCCATCAAGGTTCAGTGGAAGTGGATCTGGGACAG ATTTTACTTTCACCATCAGCAGCCTGCAGCCTGAAGATATTG CAACATATTACTGTCAGCAGGACGATTACCTCCCTATCACTTT TGGCGGAGGGACCAAGGTTGAGATCAAACGTACGGTGGCC GCCCCCAGCGTGTTCATCTTCCCCCCCAGCGATGAGCAGCT GAAGAGCGGCACCGCCAGCGTGGTGTGTCTGCTGAACAACT TCTACCCCCGGGAGGCCAAGGTGCAGTGGAAGGTGGACAAT GCCCTGCAGAGCGGCAACAGCCAGGAGAGCGTGACCGAGC AGGACAGCAAGGACTCCACCTACAGCCTGAGCAGCACCCTG ACCCTGAGCAAGGCCGACTACGAGAAGCACAAGGTGTACGC CTGTGAGGTGACCCACCAGGGCCTGTCCAGCCCCGTGACCA AGAGCTTCAACCGGGGCGAGTGC |

TABLE 16

| SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION | | |
|---|---|---|
| SEQ ID NO. | Description | Sequence |
| 229 | 13Y039 4B06-4344 mouse kappa_LC | GAGATCGTGCTGACCCAGAGCCCTGCAACC CTGTCCCTGAGCCCTGGCGAAAGGGCCACT CTGAGCTGCAGGGCCAGCCAGAGCGTGAG CAGCTACCTCGCCTGGTACCAGCAGAAGCC CGGCCAGGCCCCTAGGCTGCTGATCTACGA CGCCAGCAACAGGGCCACCGGCATTCCCG CAAGGTTCAGCGGCAGCGGCAGCGGCACC GACTTCACCCTGACCATCAGCAGCCTGGAG CCCGAAGACTTCGCAGTCTACTACTGCCAG CAGAGCGACAGCTGGCCCCCCACCTTCGG GGGCGGCACCAAGGTGGAGATCAAGAGGG CTGACGCGGCGCCCACCGTGAGCATCTTCC CCCCCAGCAGCGAGCAGCTGACTAGCGGC GGAGCCTCTGTGGTGTGCTTCCTGAACAAC TTCTACCCCAAGGACATCAACGTGAAGTGG AAGATCGACGGCAGCGAGAGGCAGAACGG AGTCCTCAACAGCTGGACCGACCAGGACAG CAAGGATAGCACCTACAGCATGAGCAGCAC CCTGACCCTGACCAAGGACGAGTACGAGAG GCACAACAGCTACACCTGCGAAGCCACCCA CAAAACCTCCACCAGCCCCATCGTGAAGAG CTTCAATAGGAACGAGTGC |
| 230 | 13Y039 4B06-4344 mouse kappa_LC | EIVLTQSPATLSLSPGERATLSCRASQSVSSYL AWYQQKPGQAPRLLIYDASNRATGIPARFSGS GSGTDFTLTISSLEPEDFAVYYCQQSDSWPPT FGGGTKVEIKRADAAPTVSIFPPSSEQLTSGG ASVVCFLNNFYPKDINVKWKIDGSERQNGVLN SWTDQDSKDSTYSMSSTLTLTKDEYERHNSY TCEATHKTSTSPIVKSFNRNEC |

TABLE 16-continued

SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION

| SEQ ID NO. | Description | Sequence |
|---|---|---|
| 231 | 13Y039 4B06-4344 mouse IgG2a LAGA_HC | CAGGTGCAGCTCGTGCAGAGCGGCGCCGA GGTGAAAAAGCCCGGCGCCTCTGTCAAGGT GAGCTGCAAGGCCAGCGGCTACACCTTCCT GGGCTACTACATGAGCTGGGTGAGGCAGGC TCCCGGACAGGGCCTGGAGTGGATGGGCT GGATCAACCCCCTGAGCGGCGAGACCAACT ACGCCCAGAAGTTCCAGGGCAGGGTGACCA TGACCAGGGACACCAGCATCAGCACCGCCT ACATGGAACTGAGCAGGCTGAGGAGCGACG ACACCGCCGTGTATTACTGCGCCAGGGACA CCGGCGAGCTGGACGGCATGAACTGGTACT TCGACCTGTGGGGCAGGGGCACCCTGGTG ACAGTGAGCAGCGCTAAAACCACCGCCCCC TCCGTGTACCCCCTGGCGCCCGTCTGTGGC GACACCACCGGCAGCAGCGTGACACTGGG CTGCCTGGTGAAGGGCTACTTCCCCGAGCC CGTCACCCTGACCTGGAATAGCGGAAGCCT GTCAAGCGGCGTGCACACTTTCCCCGCCGT GCTGCAGTCTGACCTGTACACCCTGAGCAG CAGCGTGACCGTGACCAGCAGCACCTGGCC CAGCCAGTCTATCACTTGCAACGTGGCCCA CCCTGCCAGCTCCACCAAGGTGGACAAGAA GATCGAGCCTAGGGGACCCACCATTAAACC CTGCCCCCCCTGCAAGTGCCCCGCCCCCAA TCTGGCCGGAGCCCCCAGCGTGTTTATCTT CCCCCCCAAGATCAAGGACGTGCTGATGAT CAGCCTGAGCCCCATCGTGACCTGCGTGGT GGTGGACGTGAGCGAGGACGACCCAGACG TGCAGATCAGCTGGTTTGTGAACAACGTGG AGGTGCACACCGCCCAGACCCAGACCCACA GGGAGGATTACAACAGCACCCTGAGGGTGG TGAGCGCCCTGCCCATCCAGCACCAGGACT GGATGTCCGGCAAGGAGTTCAAGTGCAAGG TGAACAACAAGGACCTGCCCGCCCCCATCG AGAGGACCATCAGCAAGCCTAAGGGCAGCG TGAGGGCACCCCAGGTCTACGTGCTGCCCC CCCCAGAGGAGGAAATGACCAAGAAGCAGG TGACCCTGACCTGCATGGTGACCGACTTCA TGCCCGAGGACATCTACGTGGAGTGGACCA ACAACGGCAAGACCGAGCTGAACTACAAGA ACACCGAGCCCGTGCTGGAGAGCGACGGC AGCTACTTCATGTATAGCAAGCTGCGGGTC GAGAAGAAGAACTGGGTGGAGAGGAACAGC TACAGCTGCAGCGTCGTGCACGAAGGCCTC CACAACCACCACACCACCAAGAGCTTCAGC AGGACCCCCGGGAAG |
| 232 | 13Y039 4B06-4344 mouse IgG2a LAGA_HC | QVQLVQSGAEVKKPGASVKVSCKASGYTFLG YYMSWVRQAPGQGLEWMGWINPLSGETNYA QKFQGRVTMTRDTSISTAYMELSRLRSDDTAV YYCARDTGELDGMNWYFDLWGRGTLVTVSS AKTTAPSVYPLAPVCGDTTGSSVTLGQLVKGY FPEPVTLTWNSGSLSSGVHTFPAVLQSDLYTL SSSVTVTSSTWPSQSITCNVAHPASSTKVDKK IEPRGPTIKPCPPCKCPAPNLAGAPSVFIFPPKI KDVLMISLSPIVTCVVVDVSEDDPDVQISWFVN NVEVHTAQTQTHREDYNSTLRVVSALPIQHQD WMSGKEFKCKVNNKDLPAPIERTISKPKGSVR APQVYVLPPPEEEMTKKQVTLTCMVTDEMPE DIYVEWTNNGKTELNYKNTEPVLDSDGSYFM YSKLRVEKKNWVERNSYSCSVVHEGLHNHHT TKSFSRTPGK |
| 233 | 13Y0394B06-4344 rat IgG2b LAGA_HC | QVQLVQSGAEVKKPGASVKVSCKASGYTFLG YYMSWVRQAPGQGLEWMGWINPLSGETNYA QKFQGRVTMTRDTSISTAYMELSRLRSDDTAV YYCARDTGELDGMNWYFDLWGRGTLVTVSS AQTTAPSVYPLAPGCGDTTSSTVTLGCLVKGY FPEPVTVTWNSGALSSDVHTFPAVLQSGLYTL TSSVTSSTWPSQTVTQNVAHPASSTKVDKKV ERRNGGIGHKCPTCPTCHKCPVPELAGAPSV FIFPPKPKDILLISQNAKVTCVVVDVSEEEPDV |

TABLE 16-continued

SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION

| SEQ ID NO. | Description | Sequence |
|---|---|---|
| | | QFSWFVNNVEVHTAQTQPREEQYNSTFRVVS<br>ALPIQHQDWMSGKEFKCKVNNKALPSPIEKTI<br>SKPKGLVRKPQVYVMGPPTEQLTEQTVSLTCL<br>TSGFLPNDIGVEWTSNGHIEKNYKNTEPVMDS<br>DGSFFMYSKLNVERSRWDSRAPFVCSVVHEG<br>LHNHHVEKSISRPPGK |
| 234 | 13Y0394B06-4344 rat IgG2b LAGA_LC | EIVLTQSPATLSLSPGERATLSCRASQSVSSYL<br>AWYQQKPGQAPRLLIYDASNRATGIPARFSGS<br>GSGTDFTLTISSLEPEDFAVYYCQQSDSWPPT<br>FGGGTKVEIKRADAAPTVSIFPPSTEQLATGG<br>ASVVCLMNNFYPRDISVKWKIDGTERRDGVLD<br>SVTDQDSKDSTYSMSSTLSLTKADYESHNLYT<br>CEVVHKTSSSPVVKSFNRNEC |
| 235 | 13Y0394B06-4344 rat IgG2b LAGA_LC | GAGATCGTGCTGACCCAGAGCCCTGCAACC<br>CTGTCCCTGAGCCCTGGCGAAAGGGCCACT<br>CTGAGCTGCAGGGCCAGCCAGAGCGTGAG<br>CAGCTACCTCGCCTGGTACCAGCAGAAGCC<br>CGGCCAGGCCCCTAGGCTGCTGATCTACGA<br>CGCCAGCAACAGGGCCACCGGCATTCCCG<br>CAAGGTTCAGCGGCAGCGGCAGCGGCACC<br>GACTTCACCCTGACCATCAGCAGCCTGGAG<br>CCCGAAGACTTCGCAGTCTACTACTGCCAG<br>CAGAGCGAGAGCTGGCCCCCCACCTTCGG<br>GGGCGGCACCAAGGTGGAGATCAAGAGGG<br>CCGACGCGGCGCCCACCGTGTCCATCTTCC<br>CCCCCAGCACCGAACAGCTGGCCACTGGC<br>GGAGCTAGCGTGGTGTGCCTGATGAACAAC<br>TTCTACCCCAGGGACATCAGCGTGAAGTGG<br>AAGATCGACGGCACCGAGAGGAGGGACGG<br>CGTCCTGGATTCTGTGACCGACCAGGACAG<br>CAAAGACAGCACCTACAGCATGAGCAGCAC<br>CCTGAGCCTGACCAAGGCCGACTACGAGAG<br>CCACAACCTCTACACCTGCGAGGTGGTGCA<br>CAAGACCAGCAGCAGCCCCGTGGTGAAGAG<br>CTTCAACAGGAACGAGTGC |
| 236 | 13Y0394B06-4344 rat IgG2b LAGA_HC | CAGGTGCAGCTCGTGCAGAGCGGCGCCGA<br>GGTGAAAAAGCCCGGCGCCTCTGTCAAGGT<br>GAGCTGCAAGGCCAGCGGCTACACCTTCCT<br>GGGCTACTACATGAGCTGGGTGAGGCAGGC<br>TCCCGGACAGGGCCTGGAGTGGATGGGCT<br>GGATCAACCCCCTGAGCGGCGAGACCAACT<br>ACGCCCAGAAGTTCCAGGGCAGGGTGACCA<br>TGACCAGGGAGACCAGCATCAGCACCGCCT<br>ACATGGAACTGAGCAGGCTGAGGAGCGACG<br>ACACCGCCGTGTATTACTGCGCCAGGGACA<br>CCGGCGAGCTGGACGGCATGAACTGGTACT<br>TCGACCTGTGGGGCAGGGGCACCCTGGTG<br>ACAGTGAGCAGCGCCCAGACCACAGCTCCC<br>AGCGTGTATCCCCTGGCGCCCGGCTGTGGC<br>GATACTACCAGCAGCACCGTCACCCTGGGC<br>TGCCTGGTGAAAGGCTACTTCCCCGAACCA<br>GTGACCGTGACCTGGAATAGCGGAGCTCTG<br>TCAAGCGACGTGCACACCTTTCCCGCCGTG<br>CTCCAGAGCGGCCTGTACACCCTCACCAGC<br>AGCGTGACTAGCAGCACCTGGCCCTCTCAG<br>ACCGTGACCTGCAACGTGGCCCACCCCGCC<br>TCTTCCACCAAGGTGGACAAGAAAGTGGAG<br>AGGAGGAACGGCGGAATCGGCCACAAGTG<br>CCCAACCTGCCCCACCTGCCATAAATGCCC<br>CGTGCCCGAACTGGCCGGAGCCCCCAGCG<br>TGTTCATCTTCCCCCCCAAGCCCAAGGACAT<br>CCTGCTGATCAGCCAGAACGCCAAGGTGAC<br>CTGCGTGGTGGTGGACGTCAGCGAGGAGG<br>AGCCCGACGTGCAGTTCAGCTGGTTTGTGA<br>ACAACGTGGAGGTGCACACCGCCCAGACCC<br>AGCCCAGGGAGGAGCAGTACAACAGCACCT<br>TCCGGGTGGTGAGCGCCCTGCCTATCCAGC<br>ACCAGGACTGGATGAGCGGCAAGGAGTTCA<br>AGTGCAAGGTGAACAACAAGGCCCTGCCCA<br>GCCCCATCGAGAAGACCATTAGCAAGCCCA |

TABLE 16-continued

SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION

| SEQ ID NO. | Description | Sequence |
|---|---|---|
| | | AGGGCCTCGTGAGGAAGCCCCAGGTCTACG TGATGGGACCACCTACCGAGCAGCTGACCG AACAGACCGTGTCCCTGACCTGCCTGACCA GCGGCTTCCTGCCCAACGACATCGGCGTGG AGTGGACCAGGAAGGGCCACATCGAGAAGA ACTACAAGAACACCGAGCCCGTGATGGACA GCGACGGCAGCTTCTTCATGTACAGCAAGC TGAACGTGGAGAGGAGCAGGTGGGACAGC AGAGCCCCCTTCGTGTGCAGCGTCGTCCAC GAGGGGCTGCACAACCACCACGTCGAGAAG AGCATCTCTAGGCCCCCCGGCAAG |
| 237 | 13Y039-3E07-2994 rat IgG2b LAGA_LC | DIQMTQSPSSLSASVGDRVTITCQASQDIANYL NWYQQKPGKAPKLLIYDASNLETGVPSRFSG SGSGTDFTFTISSLQPEDIATYYCQQADTLPFT FGGGTKVEIKRADAAPTVSIFPPSTEQLATGG ASVVCLMNNFYPRDISVKWKIDGTERRDGVLD SVTDQDSKDSTYSMSSTLSLTKADYESHNLYT CEVVHKTSSSPVVKSFNRNEC |
| 238 | 13Y039-3E07-2994 rat IgG2b LAGA_HC | QVQLQQWGAGLLKPSETLSLTCAVYGGSFFG DYWSWIRQPPGKGLEWIGEIDWSGATNYNPS LKSRVTISVDTSKNQFSLKLSSVTAADTAVYYC ARGGSKELSFDIWGQGTMVTVSSAQTTAPSV YPLAPGCGDTTSSTVTLGCLVKGYFPEPVTVT WNSGALSSDVHTFPAVLQSGLYTLTSSVTSST WPSQTVTCNVAHPASSTKVDKKVERRNGGIG HKCPTCPTCHKCPVPELAGAPSVFIFPPKPKDI LLISQNAKVTCVVVDVSEEEPDVQFSWFVNNV EVHTAQTQPREEQYNSTFRVVSALPIQHQDW MSGKEFKCKVNNKALPSPIEKTISKPKGLVRKP QVYVMGPPTEQLTEQTVSLTCLTSGFLPNDIG VEWTSNGHIEKNYKNTEPVMDSDGSFFMYSK LNVERSRWDSRAPFVCSVVHEGLHNHHVEKS ISRPPGK |
| 239 | 13Y039-3E07-2994 rat IgG2b LAGA_HC | CAGGTGCAGCTGCAGCAGTGGGGCGCCGG ACTGCTGAAGCCCAGCGAGACCCTGAGCCT GACCTGCGCCGTGTACGGCGGGTCCTTCTT CGGCGACTACTGGAGCTGGATCAGGCAGCC CCCCGGCAAAGGCCTGGAGTGGATCGGCG AGATCGACTGGAGCGGCGCCACCAACTACA ACCCCAGCCTCAAGAGCAGGGTGACCATCA GCGTGGACACCAGCAAGAACCAGTTCAGCC TGAAGCTGAGCAGGGTGACCGCCGCCGACA CCGCCGTGTACTATTGCGCCAGGGGGGGGA GCAAGGAGCTGAGCTTCGACATCTGGGGCC AGGGCACTATGGTCACCGTGAGCAGCGCCC AGACCACAGCTCCCAGCGTGTATCCCCTGG CGCCCGGCTGTGGCGATACTACCAGCAGCA CCGTCACCCTGGGCTGCCTGGTGAAAGGCT ACTTCCCCGAACCAGTGACCGTGACCTGGA ATAGCGGAGCTCTGTCAAGCGACGTGCACA CCTTTCCCGCCGTGCTCCAGAGCGGCCTGT ACACCCTCACCAGCAGCGTGACTAGCAGCA CCTGGCCCTCTCAGACCGTGACCTGCAACG TGGCCCACCCCGCCTCTTCCACCAAGGTGG ACAAGAAAGTGGAGAGGAGGAACGGCGGA ATCGGCCACAAGTGCCCAACCTGCCCCACC TGCCATAAATGCCCCGTGCCCGAACTGGCC GGAGCCCCCAGCGTGTTCATCTTCCCCCCC AAGCCCAAGGACATCCTGCTGATCAGCCAG AACGCCAAGGTGACCTGCGTGGTGGTGGAC GTCAGCGAGGAGGAGCCCGACGTGCAGTT CAGCTGGTTTGTGAACAACGTGGAGGTGCA CACCGCCCAGACCCAGCCCAGGGAGGAGC AGTACAACAGCACCTTCCGGGTGGTGAGCG CCCTGCCTATCCAGCACCAGGACTGGATGA GCGGCAAGGAGTTCAAGTGCAAGGTGAACA ACAAGGCCCTGCCCAGCCCCATCGAGAAGA CCATTAGCAAGCCCAAGGGCCTCGTGAGGA AGCCCCAGGTCTACGTGATGGGACCACCTA CCGAGCAGCTGACCGAACAGACCGTGTCCC |

TABLE 16-continued

SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION

| SEQ ID NO. | Description | Sequence |
|---|---|---|
| | | TGACCTGCCTGACCAGCGGCTTCCTGCCCA<br>ACGACATCGGCGTGGAGTGGACCAGCAACG<br>GCCACATCGAGAAGAACTACAAGAACACCG<br>AGCCCGTGATGGACAGCGACGGCAGCTTCT<br>TCATGTACAGCAAGCTGAACGTGGAGAGGA<br>GCAGGTGGGAGAGCAGAGCCCCCTTCGTGT<br>GCAGCGTCGTCCACGAGGGGCTGCACAAC<br>CACCACGTCGAGAAGAGCATCTCTAGGCCC<br>CCCGGCAAG |
| 240 | 13Y039-3E07-2994 rat IgG2b LAGA_LC | GACATCCAGATGACTCAGTCCCCCTCTAGC<br>CTGAGCGCTAGCGTGGGCGACAGGGTGAC<br>C<br>ATCACCTGCCAGGCCAGCCAGGACATCGCC<br>AACTACCTGAACTGGTACCAGCAGAAGCCC<br>GGCAAGGCCCCCAAACTGCTGATCTACGAC<br>GCCTCAAACCTCGAGACCGGCGTGCCTAGC<br>AGGTTTAGCGGCAGCGGCAGCGGCACCGA<br>CTTCACCTTCACCATCAGCAGCCTGCAGCC<br>C<br>GAGGATATCGCCACCTACTACTGCCAGCAG<br>GCCGACACCCTGCCCTTCACCTTCGGCGGA<br>GGCACCAAGGTGGAGATTAAGAGGGCCGAC<br>GCGGCGCCCACCGTGTCCATCTTCCCCCCC<br>AGCACCGAACAGCTGGCCACTGGCGGAGCT<br>AGCGTGGTGTGCCTGATGAACAACTTCTAC<br>CCCAGGGACATCAGCGTGAAGTGGAAGATC<br>GACGGCACCGAGAGGAGGGACGGCGTCCT<br>G<br>GATTCTGTGACCGACCAGGACAGCAAAGAC<br>AGCACCTACAGCATGAGCAGCACCCTGAGC<br>CTGACCAAGGCCGACTACGAGAGCCACAAC<br>CTCTACACCTGCGAGGTGGTGCACAAGACC<br>AGCAGCAGCCCCGTGGTGAAGAGCTTCAAC<br>AGGAACGAGTGC |
| 29 | 13Y039-3E07-2944 mouse cK LC | DIQMTQSPSSLSASVGDRVTITCQASQDIANYL<br>NWYQQKPGKAPKLLIYDASNLETGVPSRFSG<br>SGSGTDFTFTISSLQPEDIATYYCQQADTLPFT<br>FGGGTKVEIKRADAAPTVSIFPPSSEQLTSGG<br>ASVVCFLNNFYPKDINVKWKIDGSERQNGVLN<br>SWTDQDSKDSTYSMSSTLTLTKDEYERHNSY<br>TCEATHKTSTSPIVKSFNRNEC |
| 30 | 13Y039-3E07-2944 mouse ck LC | GACATCCAGATGACTCAGTCCCCCTCTAGC<br>CTGAGCGCTAGCGTGGGCGACAGGGTGAC<br>CATCACCTGCCAGGCCAGCCAGGACATCGC<br>CAACTACCTGAACTGGTACCAGCAGAAGCC<br>CGGCAAGGCCCCCAAACTGCTGATCTACGA<br>CGCCTCAAACCTCGAGACCGGCGTGCCTAG<br>CAGGTTTAGCGGCAGCGGCAGCGGCACCG<br>ACTTCACCTTCACCATCAGCAGCCTGCAGC<br>CCGAGGATATCGCCACCTACTACTGCCAGC<br>AGGCCGACACCCTGCCCTTCACCTTCGGCG<br>GAGGCACCAAGGTGGAGATTAAGAGGGCTG<br>ACGCGGCGCCCACCGTGAGCATCTTCCCCC<br>CCAGCAGCGAGCAGCTGACTAGCGGCGGA<br>GCCTCTGTGGTGTGCTTCCTGAACAACTTCT<br>ACCCCAAGGACATCAACGTGAAGTGGAAGA<br>TCGACGGCAGCGAGAGGCAGAACGGAGTC<br>CTCAACAGCTGGACCGACCAGGACAGGAAG<br>GATAGCACCTACAGCATGAGCAGCACCCTG<br>ACCCTGACCAAGGACGAGTACGAGAGGGAC<br>AACAGCTACACCTGCGAAGCCACCCACAAA<br>ACCTCCACCAGCCCCATCGTGAAGAGCTTC<br>AATAGGAACGAGTGC |
| 31 | 13Y039-3E07-2944 mouse IgG2a LAGA_HC | QVQLQQWGAGLLKPSETLSLTCAVYGGSFFG<br>DYWSWIRQPPGKGLEWIGEIDWSGATNYNPS<br>LKSRVTISVDTSKNQFSLKLSSVTAADTAVYYC<br>ARGGSKELSFDIWGQGTMVTVSSAKTTAPSV<br>YPLAPVCGDTTGSSVTLGCLVKGYFPEPVTLT<br>WNSGSLSSGVHTFPAVLQSDLYTLSSSVTVTS |

TABLE 16-continued

| SEQ ID NO. | Description | Sequence |
|---|---|---|
| SEQUENCES OF REVERSE CHIMERIC SEQUENCES LC AND HC HUMAN VARIABLE REGION WITH EITHER MOUSE (IGG2A LAGA CK) OR RAT (IGG2B LAGA CK) CONSTANT REGION | | |
| | | STWPSQSITCNVAHPASSTKVDKKIEPRGPTIK PCPPCKCPAPNLAGAPSVFIFPPKIKDVLMISL SPIVTCVVVDVSEDDPDVQISWFVNNVEVHTA QTQTHREDYNSTLRVVSALPIQHQDWMSGKE FKCKVNNKDLPAPIERTISKPKGSVRAPQVYVL PPPEEEMTKKQVTLTCMVTDFMPEDIYVEWT NNGKTELNYKNTEPVLDSDGSYFMYSKLRVE KKNWVERNSYSCSVVHEGLHNHHTTKSFSRT PGK |
| 32 | 13Y039-3E07-2944 mouse IgG2a LAGA_HC | CAGGTGCAGCTGCAGCAGTGGGGCGCCGG ACTGCTGAAGCCCAGCGAGACCCTGAGCCT GACCTGCGCCGTGTACGGGGGGTCCTTCTT CGGCGACTACTGGAGCTGGATCAGGCAGCC CCCCGGCAAAGGCCTGGAGTGGATCGGCG AGATCGACTGGAGCGGCGCCACCAACTACA ACCCCAGCCTCAAGAGCAGGGTGACCATCA GCGTGGACACCAGCAAGAACCAGTTCAGCC TGAAGCTGAGCAGCGTGACCGCCGCCGACA CCGCCGTGTACTATTGCGCCAGGGGCGGCA GCAAGGAGCTGAGCTTCGACATCTGGGGCC AGGGCACTATGGTCACCGTGAGCAGCGCTA AAACCACCGCCCCCTCCGTGTACCCCCTGG CGCCCGTCTGTGGCGACACCACCGGCAGC AGCGTGACACTGGGCTGCCTGGTGAAGGG CTACTTCCCCGAGCCCGTCACCCTGACCTG GAATAGCGGAAGCCTGTCAAGCGGCGTGCA CACTTTCCCCGCCGTGCTGCAGTCTGACCT GTACACCCTGAGCAGCAGCGTGACCGTGAC CAGCAGCACCTGGCCCAGCCAGTCTATCAC TTGCAACGTGGCCCACCCTGCCAGCTCCAC CAAGGTGGACAAGAAGATCGAGCCTAGGGG ACCCACCATTAAACCCTGCCCCCCCTGCAA GTGCCCCGCCCCCAATCTGGCCGGAGCCC CCAGCGTGTTTATCTTCCCCCCCAAGATCAA GGACGTGCTGATGATCAGCCTGAGCCCCAT CGTGACCTGCGTGGTGGTGGACGTGAGCG AGGACGACCCAGACGTGCAGATCAGCTGGT TTGTGAACAACGTGGAGGTGCACACCGCCC AGACCCAGACCCACAGGGAGGATTACAACA GCACCCTGAGGGTGGTGAGCGCCCTGCCC ATCCAGCACCAGGACTGGATGTCCGGCAAG GAGTTCAAGTGCAAGGTGACAACAAGGAC CTGCCCGCCCCCATCGAGAGGACCATCAGC AAGCCTAAGGGCAGCGTGAGGGCACCCCA GGTCTACGTGCTGCCCCCCCCAGAGGAGGA AATGACCAAGAAGCAGGTGACCCTGACCTG CATGGTGACCGACTTCATGCCCGAGGACAT CTACGTGGAGTGGACCAACAACGGGAAGAC CGAGCTGAACTACAAGAACACCGAGCCCGT GCTGGACAGCGACGGCAGCTACTTCATGTA TAGCAAGCTGCGGGTCGAGAAGAAGAACTG GGTGGAGAGGAACAGCTACAGCTGCAGCGT CGTGCACGAAGGCCTCCACAACCACCACAC CACCAAGAGCTTCAGCAGGACCCCCGGGAA G |

The invention claimed is:

1. A BMP1, TLL1 and/or TLL2 antibody comprising the following 6 CDRs:

```
LCDR1 of
                                 (SEQ ID NO: 1)
RASQSVSSYLA;

LCDR2 of
                                 (SEQ ID NO: 2)
DASNRAT;

LCDR3 of
                                 (SEQ ID NO: 3)
QQSDSWPPT;

HCDR1 of
                                 (SEQ ID NO: 4)
GYYMS;

HCDR2 of
                                 (SEQ ID NO: 5)
WINPLSGETNYAQKFQG;
and
```

-continued

```
HCDR3 of
                                 (SEQ ID NO: 6)
DTGELDGMNWYFDL.
```

2. The BMP1, TLL1 and/or TLL2 antibody according to claim 1, wherein the antibody comprises a VH region that is 80% identical to SEQ ID NO: 7 and/or a VL region that is 80% identical to SEQ ID NO: 8.

3. The BMP1, TLL1 and/or TLL2 antibody according to claim 1, wherein the antibody comprises a VH region that is 100% identical to SEQ ID NO: 7 and/or a VL region that is 100% identical to SEQ ID NO: 8.

4. The BMP1, TLL1 and/or TLL2 antibody according to claim 1, wherein the antibody comprises a heavy chain (HC) sequence at least 80% identical to SEQ ID NO: 10; and/or a light chain (LC) sequence at least 80% identical to SEQ ID NO: 9.

5. The BMP1, TLL1 and/or TLL2 antibody according to claim 1, wherein the antibody comprises a heavy chain (HC) sequence that is 100% identical to SEQ ID NO: 10; and/or a light chain (LC) sequence that is 100% identical to SEQ ID NO: 9.

6. A polynucleotide sequence encoding the BMP1, TLL1 and/or TLL2 antibody according to claim 1.

7. The polynucleotide sequence according to claim 6, which comprises SEQ ID NO: 6 encoding the heavy chain; and SEQ ID NO: 14 encoding the light chain.

8. An expression vector comprising the polynucleotide sequence according to claim 6, wherein the polynucleotide sequence is operatively linked to transcriptional and translational control sequences.

9. A recombinant host cell comprising the expression vector according to claim 8.

10. A method for the production of a BMP1, TLL1 and/or TLL2 antibody, which method comprises culturing the recombinant host cell according to claim 9 under conditions suitable for expression of the polynucleotide sequence, whereby a polypeptide comprising the BMP1, TLL1 and/or TLL2 antibody is produced.

11. A pharmaceutical composition comprising the BMP1, TLL1 and/or TLL2 antibody according to claim 1, and a pharmaceutically acceptable diluent or carrier.

12. The BMP1, TLL1 and/or TLL2 antibody according to claim 1, wherein the antibody is humanised.

13. The BMP1, TLL1 and/or TLL2 antibody according to claim 1, wherein the antibody is an anti-BMP1, TLL1 and/or TLL2 IgG1 antibody.

14. A BMP1, TLL1 and/or TLL2 antibody, which comprises a VH region that is 100% identical to SEQ ID NO: 7 and a VL region that is 100% identical to SEQ ID NO: 8.

15. The BMP1, TLL1 and/or TLL2 antibody according to claim 14, which comprises a light chain that is 100% identical to SEQ ID NO: 9 and a heavy chain that is 100% identical to SEQ ID NO: 10.

16. The BMP1, TLL1 and/or TLL2 antibody according to claim 15, wherein the antibody is an anti-BMP1, TLL1 and/or TLL2 IgG1 antibody.

17. A pharmaceutical composition comprising the BMP1, TLL1 and/or TLL2 IgG1 antibody according to claim 16, and a pharmaceutically acceptable diluent or carrier.

18. A polynucleotide sequence encoding the BMP1, TLL1 and/or TLL2 antibody according to claim 15.

19. An expression vector comprising the polynucleotide sequence according to claim 18, wherein the polynucleotide sequence is operatively linked to transcriptional and translational control sequences.

20. A recombinant host cell comprising the expression vector according to claim 19.

21. A method for the production of a BMP1, TLL1 and/or TLL2 antibody, which method comprises culturing the recombinant host cell according to claim 20 under conditions suitable for expression of the polynucleotide sequence, whereby a polypeptide comprising the BMP1, TLL1 and/or TLL2 antibody is produced.

22. The BMP1, TLL1 and/or TLL2 antibody according to claim 14, wherein the antibody is an anti-BMP1, TLL1 and/or TLL2 IgG1_antibody.

23. A pharmaceutical composition comprising the BMP1, TLL1 and/or TLL2 IgG1 antibody according to claim 22, and a pharmaceutically acceptable diluent or carrier.

* * * * *